US009149272B2

United States Patent
Sherts et al.

(10) Patent No.: US 9,149,272 B2
(45) Date of Patent: Oct. 6, 2015

(54) SUTURE PASSER GUIDES AND RELATED KITS AND METHODS

(71) Applicant: CooperSurgical, Inc., Trumbull, CT (US)

(72) Inventors: Charles Sherts, Westport, CT (US); Kerry Blair, Overland Park, KS (US); Robert D. Auerbach, Madison, CT (US); Mark Curtis, Sandy Hook, CT (US); James Young, Brookfield, CT (US)

(73) Assignee: CooperSurgical, Inc., Trumbull, CT (US)

( * ) Notice: Subject to any disclaimer, the term of this patent is extended or adjusted under 35 U.S.C. 154(b) by 0 days.

(21) Appl. No.: 13/723,703

(22) Filed: Dec. 21, 2012

(65) Prior Publication Data

US 2013/0165956 A1    Jun. 27, 2013

Related U.S. Application Data

(60) Provisional application No. 61/599,473, filed on Feb. 16, 2012, provisional application No. 61/580,514, filed on Dec. 27, 2011.

(51) Int. Cl.
*A61B 17/04* (2006.01)
*A61B 17/00* (2006.01)
(Continued)

(52) U.S. Cl.
CPC ......... *A61B 17/0482* (2013.01); *A61B 17/0057* (2013.01); *A61B 17/0483* (2013.01);
(Continued)

(58) Field of Classification Search
CPC ........... A61B 17/0482; A61B 17/0057; A61B 17/0469; A61B 17/0485; A61B 17/06109; A61B 17/0483; A61B 17/3462; A61B 2017/00637; A61B 2017/00663; A61B 2017/06104; A61B 2017/2927; A61B 2017/00429; A61B 2017/00986; A61B 2017/3441; A61B 2017/3445; A61B 2017/3488; A61B 2017/3492; A61B 2019/462; A61B 2019/0278; A61B 2019/461; A61B 2019/4836; A61B 2017/3484
USPC ......... 606/148, 139–144, 167, 198, 185, 145, 606/232, 190, 191, 222, 223, 228, 213, 127, 606/128, 110–115, 149, 150; 600/29, 31, 600/201, 202, 30, 131, 115; 604/272, 264, 604/93.01, 164.1–164.12, 171, 104–107
See application file for complete search history.

(56) References Cited

U.S. PATENT DOCUMENTS

| | | | |
|---|---|---|---|
| 3,817,251 A | 6/1974 | Hasson | |
| 4,089,337 A | 5/1978 | Kronner | |

(Continued)

FOREIGN PATENT DOCUMENTS

| | | | | |
|---|---|---|---|---|
| EP | 2 305 129 | 4/2011 | ............ | A61B 17/04 |
| EP | 2 412 317 | 2/2012 | ............ | A61B 17/04 |

(Continued)

OTHER PUBLICATIONS

U.S. Appl. No. 13/555,660, entitled "Endoscopic Ports and Related Kits and Methods".

(Continued)

*Primary Examiner* — Jocelin Tanner
(74) *Attorney, Agent, or Firm* — Fish & Richardson P.C.

(57) ABSTRACT

A suture passer guide that includes an elongate member having a longitudinal axis and defining a first proximal opening and a first distal opening. The first proximal and distal openings are substantially aligned with one another such that a suture passer can be extended through the first proximal and distal openings at an acute angle relative to the longitudinal axis of the elongate member. The suture passer guide can be configured to be passed through a central lumen of an endoscopic port.

41 Claims, 42 Drawing Sheets

(51) Int. Cl.
*A61B 17/34* (2006.01)
*A61B 19/00* (2006.01)

(52) U.S. Cl.
CPC ... *A61B17/3462* (2013.01); *A61B 2017/00429* (2013.01); *A61B 2017/00663* (2013.01); *A61B 2017/00986* (2013.01); *A61B 2017/3441* (2013.01); *A61B 2017/3445* (2013.01); *A61B 2017/3488* (2013.01); *A61B 2017/3492* (2013.01); *A61B 2019/461* (2013.01); *A61B 2019/4836* (2013.01)

(56) References Cited

U.S. PATENT DOCUMENTS

| | | | |
|---|---|---|---|
| 4,861,334 | A | 8/1989 | Nawaz |
| 5,002,557 | A | 3/1991 | Hasson |
| 5,197,971 | A * | 3/1993 | Bonutti ............ 606/192 |
| 5,269,772 | A | 12/1993 | Wilk |
| 5,372,583 | A | 12/1994 | Roberts et al. |
| 5,496,335 | A | 3/1996 | Thomason et al. |
| 5,501,692 | A | 3/1996 | Riza |
| 5,507,758 | A | 4/1996 | Thomason et al. |
| 5,716,369 | A | 2/1998 | Riza |
| 5,882,344 | A | 3/1999 | Stouder, Jr. |
| 5,964,773 | A | 10/1999 | Greenstein |
| 5,993,471 | A | 11/1999 | Riza et al. |
| 6,142,931 | A | 11/2000 | Kaji |
| 6,183,485 | B1 | 2/2001 | Thomason et al. |
| 6,197,002 | B1 | 3/2001 | Peterson |
| 6,203,554 | B1 | 3/2001 | Roberts |
| 6,783,516 | B2 | 8/2004 | O'Heeron et al. |
| 6,830,578 | B2 | 12/2004 | O'Heeron et al. |
| 7,842,049 | B2 | 11/2010 | Voss |
| 2003/0158572 | A1 | 8/2003 | McFarlane |
| 2004/0087978 | A1 | 5/2004 | Velez et al. |
| 2006/0025749 | A1 * | 2/2006 | Moenning ............ 604/506 |
| 2006/0030868 | A1 * | 2/2006 | Bennett, III ............ 606/148 |
| 2007/0191772 | A1 | 8/2007 | Wojcik |
| 2007/0203507 | A1 * | 8/2007 | McLaughlin et al. ...... 606/144 |
| 2008/0033459 | A1 * | 2/2008 | Shafi et al. ............ 606/144 |
| 2008/0086165 | A1 | 4/2008 | Lyon et al. |
| 2008/0097485 | A1 | 4/2008 | Shpaichler et al. |
| 2010/0280327 | A1 | 11/2010 | Nobis et al. |
| 2011/0021880 | A1 | 1/2011 | Okoniewski |
| 2011/0112557 | A1 * | 5/2011 | Beeley ............ 606/148 |
| 2011/0237901 | A1 | 9/2011 | Duke et al. |
| 2012/0029532 | A1 * | 2/2012 | Hodgkinson et al. ........ 606/139 |
| 2012/0035623 | A1 | 2/2012 | Bagaoisan et al. |
| 2012/0165611 | A1 | 6/2012 | Warren et al. |
| 2012/0238823 | A1 | 9/2012 | Hagerty et al. |
| 2012/0265223 | A1 | 10/2012 | Shpaichler et al. |
| 2014/0163323 | A1 | 6/2014 | Mohajer-Shojaee |

FOREIGN PATENT DOCUMENTS

| | | | |
|---|---|---|---|
| WO | WO 98/22040 | 5/1998 | ............ A61F 2/00 |
| WO | WO 2006/111955 | 10/2006 | |
| WO | WO 2007/000159 | 1/2007 | |
| WO | WO 2009/031991 | 3/2009 | |
| WO | WO 2009/138839 | 11/2009 | |
| WO | WO 2010/000033 | 1/2010 | |
| WO | WO 2010/081096 | 7/2010 | |
| WO | WO 2013/019370 | 2/2013 | ............ A61B 17/04 |

OTHER PUBLICATIONS

CooperSurgical, "Carter-Thomason CloseSure System," pp. 1-6; Oct. 2010.
CooperSurgical; "Marlow Balloon Cannula with Atraumatic Surface Disc," pp. 1-2, Sep. 1997.
Dr. A H Beeley, "The Beeley Trocar Brochure—Port Site Suture System Trocar," *Society of Laparoendoscopic Surgeons*, www.pssstlaparoscopy.com, p. 2, 2011.
Elashry et al., "Comparative Clinical Study of Port-Closure Techniques Following Laparoscopic Surgery," *Journal of the American College of Surgeons*, vol. 183, pp. 335-344, Oct. 1996.
International Search Report and the Written Opinion of the International Searching Authority for International Application No. PCT/US2012/071218 dated Aug. 28, 2013.
Invitation to Pay Additional Fees and, Where Applicable, Protest Fee and Annex to Form PCT/ISA/206 Communication Relating to the Results of the Partial International Search for International Application No. PCT/US2012/071218 dated Jun. 28, 2013 (12 pages).

* cited by examiner

SUTURE PASSER GUIDES AND RELATED KITS AND METHODS

CROSS-REFERENCE TO RELATED APPLICATIONS

This application claims the benefit of U.S. Provisional Patent Application No. 61/599,473, filed on Feb. 16, 2012, and U.S. Provisional Patent Application No. 61/580,514, filed on Dec. 27, 2011, each of which is incorporated by reference herein.

TECHNICAL FIELD

This disclosure relates to suture passer guides and related kits and methods.

BACKGROUND

Suture passer guides are medical devices that can be inserted through a wound, such as an endoscopic port site wound, and then used to guide a suture passer through tissue adjacent the wound in a desired manner to facilitate repair of the wound. Following an endoscopic surgical procedure, an endoscopic port is removed from an endoscopic port site wound in the patient and a suture passer guide is inserted into the wound. A suture passer is typically loaded with a suture and inserted through a passage within the suture passer guide in order to introduce the suture passer and the loaded suture through tissue adjacent one side of the wound and into the surgical cavity. The suture is then released from the suture passer, and the suture passer is removed from the passage. The suture passer is subsequently reinserted through another passage of the suture passer guide to introduce the suture grasper through tissue adjacent the other side of the wound and into the surgical cavity where the previously placed suture is grasped with the suture passer. The suture passer and the grasped suture are then removed from the passage such that the suture can be tied off to close the fascia, muscle and peritoneum layers of the endoscopic port site wound.

SUMMARY

In one aspect of the invention, a suture passer guide includes an elongate member having a longitudinal axis and an expandable member secured to a distal end region of the elongate member. The expandable member is configured to be positioned in an expanded position in which the expandable member extends radially beyond the elongate member. The elongate member defines a first proximal opening and a first distal opening that are substantially aligned with one another such that a suture passer can be extended through the first proximal and distal openings at an acute angle relative to the longitudinal axis of the elongate member and such that the suture passer, when extended through the openings with the expandable member in the expanded position, is spaced from the expandable member along the length of the expandable member.

In another aspect of the invention, a method includes inserting a suture passer guide into a wound such that a distal end region of the suture passer guide is disposed within a body cavity adjacent the wound, applying a proximal force to the suture passer guide such that an expanded member located along the distal end region of the suture passer guide applies an outward force to tissue defining the body cavity, and passing a suture passer through a passage formed in the suture passer guide such that the suture passer pierces the tissue and enters the body cavity. The suture passer is laterally spaced from the expanded member as the suture passer enters the body cavity.

In an additional aspect of the invention, a suture passer guide includes an elongate member having a longitudinal axis. The elongate member defines a first proximal opening and a first distal opening. The first proximal and distal openings are substantially aligned with one another such that a suture passer can be extended through the first proximal and distal openings at an acute angle relative to the longitudinal axis of the elongate member. The elongate member further defines a second proximal opening and a second distal opening. The second proximal and distal openings are substantially aligned with one another such that a suture passer can be extended through the first proximal and distal openings at an acute angle relative to the longitudinal axis of the elongate member. The first proximal opening is distal to the second proximal opening, and the first distal opening is distal to the second distal opening. The suture passer guide further includes an expandable member secured to a distal end region of the elongate member. The expandable member is configured to be positioned in an expanded position in which the expandable member extends radially beyond the elongate member.

In a further aspect of the invention, a method includes inserting a suture passer guide into a wound such that a distal end region of the suture passer guide is disposed within a body cavity adjacent the wound, applying a proximal force to the suture passer guide such that an expanded member located along the distal end region of the suture passer guide applies an outward force to tissue defining the body cavity, selecting one of multiple guide passages formed in the suture passer guide, and passing a suture passer through the selected guide passage such that the suture passer pierces the tissue and enters the body cavity.

In yet another aspect of the invention, a suture passer guide includes an elongate member having a longitudinal axis. The member defines a first proximal opening and a first distal opening. The first proximal and distal openings are substantially aligned with one another such that a suture passer can be extended through the first proximal and distal openings at an acute angle relative to the longitudinal axis of the elongate member. The suture passer guide further includes a seal covering at least one of the first proximal and distal openings. The seal is secured to the elongate member in a manner to form a substantially fluid-tight seal.

In an additional aspect of the invention, a method includes inserting a suture passer guide into a wound such that a distal end region of the suture passer guide is disposed within a pressurized body cavity adjacent the wound, passing a suture passer through a passage formed in the suture passer guide and through a seal that covers an opening of the passage such that the suture passer pierces tissue and enters the body cavity, and removing the suture passer from the suture passer guide via the passage. A pressure of the pressurized body cavity is maintained without re-pressurizing the body cavity while the suture passer guide is disposed in the wound.

In a further aspect of the invention, a suture passer guide includes an elongate member having a longitudinal axis. The suture passer guide further includes a block slidably disposed within a longitudinal passage defined by the elongate member. The block defines a first guide passage extending from a first proximal opening in a surface of the block to a first distal opening in the surface of the block, where the block has a longitudinal centerline that is substantially parallel to the longitudinal axis of the elongate member. The first guide passage extends at an acute angle relative to the longitudinal centerline of the block and to the longitudinal axis of the elongate member, and the first guide passage is configured to receive a suture passer therein.

Embodiments can include one or more of the following features.

In some embodiments, the suture passer guide is configured to be passed through a lumen of an endoscopic port when the expandable member is positioned in a collapsed position.

In certain embodiments, the expandable member is configured to extend laterally beyond the endoscopic port when the suture passer guide is disposed within the lumen of the endoscopic port with the distal end region extending distally from the endoscopic port and the expandable member is in the expanded position.

In some embodiments, the expandable member is configured so that when the suture passer guide is positioned within an endoscopic port wound and the expandable member is in the expanded position within a body cavity adjacent the endoscopic port site wound, the suture passer guide can be pulled proximally to apply an outward force to a wall forming the body cavity on either side of the endoscopic port wound.

In certain embodiments, the first proximal and distal openings are arranged so that when a suture passer is extended through the first proximal and distal openings at the acute angle relative to the longitudinal axis of the elongate member and the expandable member is in the expanded position and in contact with an inner surface of a wall forming a body cavity, the suture passer pierces the inner surface of the wall at a distance of about 0.5 cm to about 2.0 cm from an outer surface of the elongate member. The distance is measured perpendicularly to the longitudinal axis of the elongate member.

In some embodiments, the expandable member is a mechanically expandable member.

In certain embodiments, the expandable member is biased to the expanded position and is configured to automatically expand as the expandable member is extended through and distally beyond a lumen of an endoscopic port.

In some embodiments, the expandable member includes multiple collapsible arms. A first end region of each of the collapsible arms is secured to the distal end region of the elongate member. A second end region of each of the collapsible arms is secured to a base that is axially moveable relative to the elongate member. A middle region of each of the collapsible arms is secured to the first and second end regions of each of the collapsible arms.

In certain embodiments, axial movement of the base distally relative to the elongate member causes the expandable member to collapse, and axial movement of the base proximally relative to the elongate member causes the expandable member to expand.

In some embodiments, the suture passer guide further includes a shaft that is connected to the base and extends through a lumen of the elongate member. The shaft is axially movable relative to the elongate member to move the base axially relative to the elongate member.

In certain embodiments, each of the collapsible arms includes a first hinge located between the first end region and the middle region. A second hinge is located between the middle region and the second end region. Each of the collapsible arms is bent at the first and second hinges when the expandable member is in the expanded position.

In some embodiments, the base has a blunt, rounded distal surface.

In certain embodiments, when the expandable member is in the expanded position, the collapsible arms extend radially beyond an outer surface of the elongate member.

In some embodiments, when the expandable member is in a collapsed position, the collapsible arms are positioned substantially flush with the outer surface of the elongate member.

In certain embodiments, the suture passer guide further includes a suture positioning arm secured to an arm of the expandable member and configured to extend radially outward from the arm. The suture positioning arm is configured to hold a suture.

In some embodiments, the suture passer guide further includes a film secured to the expandable member. The film at least partially surrounds the expandable member.

In certain embodiments, the film is substantially fluid impermeable.

In some embodiments, the suture passer guide further includes a stretchable polymeric tube surrounding the expandable member.

In certain embodiments, the expandable member is an inflatable member.

In some embodiments, the suture passer guide further includes a shaft having a distal end region secured to the expandable member. Distal movement of the shaft places the expandable member in a collapsed position and proximal movement of the shaft places the expandable member in the expanded position.

In certain embodiments, the shaft is biased to a proximal position such that the expandable member is biased to the expanded position.

In some embodiments, the suture passer guide further includes a spring connecting the shaft to the elongate member. The spring biases the shaft to the proximal position.

In certain embodiments, the suture passer guide further includes a shaft disposed within a lumen of the elongate member. The shaft defines a first passage that can be aligned with the first proximal and distal openings.

In some embodiments, the first passage is aligned with the first proximal and distal openings when the shaft is disposed in a proximal position.

In certain embodiments, the shaft is biased to the proximal position.

In some embodiments, the shaft defines a second passage that can be aligned with second proximal and distal openings defined by the elongate member.

In certain embodiments, the second passage is aligned with the second proximal and distal openings when the shaft is disposed in the proximal position.

In some embodiments, the suture passer guide further includes one or more seals that cover(s) at least one of the first proximal and distal openings.

In certain embodiments, the seal substantially prevents gases from passing through the at least one of the first proximal and distal openings such that pressure within a pressurized body cavity can be substantially maintained while the suture passer guide is disposed in the pressurized body cavity.

In some embodiments, the seal covers the first distal opening.

In certain embodiments, the seal is a plug disposed within the at least one of the first proximal and distal openings.

In some embodiments, the plug is a self-sealing plug.

In certain embodiments, the self-sealing plug is formed of silicone.

In some embodiments, the seal is a polymeric tube.

In certain embodiments, the polymeric tube is a heat shrink tube.

In some embodiments, the polymeric tube surrounds a portion of the elongate member that defines the first distal opening.

In certain embodiments, the elongate member defines a second proximal opening and a second distal opening that are substantially aligned with one another such that a suture passer can be extended through the second proximal and distal openings at an acute angle relative to the longitudinal axis of the elongate member.

In some embodiments, the first proximal opening is distal to the second proximal opening, and the first distal opening is distal to the second distal opening.

In certain embodiments, the elongate member defines a third proximal opening and a third distal opening that are substantially aligned with one another such that a suture passer can be extended through the third proximal and distal openings at an acute angle relative to the longitudinal axis of the elongate member.

In some embodiments, the elongate member defines a fourth proximal opening and a fourth distal opening that are substantially aligned with one another such that a suture passer can be extended through the fourth proximal and distal openings at an acute angle relative to the longitudinal axis of the elongate member.

In certain embodiments, the first distal opening is located in a first colored region of the elongate member and the second distal opening is located in a second colored region of the elongate member. The first colored region is a different color than the second colored region.

In some embodiments, the colored regions include colored bands that at least partially surround the elongate member.

In certain embodiments, the colored regions indicate to the user which of the proximal and distal openings should be used for a procedure.

In some embodiments, the colored regions associated with the distal openings indicate a range of distances between an inner surface of a body cavity and an outer surface of a body when the suture passer guide is disposed within the wound with the expandable member expanded and in contact with the inner surface of the body cavity.

In certain embodiments, the indicated range of distances is 2.5-5 cm when the outer surface of the body lies along the colored region associated with the first distal opening.

In some embodiments, the indicated range of distances is 5-12 cm when the outer surface of the body lies along the colored region associated with the second distal opening.

In certain embodiments, the suture passer guide further includes gripping members along a proximal end region of the elongate member.

In some embodiments, the gripping members include etched markings formed along the outer surface of the elongate member.

In certain embodiments, the suture passer guide further includes a measuring scale along a distal end region of the elongate member. The scale indicates a distance between markings of the scale and a proximal end of the expandable member.

In some embodiments, the measuring scale can be used to determine a thickness of tissue through which the suture passer guide is inserted.

In certain embodiments, at least one of the first proximal and distal openings is formed in a sidewall of the elongate member.

In some embodiments, the first proximal and distal openings are formed in a sidewall of the elongate member.

In certain embodiments, the first proximal opening is formed in a head at a proximal end of the elongate member.

In some embodiments, the first proximal opening is formed in a proximal end surface of the head.

In certain embodiments, the first proximal and distal openings are defined by respective portions of the elongate member that are circumferentially spaced by about 180 degrees.

In some embodiments, the second proximal and distal openings are defined by respective portions of the elongate member that are circumferentially spaced by about 180 degrees.

In certain embodiments, the expandable member includes multiple collapsible arms that are spaced around a circumference of the expandable member.

In some embodiments, a gap between two of the multiple collapsible arms that are adjacent one another extends about 30° to about 180° (e.g., about 30° to about 90°) around the circumference of the expandable member.

In certain embodiments, the gap is longitudinally aligned with the first distal opening.

In some embodiments, the expandable member includes only two collapsible arms around the circumference of the expandable, and centerlines of the two collapsible arms are positioned about 180° apart around the circumference of the expandable member.

In certain embodiments, the multiple collapsible arms are arranged in multiple groups that are spaced apart around a circumference of the expandable member.

In some embodiments, a gap between two consecutive groups of collapsible arms is larger than gaps between adjacent collapsible arms within the groups.

In certain embodiments, the gap between the two consecutive groups of collapsible arms extends about 90° to about 135° around the circumference of the expandable member.

In some embodiments, each of the gaps between the adjacent collapsible arms within the groups extends about 25° to about 60° around the circumference of the expandable member.

In certain embodiments, each group comprises multiple collapsible arms.

In some embodiments, a gap between two consecutive groups of collapsible arms is longitudinally aligned with the first distal opening of the elongate member.

In certain embodiments, the multiple collapsible arms are unequally spaced around the circumference of the expandable member.

In some embodiments, a wall of the elongate member includes a first elongate depression extending from the first proximal opening.

In certain embodiments, a proximal end region of the shaft forms an opening that holds a spring, the spring coupling the proximal end region of the shaft to a plunger disposed at a proximal end region of the elongate member.

In some embodiments, the gripping members are in the form of depressions formed along the outer surface of the elongate member.

In certain embodiments, the elongate member defines a guide passage that extends from the proximal opening to the distal opening.

In some embodiments, an entire length of the guide passage is laterally offset from the longitudinal axis such that the guide passage does not intersect the longitudinal axis.

In certain embodiments, the suture passer guide further includes an inner shaft that extends along the longitudinal axis.

In some embodiments, the guide passage extends at an angle of about 10° to about 30° relative to the longitudinal axis.

In certain embodiments, the proximal and distal openings are circumferentially spaced around the elongate member by about 150° to about 170°.

In some embodiments, the elongate member defines a second guide passage that extends from a second proximal opening to a second distal opening.

In certain embodiments, an entire length of the guide passage is laterally offset from the longitudinal axis in a first direction such that the guide passage does not intersect the longitudinal axis, and an entire length of the second guide passage is laterally offset from the longitudinal axis in a second direction opposite the first direction such that the second guide passage does not intersect the longitudinal axis.

In some embodiments, the elongate member defines a lumen that extends along the longitudinal axis, and the suture passer guide further comprises an inner rod that is slidable within the lumen.

In certain embodiments, each of the guide passages extends at an angle of about 10° to about 30° relative to the longitudinal axis.

In some embodiments, the proximal and distal openings are circumferentially spaced around the elongate member by about 150° to about 170°, and the second proximal and distal openings are circumferentially spaced around the elongate member by about 150° to about 170°.

In certain embodiments, the proximal opening and the second distal opening are circumferentially spaced by about 10° to about 30° around the elongate member, and the second proximal opening and the distal opening are circumferentially spaced by about 10° to about 30° around the elongate member.

In some embodiments, three or more guide passages are longitudinally spaced from one another along the elongate member.

In certain embodiments, the method further includes expanding the member located along the distal end region of the suture passer guide.

In some embodiments, the member is an inflatable member and expanding the member includes introducing fluid into the member.

In certain embodiments, the member is a mechanically expandable member.

In some embodiments, the mechanically expandable member is biased to an expanded position.

In certain embodiments, the outward force is applied to the tissue while piercing the tissue with the suture passer.

In some embodiments, the wound is an endoscopic port site wound.

In certain embodiments, inserting the suture passer guide into the endoscopic port site wound includes inserting the suture passer guide into a lumen of an endoscopic port disposed within the endoscopic port site wound.

In some embodiments, the body cavity is a peritoneal cavity.

In certain embodiments, a pneumoperitoneum is maintained while the suture passer guide is disposed within the endoscopic port site wound.

In some embodiments, the method further includes tilting the suture passer guide within the body cavity such that the suture passer guide can guide a distal end region of the suture passer to a location within a grasping proximity of a suture within the body cavity.

In certain embodiments, the suture passer guide is tilted about 20° to about 90° relative to a longitudinal axis of the wound.

In some embodiments, the method further includes passing a second suture passer through a second passage formed in the suture passer guide such that the second suture passer pierces the tissue and enters the body cavity, the second suture passer being laterally spaced from the expanded member as the suture passer enters the body cavity.

In certain embodiments, the first and second suture passers are simultaneously disposed within the first and second passages, respectively.

In some embodiments, an entire length of the passage is laterally offset from a longitudinal axis of the suture passer guide such that the guide passage does not intersect the longitudinal axis.

In certain embodiments, the passage extends at an angle about 10° to about 30° relative to the longitudinal axis.

In some embodiments, proximal and distal openings of the passage are circumferentially spaced around the elongate member by about 150° to about 170°.

In certain embodiments, the method further includes selecting a second one of the multiple guide passages formed in the suture passer guide and passing a second suture passer through the second one of the multiple guide passages such that the second suture passer pierces the tissue and enters the body cavity, the second suture passer being laterally spaced from the expanded member as the suture passer enters the body cavity.

In some embodiments, the first and second suture passers are simultaneously disposed within the one of the multiple guide passages and the second one of the multiple guide passages, respectively.

In certain embodiments, an entire length of the one of the multiple guide passages is laterally offset from a longitudinal axis of the suture passer guide such that the one of the multiple guide passages does not intersect the longitudinal axis.

In some embodiments, the one of the multiple guide passages extends at an angle of about 10° to about 30° relative to the longitudinal axis.

In certain embodiments, proximal and distal openings of the one of the multiple guide passages are circumferentially spaced around the elongate member by about 150° to about 170°.

In some embodiments, the first proximal and distal openings are arranged so that when a suture passer is extended through the first proximal and distal openings at the acute angle relative to the longitudinal axis of the elongate member and the expandable member is in the expanded position and in contact with an inner surface of a wall forming a body cavity, the suture passer pierces the inner surface of the wall at a distance of about 0.5 cm to about 2.0 cm from an outer surface of the elongate member. The distance is measured perpendicularly to the longitudinal axis of the elongate member. The second proximal and distal openings are arranged so that when a suture passer is extended through the first proximal and distal openings at the acute angle relative to the longitudinal axis of the elongate member and the expandable member is in the expanded position and in contact with the inner surface of the wall forming the body cavity, the suture passer pierces the inner surface of the wall at a distance of about 0.5 cm to about 2.0 cm from the outer surface of the elongate member. The distance is measured perpendicularly to the longitudinal axis of the elongate member.

In certain embodiments, the expandable member is biased to the expanded position.

In some embodiments, the expandable member is configured to automatically expand as the expandable member is extended through and distally beyond a lumen of an endoscopic port.

In certain embodiments, the suture passer guide further includes a first suture positioning arm secured to an arm of the expandable member and configured to extend radially outward from the arm. The first suture positioning arm is configured to hold a suture.

In some embodiments, a portion of the first suture positioning arm that is configured to hold a suture is aligned with the first proximal and distal openings.

In certain embodiments, the suture passer guide further includes a second suture positioning arm secured to an arm of the expandable member and configured to extend radially outward from the arm. The second suture positioning arm is configured to hold a suture.

In some embodiments, a portion of the second suture positioning arm that is configured to hold a suture is aligned with the second proximal and distal openings.

In certain embodiments, the elongate member defines a third proximal opening and a third distal opening that are substantially aligned with one another such that a suture passer can be extended through the third proximal and distal openings at an acute angle relative to the longitudinal axis of the elongate member.

In some embodiments, the elongate member defines a fourth proximal opening and a fourth distal opening that are substantially aligned with one another such that a suture passer can be extended through the fourth proximal and distal openings at an acute angle relative to the longitudinal axis of the elongate member.

In certain embodiments, first proximal and distal openings and the second proximal and distal openings are arranged such that, when the expandable member is expanded and in contact with an inner surface of a wall forming a body cavity, a suture passer extended through the first proximal distal openings and a suture passer extended through the second proximal and distal openings will pierce the inner surface of the wall at substantially the same point.

In some embodiments, the point at which the suture passer will pierce the inner surface of the wall is a distance of about 0.5 cm to about 2.0 cm from the outer surface of the elongate member. The distance is measured perpendicularly to the longitudinal axis of the elongate member.

In certain embodiments, at least one of the first proximal and distal openings and at least one of the second proximal and distal openings is formed in a sidewall of the elongate member.

In some embodiments, the first proximal and distal openings and the second proximal and distal openings are formed in a sidewall of the elongate member.

In certain embodiments, the first and second proximal openings are formed in a head at a proximal end of the elongate member.

In some embodiments, the first and second proximal openings are formed in a proximal end surface of the head.

In certain embodiments, selecting the one of the multiple guide passages includes identifying a region of the suture passer guide along which an outer surface of the tissue defining the body cavity lies when the outward force is being applied to the tissue.

In some embodiments, the suture passer guide includes multiple colored regions, and selecting the multiple guide passages includes identifying the colored region along which the outer surface of the tissue defining the body cavity lies when the outward force is being applied to the tissue.

In certain embodiments, the suture passer guide forms a first guide passage and a second guide passage. The first guide passage is located distal to the second guide passage. The first guide passage is selected when the outer surface of the tissue defining the body cavity lies along one of the multiple colored regions, and the second guide passage is selected when the outer surface of the tissue defining the body cavity lies along another of the multiple colored regions.

In some embodiments, the suture passer guide is configured to be passed through a lumen of an endoscopic port.

In certain embodiments, the suture passer guide further includes an expandable member secured to a distal end region of the elongate member. The expandable member is configured to be positioned in an expanded position in which the expandable member extends radially beyond the elongate member.

In some embodiments, the seal substantially prevents gases from passing through the passage while the suture passer guide is disposed in the pressurized body cavity.

In certain embodiments, the passage extends between a first proximal opening defined by the suture passer guide and a first distal opening defined by the suture passer guide, and the seal covers the first distal opening.

In some embodiments, the seal is a plug disposed within the passage.

In certain embodiments, the plug is a self-sealing plug.

In some embodiments, the seal is a polymeric tube.

In certain embodiments, the polymeric tube is a heat shrink tube.

In some embodiments, the wound is an endoscopic port site wound.

In certain embodiments, inserting the suture passer guide into the endoscopic port site wound includes inserting the suture passer guide into a lumen of an endoscopic port disposed within the endoscopic port site wound.

In some embodiments, the body cavity is a peritoneal cavity.

In certain embodiments, a pneumoperitoneum is maintained without re-insufflating the peritoneal cavity while the suture passer guide is disposed within the endoscopic port site wound.

In some embodiments, the method further includes applying a proximal force to the suture passer guide such that an expanded member located along a distal end region of the suture passer guide applies an outward force to tissue defining the body cavity.

In certain embodiments, the acute angle is about 12° to about 30°.

In some embodiments, a longitudinal distance between the first proximal opening and the first distal opening is about 3 cm to about 6 cm.

In certain embodiments, the block comprises an indicator that indicates when the block is properly longitudinally positioned during use.

In some embodiments, the indicator is longitudinally positioned between the first proximal opening and the first distal opening.

In certain embodiments, the indicator is a projection that extends from a surface of the block.

In some embodiments, the indicator is of a color that is different than a color of a portion of the block adjacent to the indicator.

In certain embodiments, the block has a length of about 5 cm to about 10 cm.

In some embodiments, the block further comprises a friction-generating feature.

In certain embodiments, the friction-generating feature includes one or more cantilevered spring arms extending from a surface of the block.

In some embodiments, the friction-generating feature includes one or more recesses extending from a surface of the block, the one or more recesses sized to retain one or more complimentary projections extending from an inner surface of the elongate member.

In certain embodiments, the block further includes a button configured to engage a recess included within the block maintain a longitudinal position of the block.

In some embodiments, the block further includes a seal that covers at least one of the first proximal and first distal openings.

In certain embodiments, the elongate member includes first and second slots that are centrally aligned with the first proximal opening and the first distal opening, respectively.

In some embodiments, the first and second slots are sized to provide access to the first proximal and first distal openings, respectively.

In certain embodiments, the suture passer guide further includes a shaft disposed within a lumen of the elongate member, the shaft including two opposing rails that define a central channel therebetween, the central channel being sized and shaped to receive the block.

In some embodiments, the block defines two opposing rectangular-shaped recesses sized and shaped to receive the two opposing rails of the central channel such that the block can slide longitudinally within the central channel of the shaft.

In certain embodiments, the central channel has a length of about 11 cm to about 12 cm.

In some embodiments, the block has a length of about 9 cm to about 10 cm.

In certain embodiments, the block can slide about 2 cm to about 3 cm along the central channel.

In some embodiments, the central channel is rectangular.

In certain embodiments, the shaft is biased to the proximal position.

In some embodiments, the shaft is coupled at a proximal end region of the shaft, the channel sized to hold a spring, the spring coupling the proximal end region of the shaft to a plunger disposed at a proximal end region of the elongate member, the plunger being configured to move the shaft axially within the elongate member.

In certain embodiments, the block further includes a second guide passage extending from a second proximal opening in the surface of the block to a second distal opening in the surface of the adjustable block, wherein the second guide passage extends at an acute angle relative to the longitudinal centerline of the adjustable block and to the longitudinal axis of the elongate member.

In some embodiments, the first and second slots of the elongate tubular member are centrally aligned with the second distal opening and the second proximal opening, respectively.

In certain embodiments, the first and second slots are sized and shaped to provide a suture passer with access to the second distal and second proximal openings, respectively.

In some embodiments, when a suture passer is extended through the second guide passage with the expandable member in the expanded position, the suture passer is spaced from the expandable member along a length of the expandable member.

Embodiments can include one or more of the following advantages.

In certain embodiments, surgical procedures utilizing the suture passer guide can be carried out in less time than those that require an endoscopic port to be removed before inserting a suture passer guide. Upon inserting the suture passer guide within the lumen of the endoscopic port and subsequently removing the endoscopic port, the port site wound forms a partial seal with the outer surface of the suture passer guide such that gases within the surgical cavity are substantially prevented from escaping through the wound and the inflation pressure within the surgical cavity is substantially maintained. Thus, inserting the suture passer guide through the lumen of the endoscopic port eliminates the time that would otherwise be required to re-insufflate the surgical cavity following removal of the endoscopic port. Furthermore, inserting the suture passer guide through the endoscopic port removes the need and time required to relocate the port site wound and navigating the suture passer guide through the wound following removal of the endoscopic port, which is required when using a type of suture passer guide that is inserted directly into the port site wound after removing the endoscopic port.

By inserting the suture passer guide through the endoscopic port rather than directly into the port site wound, tissue damage that might otherwise result from inserting a suture passer guide directly into the wound can also be avoided. For example, when an endoscopic port is removed from a port site wound and then replaced by a suture passer guide, damage can be caused to the tissue surrounding the wound upon inserting the suture passer guide into the wound. With certain patients, particularly obese patients, it is often times difficult to relocate the original wound through the various layers of tissue within the wall forming the surgical cavity (i.e., the surgical cavity wall). In attempting to do so, the surgeon may inadvertently puncture tissue (e.g., fascia) adjacent the original wound, thereby creating an additional wound or enlarging the original wound. By designing the suture passer guide so that it can be inserted through the endoscopic port, the incidence of such inadvertent punctures can be reduced or eliminated.

In addition, wound repair procedures utilizing the suture passer guides described herein can result in improved placement of the suture as compared to repair procedures in which no such suture passer guide is used to facilitate placement of the suture. As a result, the quality of the repair can be improved as compared to those procedures that utilize no such suture passer guide.

In certain embodiments, positioning the expandable member, in its expanded form, against the lining of the surgical cavity wall (e.g., by applying a proximal force to the suture passer guide) helps to position the suture passer guide in a desired position relative to the surgical cavity wall to allow for optimal passage of the suture passer through the tissue of the wall. The passage and openings of the suture passer guide can, for example, be positioned in a desired manner relative to the inner surface of the surgical cavity wall such that a desired distance or bite is achieved between the placed suture and the outer surface of the suture passer guide (or the port site wound in which the suture passer guide is situated), along the inner surface of the surgical cavity wall. Positioning the passage and openings of the suture passer guide a known distance from the inner surface of the surgical cavity wall, as opposed to a known distance from the outer surface of the surgical cavity wall as is done in certain suture passer guides currently in use, can lead to more consistent high quality wound repairs. Pulling the expanded expandable member against the lining of the surgical cavity wall can also provide a greater space within the surgical cavity and thus help to ensure that unwanted tissue and organs are not inadvertently pierced with the suture passer.

Positioning the expandable member, in its expanded form, against the inner lining or inner surface of the surgical cavity wall can also help to prevent gases within the surgical cavity from escaping through the wound, thereby aiding in maintaining inflation pressure of the surgical cavity. In certain embodiments, for example, the suture passer guide is equipped with a film or other gas-impermeable material positioned over the expandable member. This arrangement can help to ensure that gases within the surgical cavity do not escape into the port site wound via the expandable member. Thus, the film can prevent loss of inflation pressure within the surgical cavity during use of the suture passer guide.

In certain embodiments, the suture passer guide includes guide passages configured such that approximately the same amount of tissue is grasped by a suture on either side of the port site wound when a suture passer is used in combination with the suture passer guide to place a suture in the surgical cavity wall. In other words, the geometry of the guide passages helps to ensure that the bite of the suture is approximately equally distributed on both sides of the wound. An equal bite distribution can improve the quality of the wound repair and reduce the time required for the wound to heal.

In certain embodiments, the suture passer guide includes guide passages at two different locations along the suture passer guide, enabling the suture passer guide to be used for obtaining a desired suture bite in patients having a variety of different surgical cavity wall thicknesses. Because the same suture passer guide can be used for patients of various different sizes, the number of suture passer guides required to be kept on hand for a surgeon's use can be reduced.

In certain embodiments, the suture passer guide includes colored regions (e.g., colored bands) associated with the different guide passages along the suture passer guide. The colored regions can help the user to select and use the passage that will result in an optimal thickness of tissue being sutured when the suture passer is passed through the selected passage with a grasped suture. Furthermore, in certain cases, a surgeon can quickly and easily approximate the surgical cavity wall thickness by noting the locations of the colored regions relative to the outer surface of the surgical cavity wall (e.g., by identifying the colored region that is located at the outer surface of the tissue of the surgical cavity wall).

In some embodiments, the suture passer guide includes seals, such as self-sealing plugs, that seal the passages of the suture passer guide. The seals can help to prevent loss of inflation pressure within the surgical cavity during use of the suture passer guide and can thus reduce or eliminate the need to re-insufflate the surgical cavity during a wound closing procedure.

In certain embodiments, the diameter of the elongate member of the suture passer guide is approximately equal to or only slightly less than the inner diameter of the lumen of the endoscopic port (or the inner diameter of seals, such as o-rings, positioned in the lumen of the endoscopic port), such that gases within the surgical cavity are inhibited from escaping through the lumen while the suture passer guide is disposed within the lumen. This can reduce or eliminate the need to re-insufflate the surgical cavity during a wound closing procedure.

In some embodiments, the suture passer guide includes ruler markings that serve to indicate a thickness of the surgical cavity wall. In such embodiments, the suture guide passer can be used to quickly and easily determine the thickness of the surgical cavity wall.

In certain embodiments, the expandable member of the suture passer guide includes multiple collapsible arms that are spaced from one another around the circumference of the expandable member, and certain collapsible arms are circumferentially spaced from one another by about 30° to about 60°. The circumferential gap between certain collapsible arms can be longitudinally aligned with the distal opening through which the suture passer is extended during use. The size and location of the gap between the adjacent collapsible arms can help to ensure that a sufficient degree of tiltability of the suture passer guide is permitted in the region in which a suture passer exits the suture passer guide during use and can thus increase the ease with which the user can navigate the suture passer within a surgical cavity to grasp a suture.

In some embodiments, the expandable member of the suture passer guide includes collapsible arms that are arranged in groups that are spaced from one another around the circumference of the expandable member. Circumferential gaps between the groups of the collapsible arms are larger than circumferential gaps between adjacent collapsible arms within the groups. The circumferential gaps between the groups of arms can be longitudinally aligned with the distal opening through which the suture passer is extended during use. The relatively large circumferential gaps between the groups of collapsible arms can improve the ease with which the suture passer guide can be tilted within a wound of a surgical wall. This arrangement can help to ensure that a sufficient degree of tiltability of the suture passer guide is permitted in the region in which a suture passer exits the suture passer guide during use and can thus increase the ease with which the user can navigate the suture passer within a surgical cavity to grasp a suture.

The alignment of the circumferential gaps with the openings (i.e., in the direction in which the suture passer guide is tilted during use) reduces the force required to tilt the suture passer guide within the wound during use of the suture passer guide (as compared to the force that would be required to tilt a suture passer guide including an expandable member having collapsible arms that form smaller circumferential gaps that are aligned with the openings). Accordingly, while the suture passer guide is tilted within the wound and in contact with the inner lining of the surgical cavity, a distal end of a suture passer can be placed within adequate proximity to a suture within a surgical cavity of a patient.

In certain embodiments, a suture passer guide includes elongate depressions that extend upward from the proximal openings within the elongate tubular member and serve to narrow a portion of the wall of the elongate tubular member, thereby reducing the volume between the inner surface of the elongate tubular member and an internal shaft disposed within the elongate tubular member. Such a reduced volume between the inner surface of the elongate tubular member and the internal shaft reduces the region through which gases can pass through the suture passer guide. Therefore, this arrangement can reduce the loss of inflation pressure from the surgical cavity through the suture passer guide during use of the suture passer guide.

In certain embodiments, the expandable member of the suture passer guide includes multiple groups of collapsible arms arranged around the circumference of the elongate member. Grouping of the collapsible arms provides circumferential gaps between the groups and around the circumference of the expandable member, where a size (i.e., an arc length) of the circumferential gaps depends on the number of collapsible arms included within each group and a width of the collapsible arms. While a smaller circumferential gap reduces the ease with which the suture passer guide can be tilted within a wound, the additional collapsible arms of the corresponding expandable member provide additional surface area upon which the traction force between the expandable member and the inner lining of the surgical cavity can be distributed during use of the suture passer guide. The increased distribution of the traction force improves the stability of the suture passer guide while the suture passer guide is held against the inner lining of the surgical cavity and further reduces the probability that any collapsible arm will tear or otherwise damage the inner lining of the surgical cavity while the suture passer guide is held against the inner lining of the surgical cavity.

In some embodiments, a suture passer guide includes a moveable guide passage block that allows a location of the guide passages to be adjusted. The sliding capability of the block allows the suture passer guide to be adjusted for use with surgical walls of different thickness (e.g., a thickness of about 2 cm to about 10 cm). Accordingly, during use of the guide passage, the block is adjusted until indicators on the surface of the block are aligned with an external skin layer of the surgical wall. In this manner, the proximal openings within the elongate tubular member are visible to the user, while the distal openings within the elongate tubular member are positioned below the external skin layer of the surgical wall within the wound. The sliding capability of the block allows the guide passages to be positioned for optimal guidance of a suture passer through the surgical wall and thus can promote effective closure of appropriate layers of the surgical wall. Furthermore, the single set of guide passages included within the adjustable block allows the suture passer guide to be operated with greater simplicity in that the user of the suture passer guide does not have to select a proper set of guide passages from more than one set of guide passages.

In some embodiments, a suture passer guide includes non-crossing guide passages that are located on opposites of an internal shaft assembly within an elongate tubular member of the suture passer guide. A relatively small diameter of a central rod included within the internal shaft assembly provides a relatively close fit of the central rod within an internal slot of the elongate tubular member (as compared to the fit of the internal shaft within the lumen of the elongate tubular member of the suture passer guide having intersecting guide passages. The close fit reduces the region through which gases can pass through the suture passer guide and thus can reduce the loss of inflation pressure from the surgical cavity through the suture passer guide during use of the suture passer guide.

The non-crossing guide passages provide several advantages to the structure and use of the suture passer guide, as compared to the structure and use of suture passer guides having guide passages that intersect one another along the longitudinal axis of the elongate member. For example, during use of suture passer guides that include intersecting guide passages, as the suture passer is passed through the second guide passage of the suture passer guide to retrieve the end of the suture that is located within the surgical cavity, care must be taken to prevent the suture passer from damaging the portion of the suture that extends through the common center region of the guide passages. In contrast, the non-crossing guide passages allow a user of the suture passer to avoid this potential complication since a suture passer will not come into contact with a suture extending through one guide passage while the suture passer is being passed through the other guide passage.

As another example, during use of suture passer guides having intersecting guide passages, as the suture passer is passed through the guide passages of the suture passer guide, care must be taken to prevent the distal end of the suture passer from becoming lodged within small gaps located between the lumen of the elongate tubular member and the internal shaft. In some instances, such contact between a suture passer and a suture passer guide could damage either or both of the suture passer and the suture passer guide. The integral feature of the non-crossing guide passages (i.e., the guide passages extending through a solid core of the elongate tubular member) prevents such a complication since the non-crossing guide passages do not have any gaps in their formations through the solid core of the elongate tubular member.

As a further example, the upper distal guide passage openings of suture passer guides including intersecting guide passages can, in certain cases, overlap with a portion of the lower proximal guide passage openings. During use of suture passer guides having such a guide passage configuration, care must be taken to prevent the distal end of the suture passer from exiting the wrong set of guide passage openings. For example, when the suture passer guide is passed through the upper guide passages care must be taken to prevent the suture passer from exiting the suture passer guide through the lower proximal openings and therefore passing through the peritoneum at undesired puncture points. The circumferential offset of the non-crossing left and right guide passages (in an embodiment where the suture passer includes two or more sets of guide passages) prevents such a complication since distal openings of an upper set of guide passages will not overlap proximal openings of a lower set of guide passages. Furthermore, the non-overlapping feature of the guide passage openings results in maximal guide passage surface areas that can optimally guide a suture passer through the suture passer guides.

In yet another example, intersection regions of the guide passages within suture passer guides including intersecting guide passages result in relatively thinned, weakened wall sections (i.e., resulting from void spaces generated by the intersection regions in the wall sections) of the elongate tubular member as compared to thicker, stronger wall sections of the elongate tubular member of the suture passer guide having non-crossing guide passages. The absence of such void guide passage intersection regions provides the elongate tubular member with thicker, stronger wall sections that can better withstand forces exerted on the wall sections as the elongate tubular member is assembled (e.g., bonded together from the wall sections). Furthermore, due to the thicker, stronger wall sections of the elongate tubular member, the elongate tubular member can include more guide passages relative to its structural integrity (as compared to the elongate tubular member of the suture passer guide including intersecting guide passages). Spacing a larger number of guide passages along the length of the elongate tubular member can allow the suture passer guide to be used to repair surgical walls having a larger range of thicknesses as compared those that can be repaired using the suture passer guide including intersecting guide passages. Additionally, the absence of a guide passage intersection void region within the elongate tubular member allows the guide passages to be oriented at any angle with respect to the longitudinal axis of the elongate tubular member. In contrast, the angle at which the intersecting guide passages are oriented with respect to the longitudinal axis of the elongate tubular member is limited by a size of the resulting guide passage intersection void region that can be allowed to maintain a desired level of structural integrity of the elongate tubular member.

In another example, the non-crossing guide passages allow two suture passers to be passed through the suture passer guide simultaneously, while the intersecting guide passages only allow one suture passer to be passed through the suture passer guide at a time.

In a further example, the circumferential offset of the non-crossing guide passages improves the aesthetics of the suture passer guide in that only one guide passage opening is completely visible from the outside of the elongate tubular member at a time, whereas the alignment of the intersecting guide passages provides that at least two openings are visible simultaneously from the outside of the elongate tubular member. A smaller number of visible openings in the elongate tubular member provides a simpler, cleaner look to the suture passer guide.

Other aspects, features, and advantages will be apparent from the description and drawings, and from the claims.

DETAILED DESCRIPTION

Figure 1:
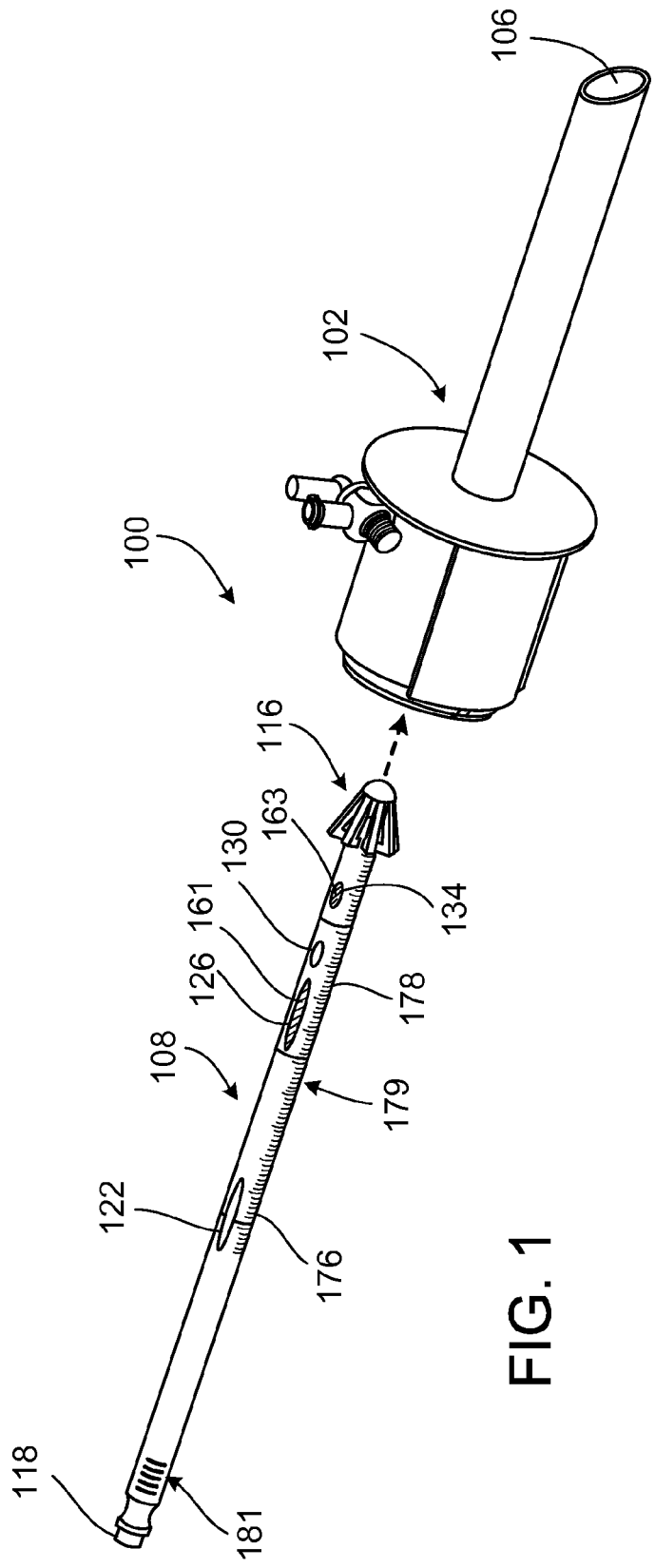
FIG. 1 is a surgical assembly that includes an endoscopic port and a suture passer guide that includes an expandable member disposed at a distal end region of the suture passer guide and that can be passed through a central lumen of the endoscopic port.

FIG. 1 illustrates a surgical assembly 100 that includes an endoscopic port 102 and a suture passer guide 108 that can be passed through a central lumen 106 of the endoscopic port 102. The suture passer guide 108 includes an expandable member 116 secured to a distal end region of an elongate tubular member 114. The expandable member 116 can be expanded within a surgical cavity in order to retain the suture passer guide 108 within the surgical cavity during a procedure to repair an endoscopic port site wound. The suture passer guide 108 further includes guide passages 136, 138, 140, 142 (shown in FIG. 2) that can be used to guide a suture passer and a suture grasped by the suture passer in a desired manner through tissue adjacent the endoscopic port site wound and into the surgical cavity.

Following completion of an endoscopic surgical procedure (e.g., a laparoscopic surgical procedure) that utilizes the endoscopic port 102, the suture passer guide 108 is inserted through the central lumen 106 of the endoscopic port 102 such that the expandable member 116 of the suture passer guide 108 is positioned within the surgical cavity (e.g., abdominal cavity) of the patient. The endoscopic port 102 is then removed from the endoscopic port site wound, leaving the suture passer guide 108 positioned within the wound and the expandable member 116 of the suture passer guide 108 positioned within the surgical cavity. A suture passer is subsequently inserted through selected guide passages of the suture passer guide 108 along with a suture to position the suture in a desired manner within the tissue of the patient and allow for closure of the port site wound. Because the suture passer guide 108 can be passed through the central lumen 106 of the endoscopic port 102, it is not necessary to remove the endoscopic port 102 from the port site wound prior to positioning the suture passer guide 108 within the wound. This can simplify the process of inserting the suture passer guide 108 into the surgical cavity and can reduce the time required to close the port site wound.

Figure 2:
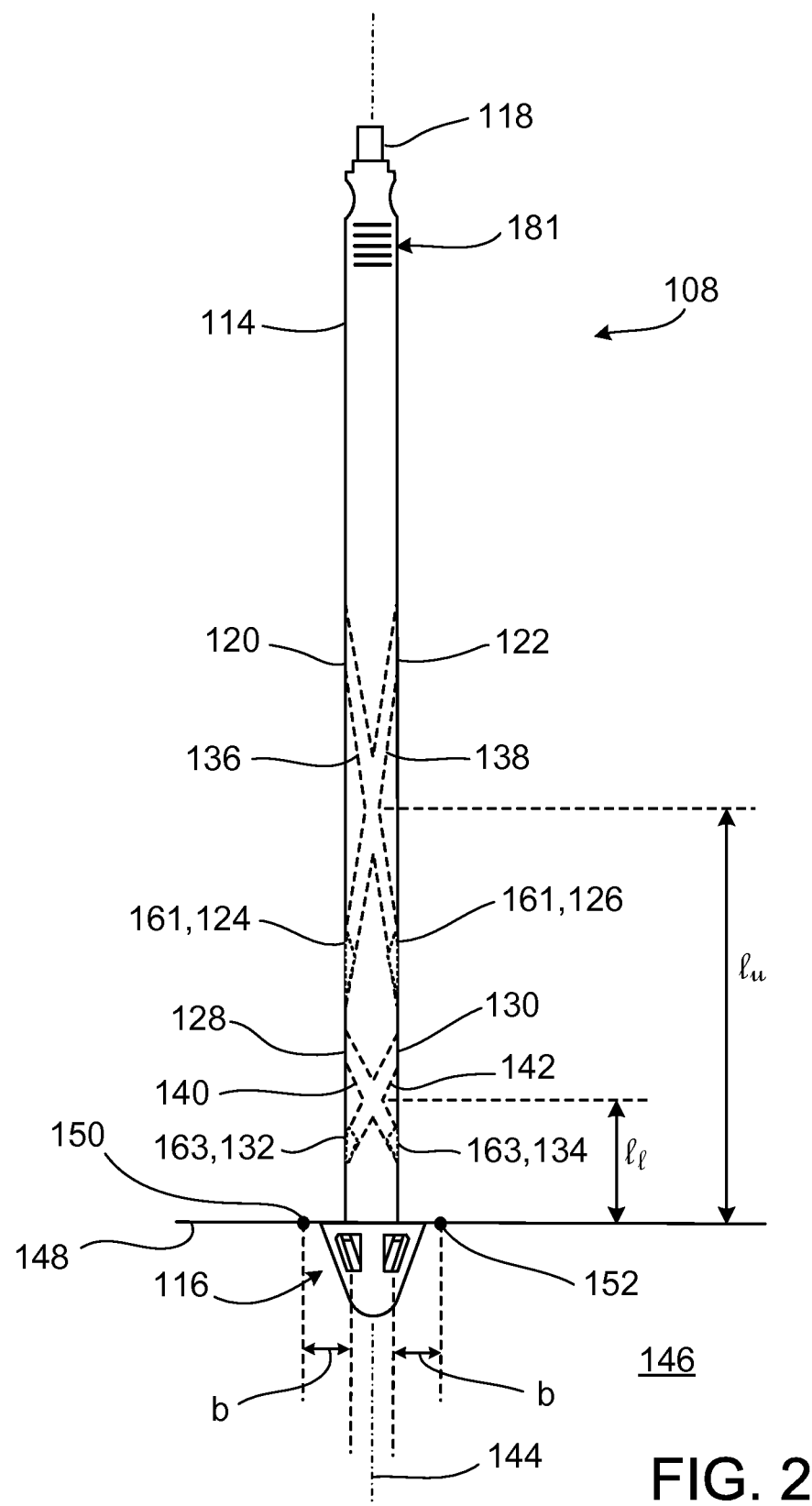
FIG. 2 is a front view of the suture passer guide of FIG. 1.

Referring to both FIGS. 1 and 2, the elongate tubular member 114 of the suture passer guide 108 includes a sidewall defining eight openings 120, 122, 124, 126, 128, 130, 132, 134 that can be aligned with channels 172, 174 formed in an inner shaft 168 (shown in FIG. 4) disposed in a central lumen of the elongate member 114 to form four guide passages 136, 138, 140, 142. Referring particularly to FIG. 2, the upper guide passage 136 extends from the upper left proximal opening 120 to the right left distal opening 126, and the upper guide passage 138 extends from the upper right proximal opening 122 to the upper left distal opening 124. Similarly, the lower guide passage 140 extends from the lower left proximal opening 128 to the lower right distal opening 134, and the lower guide passage 142 extends from the lower right proximal opening 130 to the lower left distal opening 132. Each of the guide passages 136, 138, 140, 142 extends at an acute angle relative to the longitudinal axis 144 of the elongate member 114. The guide passages 136, 138, 140, 142 are sized to receive a suture passer to be used with the suture passer guide 108.

The distances $l_u$, $l_l$ at which the guide passages 136, 138, 140, 142 are located (as measured to centroids of the guide passages) from the proximal tissue contacting surface of the expanded expandable member 116 and the angles at which the guide passages 136, 138, 140, 142 extend from the proximal openings 120, 122, 128, 130, respectively, can be selected based on the desired bite to be provided by the suture. The combination of these distances $l_u$, $l_l$ and angles of the guide passages 136, 138, 140, 142 determines the locations at which the suture passer punctures the inner lining of a surgical cavity (represented by line 148 in FIG. 2) and thus dictates the bite achieved by sutures positioned in the tissue by passing a suture passer loaded with the suture through the guide passages. The points at which the suture passer punctures the lining 148 of the surgical cavity are denoted as a left puncture 150 and a right puncture 152, and distances b between the left puncture 150 and the sidewall of the elongate member 114 and between the right puncture 152 and the sidewall of the elongate member 114 represent the respective suture bites to be achieved.

The upper guide passages 136, 138 typically extend at substantially equal angles relative to the longitudinal axis 144. Similarly, the lower guide passages 140, 142 typically extend at substantially equal angles relative to the longitudinal axis 144. These geometries facilitate passing the suture passer through the surgical cavity wall on each side of the wound at approximately the same angle and thus help to ensure that the suture bite is approximately equally distributed on both sides of the wound. An equal bite distribution can improve the quality of the wound repair and reduce the time required for the wound to heal.

Typically, the guide passages 136, 138, 140, 142 extend through the suture passer guide 108 at angles that deliver the suture passer to punctures 150, 152 that are laterally spaced approximately 0.5 to about 2.0 cm (e.g., 1 cm) from the sidewall of the elongate member 114 (i.e., b≈0.5 to 2.0 (e.g., 1 cm)). Accordingly, the upper guide passages 136, 138 extend from the proximal openings 120, 122, respectively, at an angle different than the lower guide passages 140, 142 extend from the proximal openings 128, 130, respectively, such that inserting the suture passer through either the upper guide passage 136 or the lower guide passage 140 delivers the suture passer to the same right puncture 152 and inserting the suture passer through either the upper guide passage 138 or the lower guide passage 142 delivers the suture passer to the same left puncture 150. As will be described below, the expandable member 116 is expanded and pulled against the inner lining of the surgical cavity during use to ensure that the guide passages 136, 138, 140, 142 are located at known distances from the inner lining of the surgical cavity regardless of the overall thickness of the patient's tissue. Because the guide passages 136, 138, 140, 142 are positioned at generally the same distances from the lining of the surgical cavity from patient to patient (i.e., regardless of the varying thickness of tissue from patient to patient), the suture passer exit points (i.e., punctures 150, 152) will be substantially the same regardless of the thickness of the patient's tissue.

The surgeon can decide whether to use upper guide passages 136, 138 or the lower guide passages 140, 142 by determining which of those passages provides the best suture passer entry point along the thickness of the tissue. The upper guide passages 136, 138 will typically be used for patients having a tissue thickness that exceeds a certain threshold (e.g., 5.0 cm), while the lower guide passages 140, 142 will typically be used for patients having a tissue thickness that falls below the threshold. For example, the lower guide passages 140, 142 can be configured to enable suturing of a wound within a surgical cavity wall having a thickness in an approximate range of 2.5-5.0 cm, while the upper guide passages 136, 138 can be configured to enable suturing of a wound within a surgical cavity wall having a thickness in an approximate range of 5.0-12 cm. Thus, in many cases, having two different sets of guide passages 136, 138 and 140, 142, respectively, enables the suture passer guide 108 to be used for obtaining the desired suture bite in patients having a variety of surgical wall thicknesses.

In some embodiments, the distances $l_u$, $l_l$ at which the guide passages 136, 138, 140, 142 are located (as measured to centroids of the guide passages) from the proximal tissue contacting surface of the expanded expandable member 116 are about 5.0 cm to about 12 cm and about 1.0 cm to about 4.0 cm, respectively. In addition, the angles at which the upper guide passages 136, 138 and the lower guide passages 140, 142 extend relative to the longitudinal axis 144 of the elongate member 114 can be about 5.0 degrees to about 30 degrees and about 15 degrees to about 45 degrees, respectively.

Figure 3:
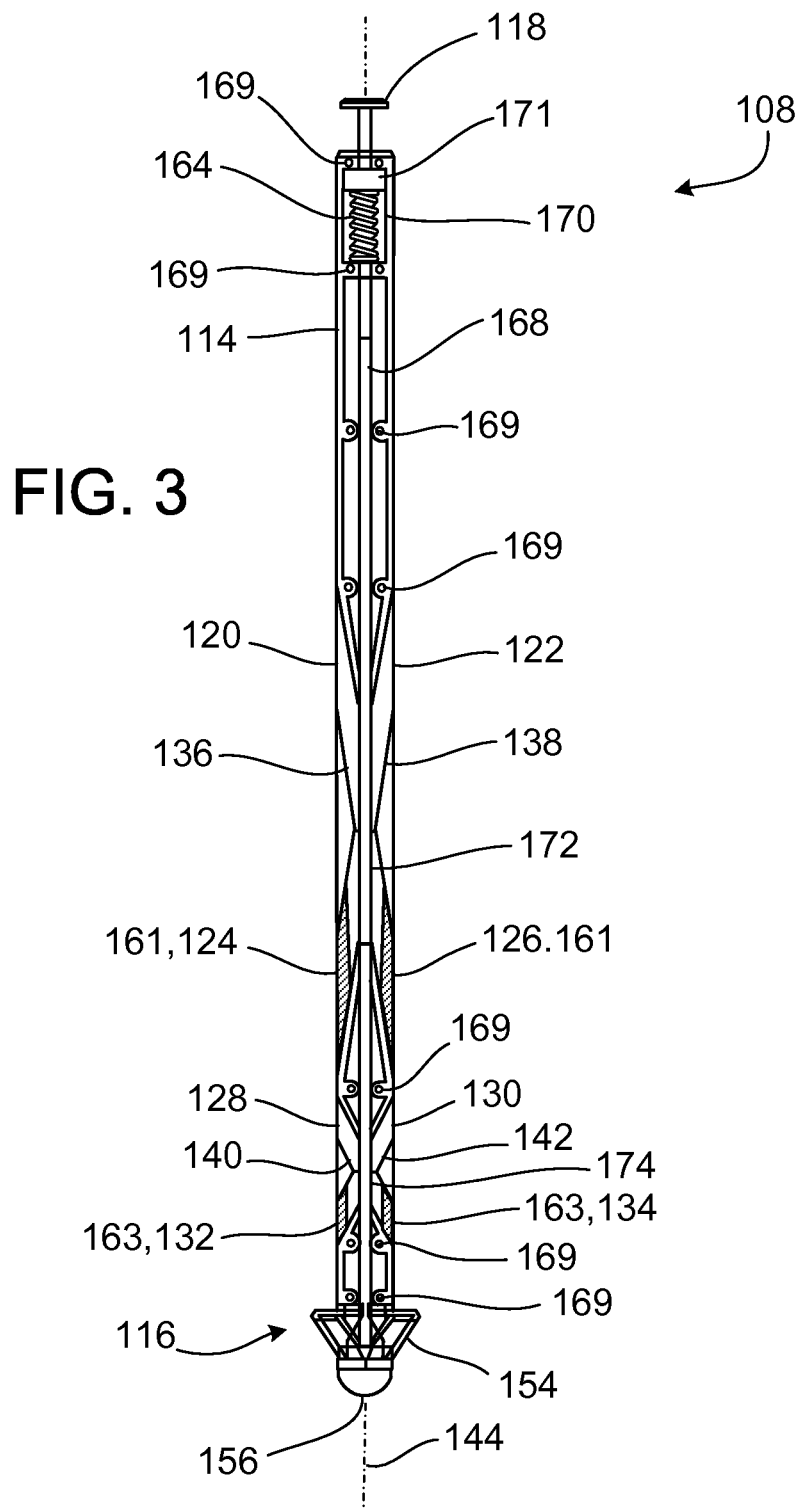
FIG. 3 is a cross-sectional view of the suture passer guide of FIG. 1.
Figure 4:
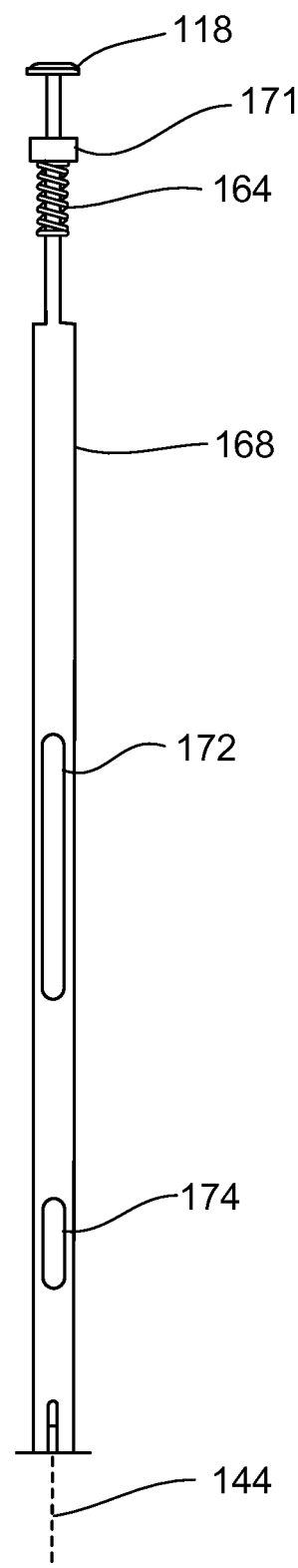
FIG. 4 is a side view of an inner shaft assembly of the suture passer guide of FIG. 1 that can be used to expand and collapse the expandable member disposed at the distal end region of the suture passer guide.

Referring to FIGS. 3 and 4, a thumb button 118 is secured to the proximal end of the inner shaft 168 that extends through the central lumen of the elongate member 114. The thumb button 118 can be depressed by the user to move the inner shaft 168 longitudinally with respect to the elongate member 114. The elongate member 114 includes multiple annular projections 169 that extend radially inward into the central lumen of the elongate member 114. Each of the annular projections 169 includes an o-ring that protrudes radially inwardly from the projection 169 and contacts the outer surface of the inner shaft 168. The o-rings create a substantially fluid-tight seal with the inner shaft 168 while allowing the inner shaft 168 to move along the longitudinal axis 144 relative to the elongate member 114.

Still referring to FIGS. 3 and 4, an annular shoulder 171 is secured to a proximal region of the inner shaft 168 and is disposed in a chamber 170 formed between the two most proximal annular projections 169. A spring 164 is also positioned in the chamber 170 between the annular shoulder 171 and the annular projection 169 that forms the distal end surface of the chamber 170. The spring 164 applies a proximal force to the annular shoulder 171 and thus biases the inner shaft 168 to the proximal position shown in FIG. 3.

Referring particularly to FIG. 3, a rounded base or tip 156 of the expandable member 116 is secured to the distal end region of the inner shaft 168. As will be described in greater detail below, a proximal end region of the expandable member 116 is secured to a distal end region of the elongate member 114. As a result of this configuration, when the inner shaft 168 is in the proximal position shown in FIG. 3, the expandable member 116 is radially expanded. When the user depresses the thumb button 118 with sufficient force to overcome the proximal resistance provided by the spring 164, the inner shaft 168 will move distally. The inner shaft 168 can be moved distally until the spring 164 is fully compressed between the annular shoulder 171 and the annular projection 169 that forms the distal end of the chamber 170. This distal movement of the inner shaft 168 can be used to move the expandable member 116 from its expanded position to a collapsed position, as will be described in greater detail below.

The thumb button 118, the annular shoulder 171, and the rounded base 156 can be secured to the inner shaft 168 using any of various techniques that result in these components being axially fixed relative to the inner shaft 168. For example, the thumb button 118, the annular shoulder 171, and the rounded base 156 can be thermally bonded, adhesively bonded, or mechanically secured to the inner shaft 168. Alternatively, the thumb button 118, the annular shoulder 171, and the rounded base 156 can be integrally molded or cast with the inner shaft 168.

Figure 5:
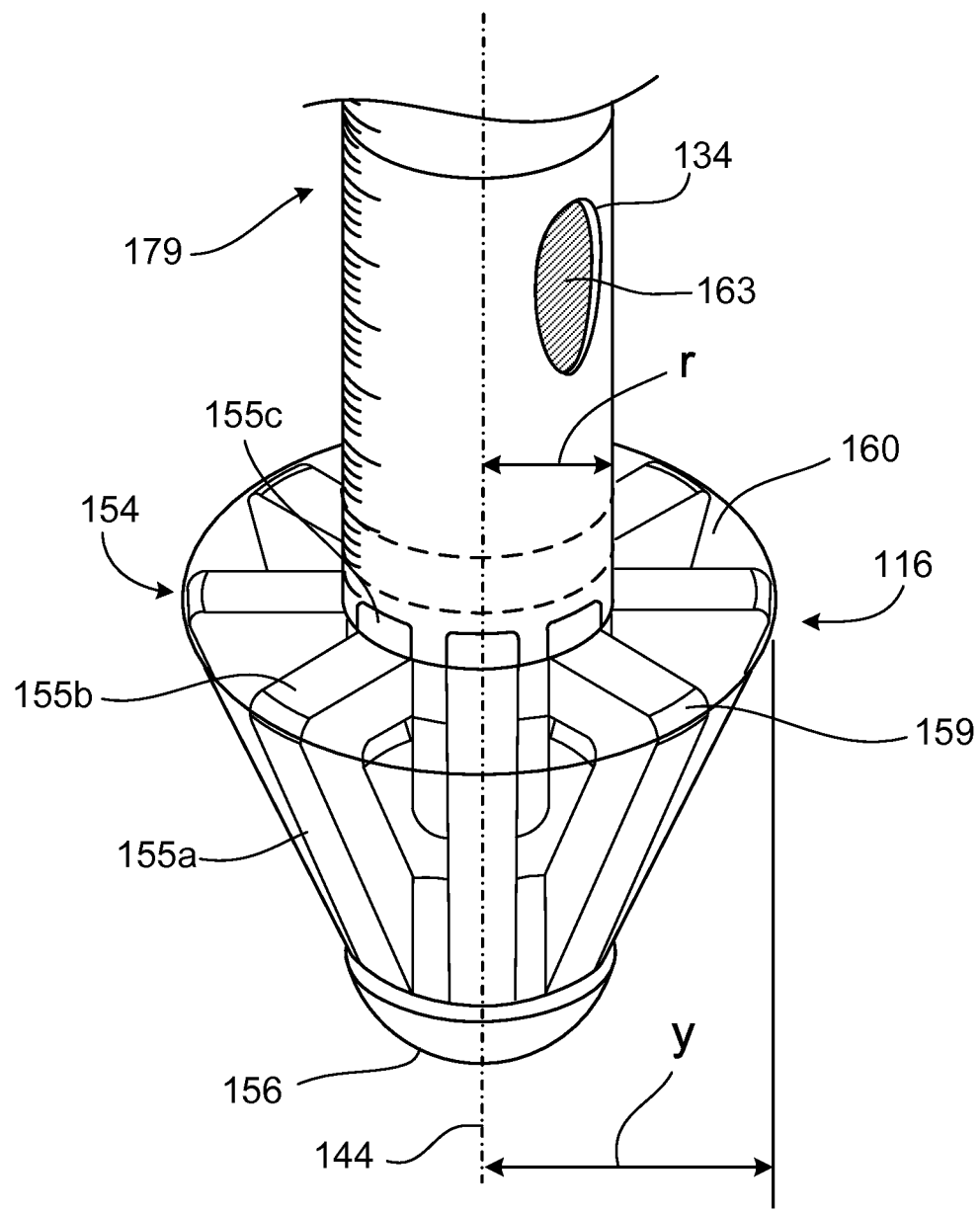
FIG. 5 is an enlarged, perspective view of the distal end region of the suture passer guide of FIG. 1, showing the expandable member in an expanded configuration.

Referring now to FIG. 5, which is an enlarged perspective view of the distal end region of the suture passer guide 108, the expandable member 116 includes eight collapsible arms 154. Each collapsible arm 154 includes a distal segment 155a, a middle segment 155b, and a proximal segment 155c that are coupled to one another via living hinges (e.g., thinned regions of the segments 155a-c). The proximal segment 155c of each collapsible arm 154 is secured to the elongate member 114. The proximal segment 155c can, for example, be thermally bonded, adhesively bonded, or mechanically secured to the inner shaft 168. The distal segment 155a of each collapsible arm 154 is secured to the rounded base 156. Typically, the distal segment 155a of the collapsible arm 154 and the rounded base 158 are integrally molded with one another. The collapsible arm 154 includes a thinned region in the distal segment 155a to form a living hinge 158 (shown in FIG. 6). Similarly, the collapsible arm 154 includes thinned regions between the distal segment 155a and the middle segment 155b and between the middle segment 155b and the proximal segment 155a to form living hinges 159 and 165, respectively (shown in FIG. 6). The collapsible arms 154 are spaced approximately equidistantly from the longitudinal axis 144 of the elongate member 114 and are configured to collapse from an expanded configuration (shown in FIGS. 5 and 6) to a collapsed configuration (shown in FIG. 7).

Figure 6:
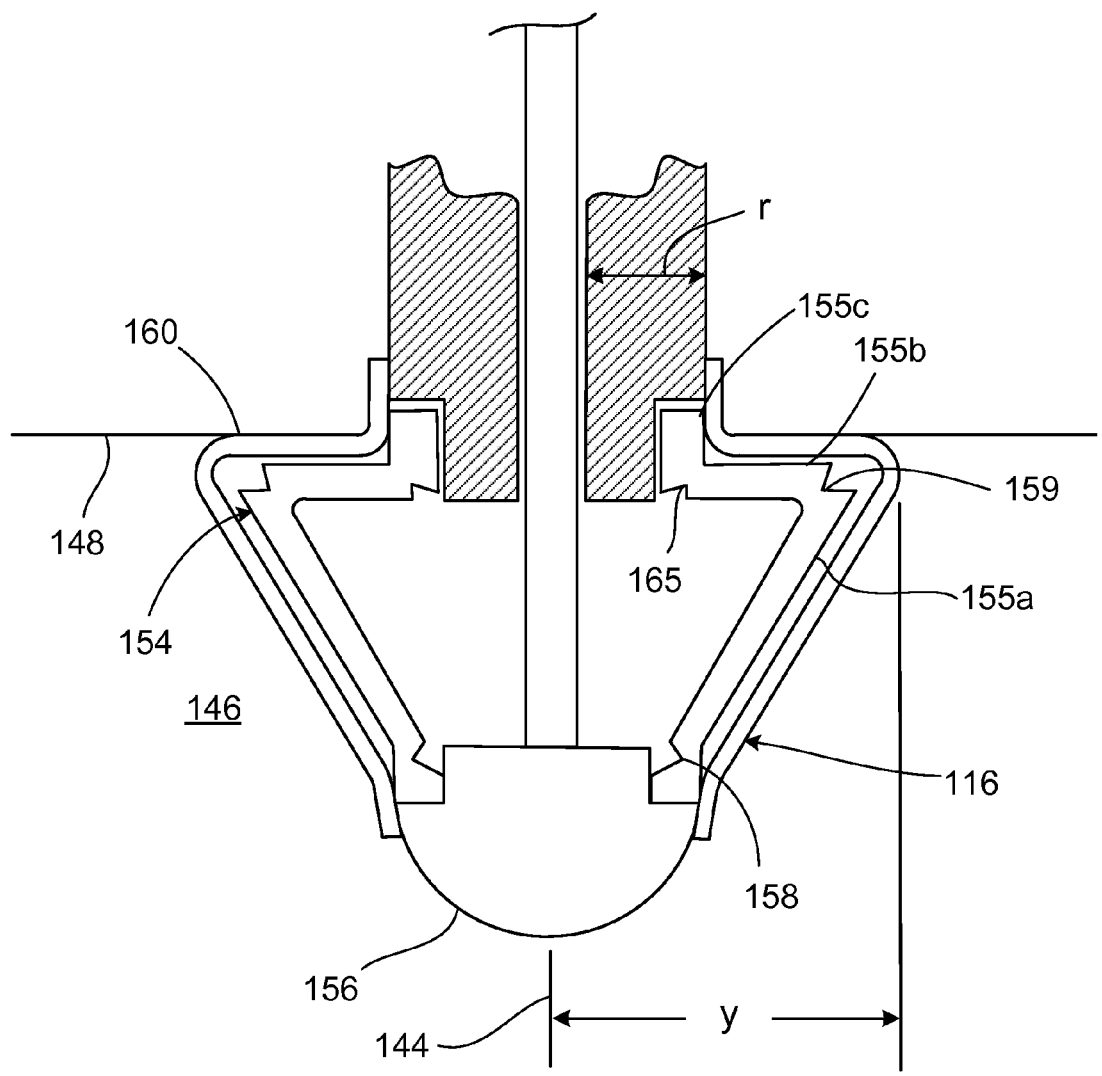
FIG. 6 is a cross-sectional view of the distal end region of the suture passer guide of FIG. 1, showing the expandable member in an expanded configuration.
Figure 7:
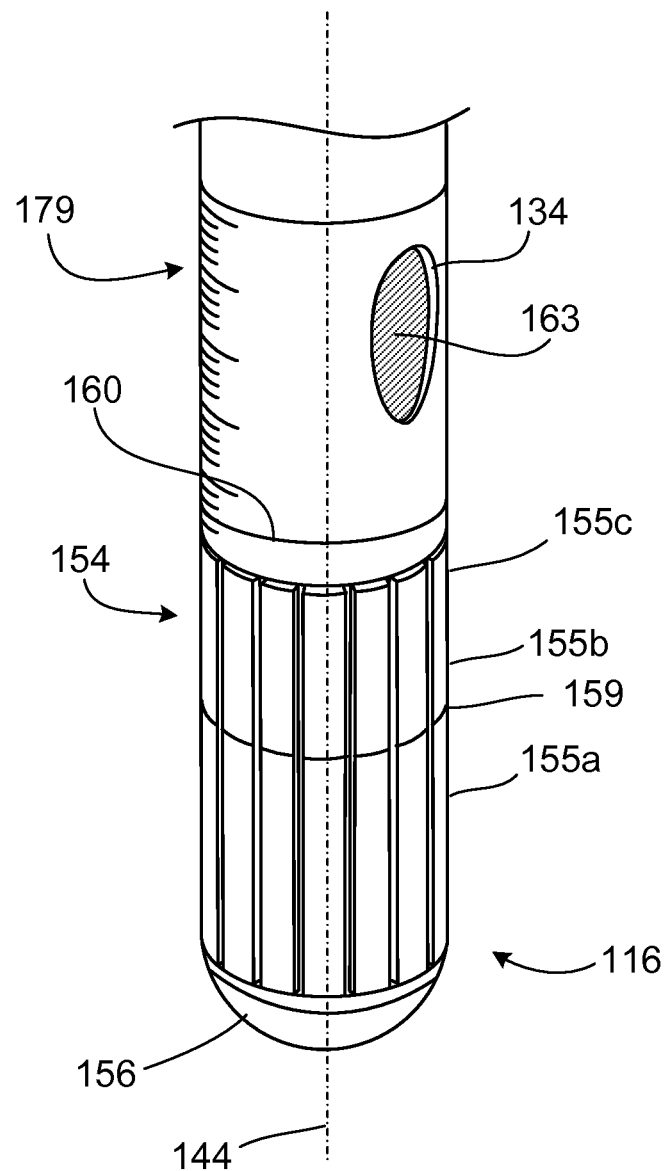
FIG. 7 is a perspective view of the distal end region of the suture passer guide of FIG. 1, showing the expandable member in a collapsed configuration.

As shown in FIGS. 5 and 6, when the collapsible arms 154 are in the expanded configuration, the collapsible arms 154 extend radially a distance y substantially equidistant from the longitudinal axis 144 and greater than an outer radius r of the elongate member 114. As shown in FIG. 7, in the collapsed configuration, the collapsible arms 154 are substantially flush with the sidewall of the elongate member 114 and thus do not extend substantially past an outer radius r of the elongate member 114. The external surfaces of the collapsible arms 154 are substantially smooth to reduce the likelihood of the collapsible arms 154 tearing or otherwise damaging an inner lining of a surgical wall when the proximal arm segments 155c of the expanded expandable member 116 are brought into contact with the inner lining of the surgical wall.

Referring to FIGS. 3 and 5-7, when the thumb button 118 is depressed and the rounded base 156 of the expandable member 116 moves distally, the collapsible arms 154 of the expandable member 116 collapse from the expanded configuration (shown in FIGS. 3, 5, and 6) towards the longitudinal axis 144 and into the collapsed configuration (shown in FIG. 7). In the collapsed configuration, the collapsible arms 154 are substantially flush with the sidewall of the elongate member 114 such that the expandable member 116 can fit within the central lumen 106 of the endoscopic port 102 to pass the suture passer guide 108 through the endoscopic port 102. The expanded configuration enables the expanded expandable member 116 of the suture passer guide 108 to be positioned against the inner lining of a surgical cavity without the suture passer guide 108 sliding up through the port site wound. Because the inner shaft 168 is biased to a proximal position by the spring 164, the expandable member 116 is biased to the expanded configuration. As a result, with the thumb button 118 released, the expandable member 116 can automatically expand as it is passed into the surgical cavity via the endoscopic port 102.

As shown in FIGS. 5-7, an elastic film 160 surrounds the expandable member 116. A proximal end region of the film 160 is attached to a distal end region of the elongate member 114 and a distal end region of the film 160 is attached to the rounded base 156 with an adhesive. The elastic film 160 can be formed of any of various materials that can stretch with the expandable member 116 as the expandable member 116 is expanded. It can also be beneficial to use a resilient material that substantially returns to its original size and shape when the expandable member 116 is collapsed. The elastic film 160 may, for example, be made of silicone and can have a thickness of 0.005 to 0.010 in. The elastic film 160 has a smooth surface that directly contacts the inner lining of the surgical wall during use. Thus, the film 160 can help to reduce the risk of tearing or otherwise damaging the lining during a procedure. In addition, the film 160 can be substantially gas impermeable and can help to ensure that gases, such as carbon dioxide ($CO_2$), within the surgical cavity do not escape from the surgical cavity through openings between the collapsible arms 154 of the expandable member 116. Thus, the elastic film 160 can help to prevent loss of inflation pressure within the surgical cavity (e.g., loss of pneumoperitoneum within an abdominal cavity) during use of the suture passer guide 108.

As shown in FIGS. 1-3, 5, and 7, the suture passer guide 108 also includes self-sealing elastic plugs 161 disposed within the upper distal openings 124, 126 and self-sealing elastic plugs 163 disposed within the lower distal openings 132, 134. When the suture passer is passed through the guide passage 136 and exits the distal opening 126 that is plugged with the elastic plug 161, for example, the suture passer punctures the elastic plug 161. As the suture passer is inserted through the elastic plug 161, the elastic plug 161 seals itself around the surface of the suture passer. Following removal of the suture passer from the elastic plug 161, the elastic plug 161 seals the hole in which the suture passer was disposed. The inclusion of the elastic plugs 161, 163 within the distal openings 124, 126, 132, 134 and the self-sealing properties of the elastic plugs 161, 163 can prevent loss of inflation pressure within the surgical cavity (e.g., loss of pneumoperitoneum within the abdominal cavity) during use of the suture passer guide 108, such that the surgical cavity does not need to be re-insufflated following use of the suture passer guide 108. The elastic plugs are typically made of silicone or polyphenol ether (PPE). However, other self-sealing materials can alternatively or additionally be used.

Referring briefly again to FIG. 1, the suture passer guide 108 further includes an upper colored band 176 and a lower colored band 178 on the external surface of the elongate member 114 and surrounding the upper proximal openings 120, 122 and the lower proximal openings 128, 130, respectively. The colored bands 176, 178 can assist the user in selecting which of the guide passages 136, 138, 140, 142 to use for a particular procedure. Each band 176, 178 is of a different color. When the expanded expandable member 116 of the suture passer guide 108 is pulled against the inner lining of a surgical cavity wall and only the colored band 176 is visible outside of the patient, this indicates to the surgeon that the suture passer should be inserted into the upper proximal openings 120, 122 and passed through the upper guide passages 136, 138. In contrast, when the expanded expandable member 116 of the suture passer guide 108 is pulled against the inner lining of a surgical cavity wall and both the colored band 176 and the colored band 178 are visible outside of the patient, this indicates to the surgeon that the suture passer should be inserted into the lower proximal openings 128, 130 and passed through the lower guide passages 140, 142. The colored bands 176, 178 can be positioned along the suture passer guide 108 so that only the upper colored band 176 is visible when the surgical cavity wall has a thickness of 5.0-12.0 cm, and the lower colored band 178 is visible when the surgical cavity wall has a thickness of 2.5-5.0 cm. A desirable thickness of tissue (e.g., a desirable thickness of fascia) will be sutured when the appropriate guide passages 136, 138, 140, 142 are selected and used. In addition to using the colored bands 176, 178 to determine which of the guide passages 136, 138, 140, 142 should be used for a particular patient, a surgeon can also quickly and easily approximate the surgical cavity wall thickness based on the position of the colored bands 176, 178 relative to the outer surface of the surgical cavity wall.

As shown in FIGS. 1, 5, and 7, the suture passer guide 108 further includes a set of ruler markings 179 disposed on the external surface of the elongate member 114 that increase in value from the distal end of the elongate member 114. While the expandable member 116 is expanded and positioned along the lining of the surgical cavity wall, the ruler markings 179 serve to indicate a thickness of the surgical cavity wall, which may be recorded in a patient chart for prognostication or potential statistical analyses.

As shown in FIG. 1, the suture passer guide 108 also includes multiple etched rings 181 formed on the external surface of the elongate member 114 near the proximal end of the elongate member 114. The etched rings 181 provide the proximal end region of the suture passer guide 108 with added grip to make it easier for the surgeon to grasp the suture passer guide 108 and insert it into the endoscopic port 102. As an alternative to or in addition to etched rings 181, the proximal end region of the elongate member 114 can include other types of textured surfaces that improve the ability of the surgeon to grip the suture passer guide 108. Such textured surfaces can be particularly beneficial when the surgeon's gloves are wet or otherwise lubricated.

The suture passer guide 108, as explained above, has a length that is sufficient to allow the expandable member 116 to extend distally beyond the endoscopic port 102 while the proximal end region of the suture passer guide 108 including the thumb button 118 remains proximal to the endoscopic port 102. The suture passer guide 108 typically has a length of about 8.0 to about 12.0 in (e.g., 8.5 in.). Typically, the suture passer guide 108 (e.g., the elongate member 114 of the suture passer guide 108) has a diameter of about 5 to about 15 mm. It should be understood, however, that the suture passer guide 108 can have different dimensions, depending on the size of the endoscopic port 102 with which it is to be used.

The various components of the suture passer guide 108, including the elongate member 114, the expandable member 116, and the inner shaft 168, can be formed of one or more of a variety medical grade materials, including stainless steel, titanium, polycarbonate, Acrylonitrile butadiene styrene (ABS), polypropylene, acrylic, liquid crystal polymer (LCP), polyetheretherketone (PEEK), silicone, and thermoplastic elastomer (TPE).

The endoscopic port 102 typically includes one or more seals, such as o-rings (i.e., elastic, flat washer-shaped rings), that surround the elongate member 114 when the elongate member 114 is disposed within the central lumen 106 of the endoscopic port 102. The seals and the elongate member 114 are configured so that a substantially fluid-tight seal is formed between the inner surfaces of the seals and the outer surface of the elongate member 114. For example, the inner diameter for the seals of the endoscopic port 102, in their undeformed state, will typically be equal to or slightly less than the outer diameter of the elongate member 114. As a result, gases within a surgical cavity can be prevented from escaping through the central lumen 106 while the suture passer guide 108 is disposed within the central lumen 106 of the endoscopic port 102 and the distal end of the endoscopic port 102 is positioned in the surgical cavity.

Figure 8:
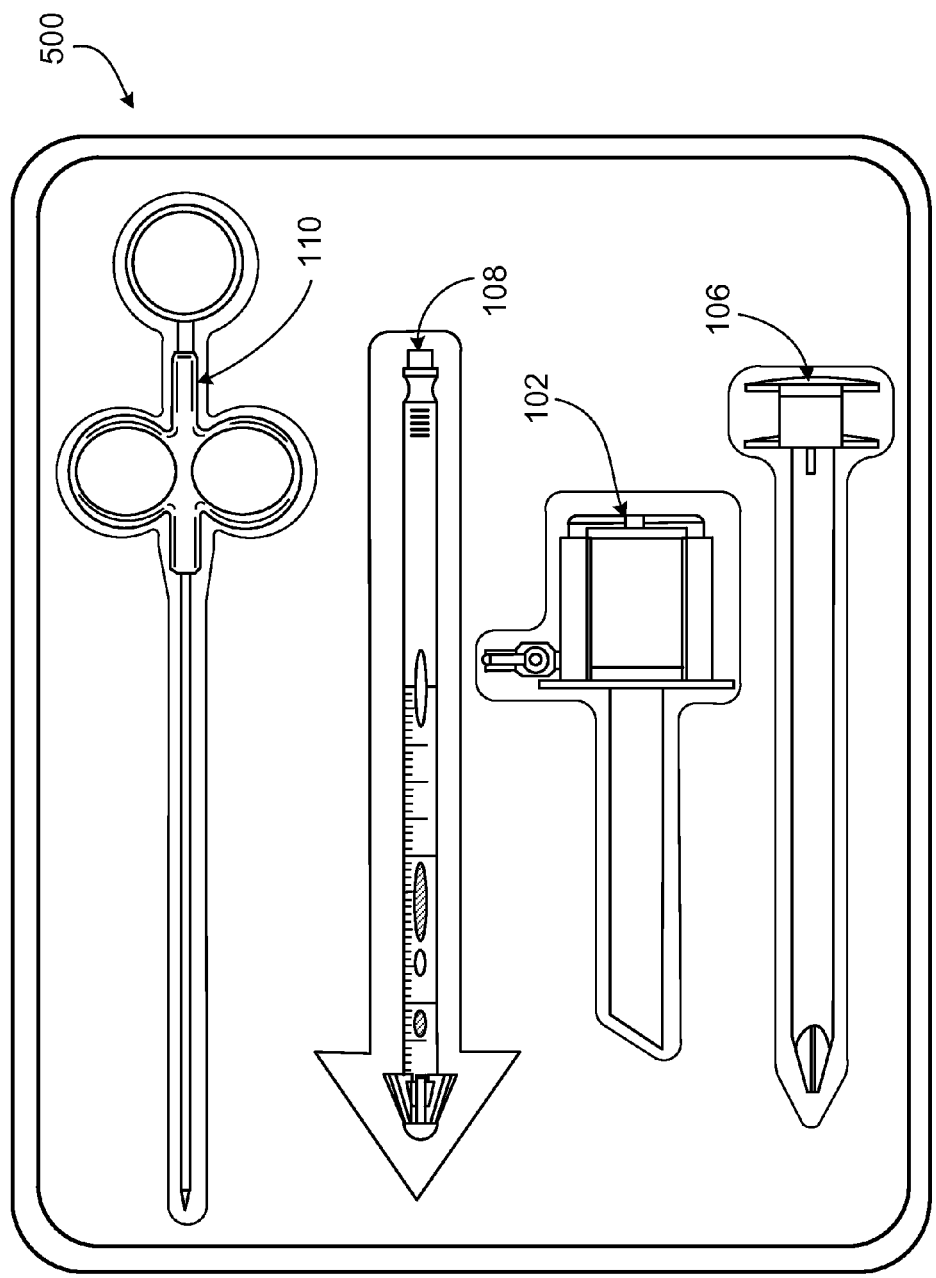
FIG. 8 illustrates an endoscopic surgical kit that includes an obturator, a suture passer, and the endoscopic port and suture passer guide of FIG. 1.

FIG. 8 illustrates an endoscopic surgical kit 500 that includes the endoscopic port 102, the suture passer guide 108, an obturator 104, and a suture passer 110.

Figure 9A:
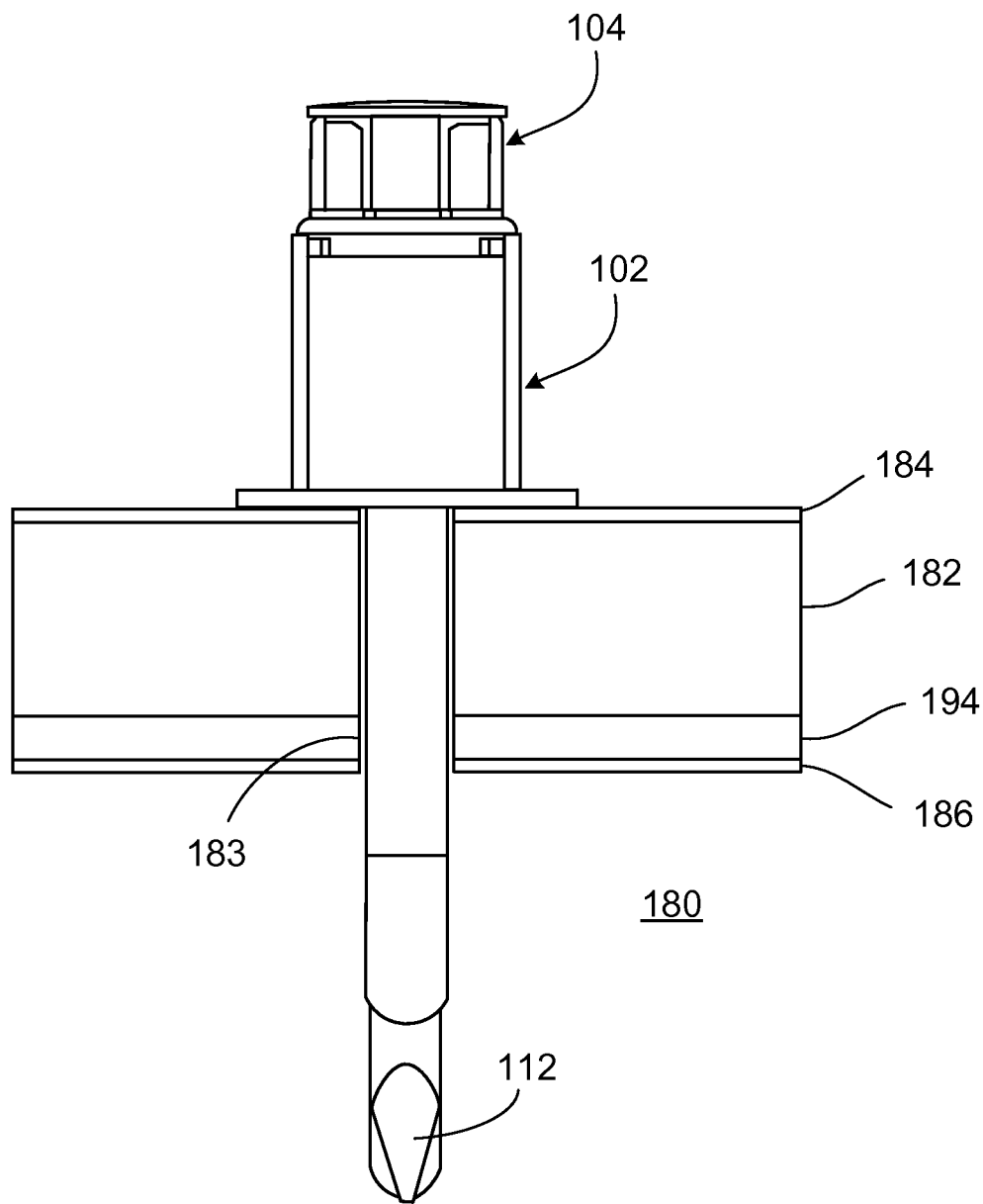
FIGS. 9A-9H schematically illustrate a method of performing a laparoscopic surgery and using the suture passer guide of FIG. 1 to repair an endoscopic port site wound.

FIGS. 9A-9H schematically illustrate a method of using the endoscopic surgical kit 500 to perform a laparoscopic surgical procedure in an abdominal cavity 180 of a patient and to repair an endoscopic port wound 183 used to access the patient's abdominal cavity 180. As shown in FIG. 9A, to perform the laparoscopic surgical procedure, the obturator 104 is positioned within the central lumen 106 of the endoscopic port 102 such that a sharp piercing tip 112 of the obturator 104 extends beyond a distal end of the endoscopic port 102. The endoscopic port 102 and the obturator 104 (often referred to in combination as a trocar) are then pushed through the abdominal wall of the patient, which includes an external skin layer 184, a relatively thick fatty layer 182, a fascia layer 194, and a peritoneum 186, until the tip 112 of the obturator 104 and the distal end of the endoscopic port 102 are positioned within the abdominal cavity 180 of the patient, thereby creating a port site wound 183 within the abdominal wall.

The obturator 104 is subsequently removed from the central lumen 106 of the endoscopic port 102, leaving the endoscopic port 102 positioned within the port site wound 183 and protruding into the abdominal cavity 180. Cameras and other surgical instruments are then inserted through the central lumen 106 for viewing internal organs and carrying out the surgical procedure within the abdominal cavity 180. The endoscopic port 102 includes seals that substantially prevent gases from escaping from the abdominal cavity 180 via the central lumen 106 of the endoscopic port 102 during the procedure. As a result, the inflation pressure (i.e., pneumoperitoneum) of the abdominal cavity 180 can be maintained while the endoscopic port 102 is positioned in the port site wound.

Figure 9B:
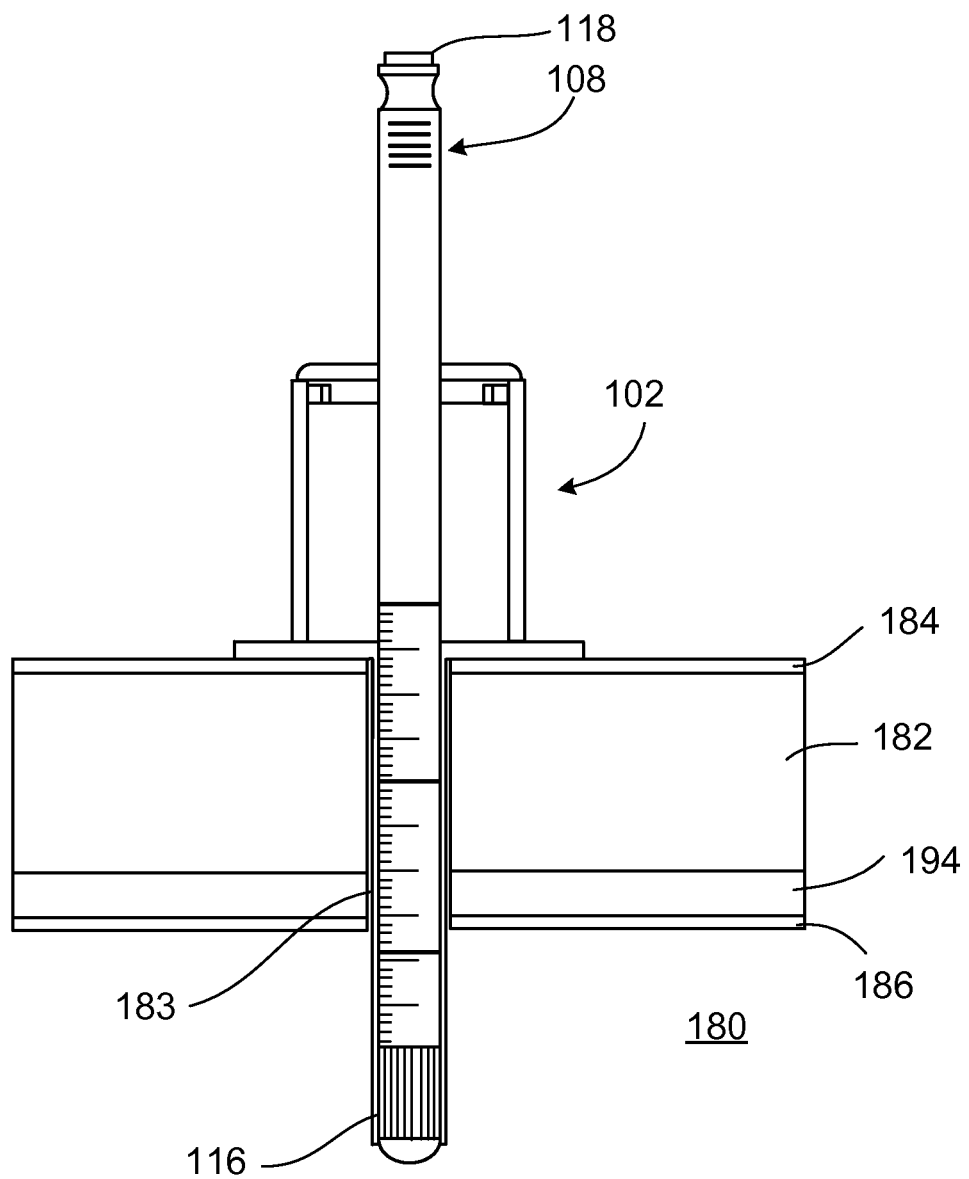

After completing the surgical procedure within the abdominal cavity 180, the suture passer guide 108 is inserted through the central lumen 106 of the endoscopic port 102 and into the abdominal cavity 180 in order to facilitate repair of the port site wound 183. As shown in FIG. 9B, to insert the suture passer guide 108 through the central lumen 106 of the endoscopic port 102, the thumb button 118 is first depressed to collapse the expandable member 116. The suture passer guide 108 is then inserted into the central lumen 106 of the endoscopic port 102. Once the collapsed expandable member 116 is positioned within the central lumen 106 of the endoscopic port 102, the button 118 can be released as the user continues to pass the suture passer guide 108 distally through the lumen 106 toward the abdominal cavity 180 of the patient. The sidewalls of the elongate member 114 retain the expandable member 116 in the collapsed configuration as the suture passer guide 108 is passed through the lumen 106.

Figure 9C:
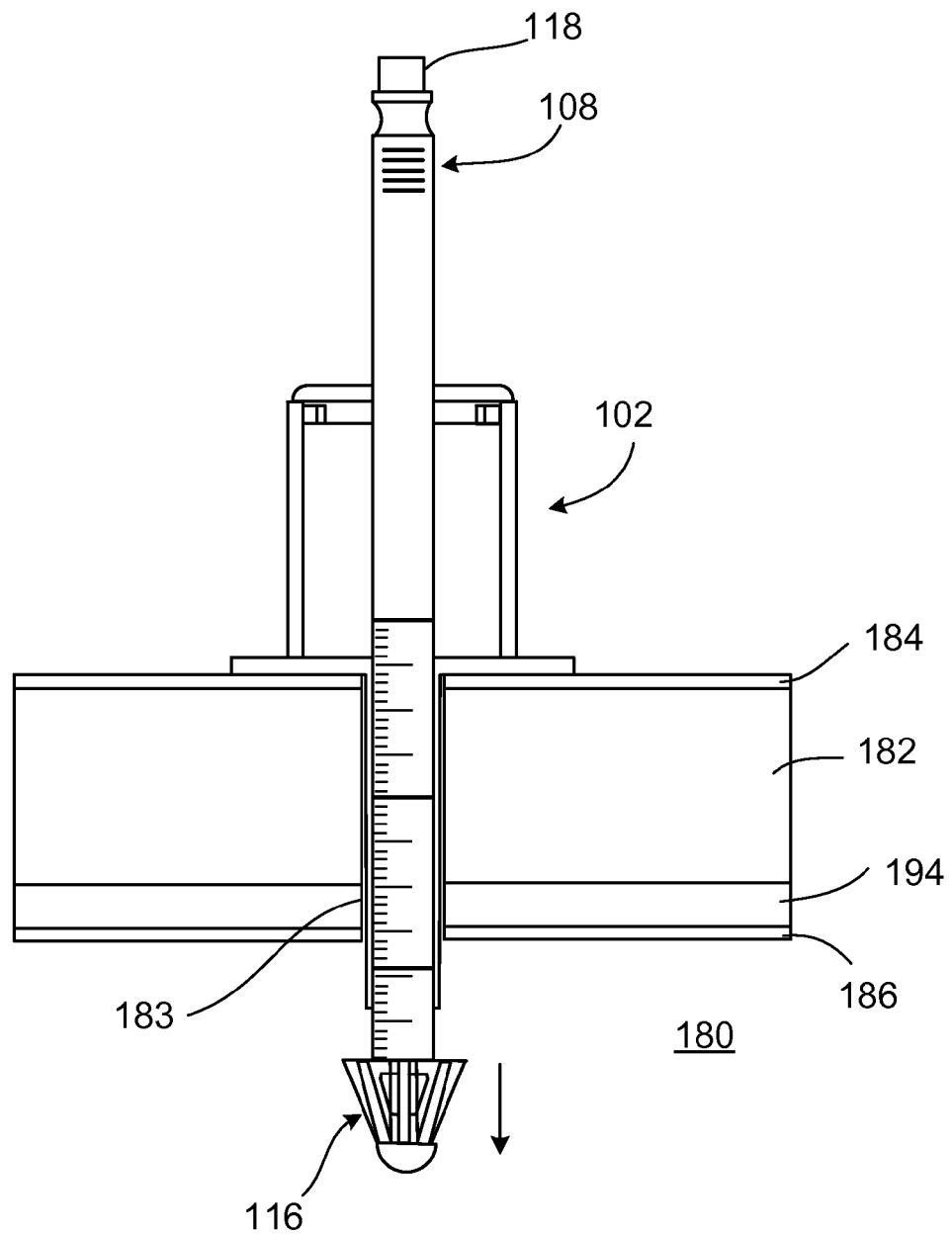

As shown in FIG. 9C, when the expandable member 116 is passed distally beyond the distal end of the endoscopic port 102, the expandable member 116 automatically expands. In this expanded configuration, the expandable member 116 has a diameter that exceeds the diameter of the endoscopic port 102 and the port site wound 183.

Figure 9D:
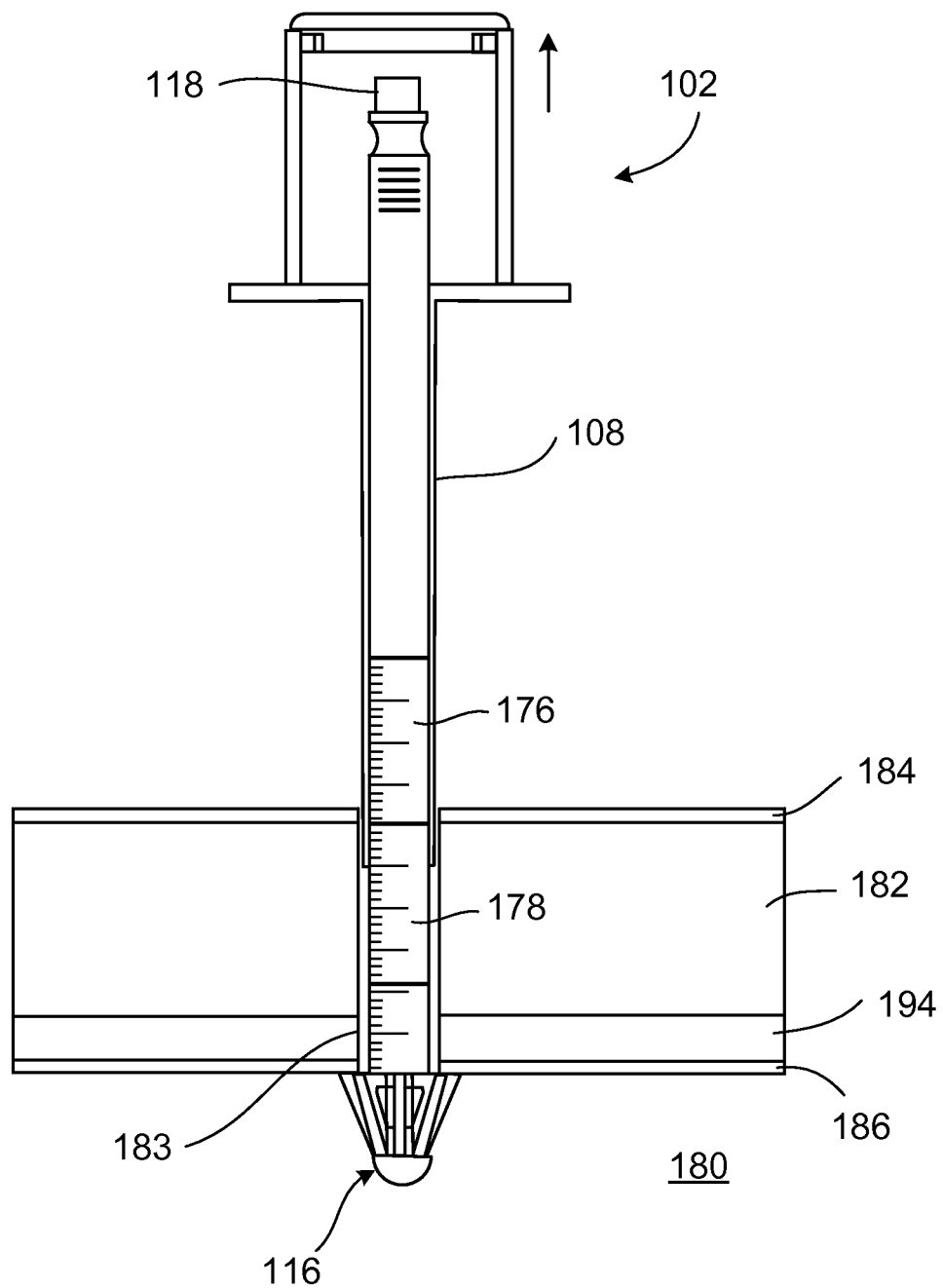

With the expandable member 116 in its expanded configuration, the endoscopic port 102 is then removed from the wound by pulling proximally on the proximal end region of the endoscopic port 102, as shown in FIG. 9D. As the endoscopic port 102 is removed from the port site wound, the expanded expandable member 116 contacts the inner lining of the patient's abdominal cavity (i.e., the patient's peritoneum 186), thereby preventing the suture passer guide 108 from being pulled out of the port site wound 183 along with the endoscopic port 102. Because the endoscopic port 102 is not vacated from the port site wound prior to positioning the suture passer guide 108 in the port site wound 183 and the abdominal cavity 180, the port site wound 183 is not left open in a manner that would allow it to freely release insufflation gases from the abdominal cavity 180.

After the endoscopic port 102 has been removed from the port site wound 183, the tissue surrounding the wound 183 collapses against the outer surface of the suture passer guide 108, creating a partial seal that inhibits insufflation gases (e.g., $CO_2$) within the abdominal cavity 180 from escaping through the port site wound such that the inflation pressure within the abdominal cavity 180 (i.e., the pneumoperitoneum within the abdominal cavity) is substantially maintained.

Figure 9E:
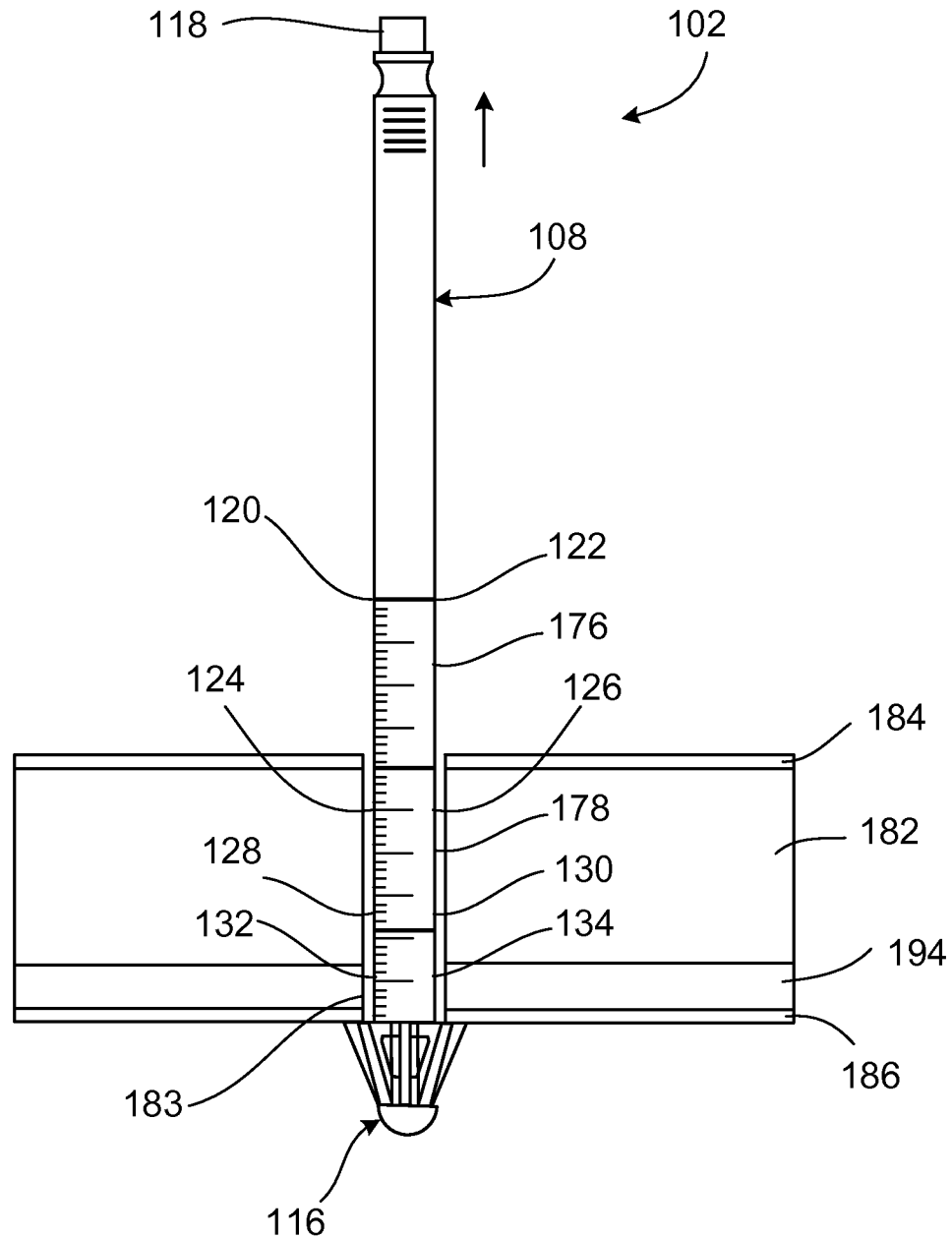

Referring to FIG. 9E, prior to inserting the suture passer 110 through the suture passer guide 108 to suture the port site wound 183, the user applies a proximal force to the suture passer guide 108 to ensure that the expanded expandable member 116 is in contact with the peritoneum 186. In this position, the distal openings 124, 126, 130, 132 of the guide passages 136, 138, 140, 142 are located at known distances from the peritoneum 186. Accordingly, positioning the expandable member 116 against the peritoneum 186 helps to position the suture passer guide 108 in the desired location within the wound 183 for optimal passage of the suture passer 110 and helps to ensure that the colored bands 176, 178 can be used by the surgeon to accurately determine which of the guide passages 136, 138, 140, 142 should be used for suturing the port site wound 183. In this case, the outer surface of the abdominal wall (i.e., the external skin layer 184) lies along the region of the colored band 176. Based on this, the surgeon quickly determines that the upper guide passages 136, 138 should be used for suturing the port site wound 183.

In addition to ensuring that the distal openings 124, 126, 132, 134 and the colored bands 176, 178 are located in the desired positions, the application of the proximal force to the suture passer guide 108 can also help to maintain the pneumoperitoneum within the abdominal cavity 180. In particular, the film 160 surrounding the expandable member 116 is pulled against the peritoneum 186, which can create a partial seal that helps to prevent $CO_2$ and other gases within the abdominal cavity 180 from escaping through the port site wound.

Figure 9F:
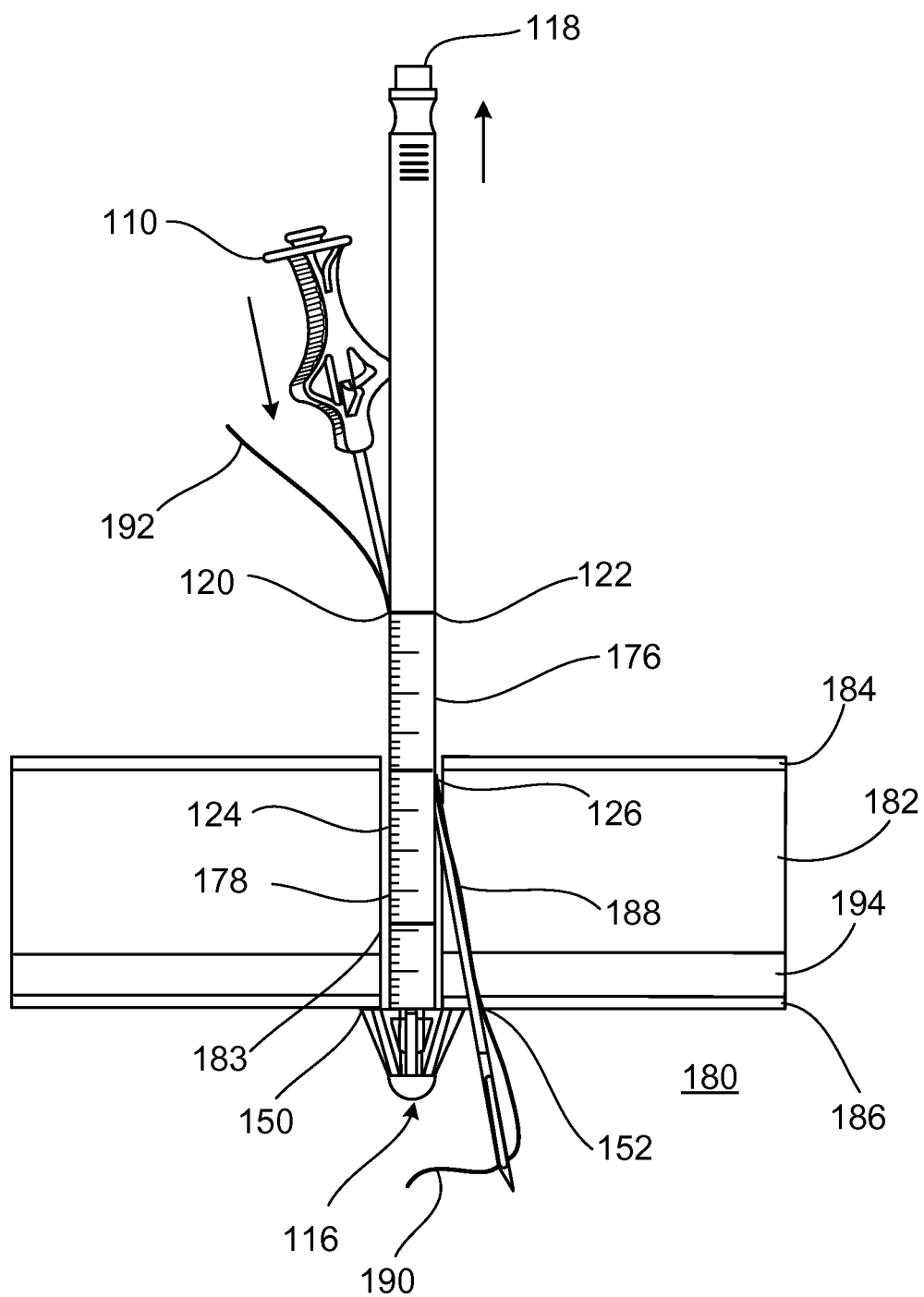

Referring now to FIG. 9F, the suture passer 110 is then loaded with a suture 188 and inserted into the upper left proximal opening 120, through the upper guide passage 136, and out of the upper right distal opening 126 such that the suture passer 110 punctures the peritoneum 186 at the right puncture point 152, which is laterally spaced from the expanded expandable member 116 (i.e., spaced from the expanded expandable member 116 in a direction that is perpendicular to the longitudinal axis of 144 of the elongate member 114). As a result, a first end 190 of the suture 188 is carried into the abdominal cavity 180 along with the distal end of the suture passer 110. Due to the geometry of the guide passage 136, the suture passer 110 remains laterally spaced from the expanded expandable member 116 as it passes along the length of the expanded expandable member 116. As a result, interference between the suture passer 110 and the expanded expandable member 116 is avoided.

As the suture passer 110 is delivered through the suture passer guide 108 and into the abdominal cavity 180, the surgeon applies a proximal force to the suture passer guide 108, which causes the expanded expandable member 116 to apply an outward force to the peritoneum 186. This outward force on the peritoneum 186 can make it easier to pass the tip of the suture passer 110 through the peritoneum 186 in a smooth manner. The self-sealing plug 161 disposed within the distal opening 126 forms a fluid-tight seal with the suture passer 110 and thus prevents any gases that might have entered the wound 183 from escaping to atmosphere via the guide passage 136. The suture 188 is sufficiently long that a second end 192 of the suture 188 remains external to the abdominal cavity 180. After depositing the first end 190 of the suture 188 in the abdominal cavity 180, the suture passer 110 is removed from the guide passage 136. Due to the resilience of the self-sealing plug 161 disposed within the distal opening 126, a fluid-tight seal is maintained once the suture passer 110 has been removed from the plug 161. Thus, any gases that might have entered the wound 183 are still prevented from escaping to atmosphere via the guide passage 136 by the plug 161. Insertion of the suture 188 into the abdominal cavity 180 in this manner is typically viewed via video generated by a camera inserted into the abdominal cavity 180 through another endoscopic port positioned within the abdominal wall.

Figure 9G:
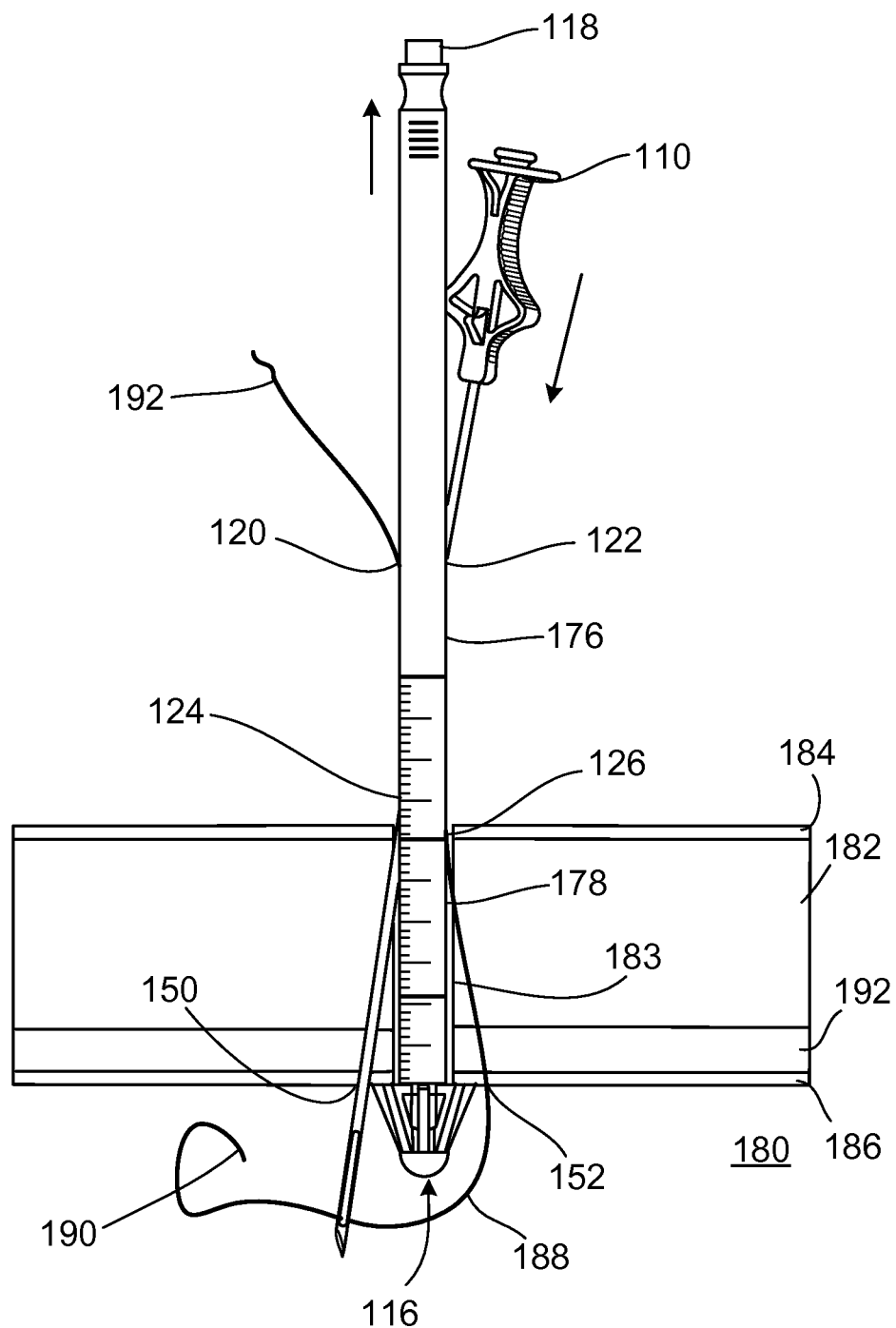

Referring to FIG. 9G, the suture passer 110 is then inserted into the upper right proximal opening 122, through the guide passage 138, and out of the upper left distal opening 124 such that the suture passer 110 punctures the peritoneum 186 at the left puncture point 150. The first end 190 of the suture 188 is then grasped with the suture passer 110. In some cases, prior to inserting the suture passer 110 into the upper right proximal opening 122, the suture passer guide 108 is tilted to more accurately guide the distal end of the suture passer 110 to a location within grasping proximity of the first end 190 of the suture 188. In some examples, the suture passer guide 108 is tilted about 20° to about 90° (e.g., about 30° to about 45°) relative to a longitudinal axis of the wound 183.

Figure 9H:
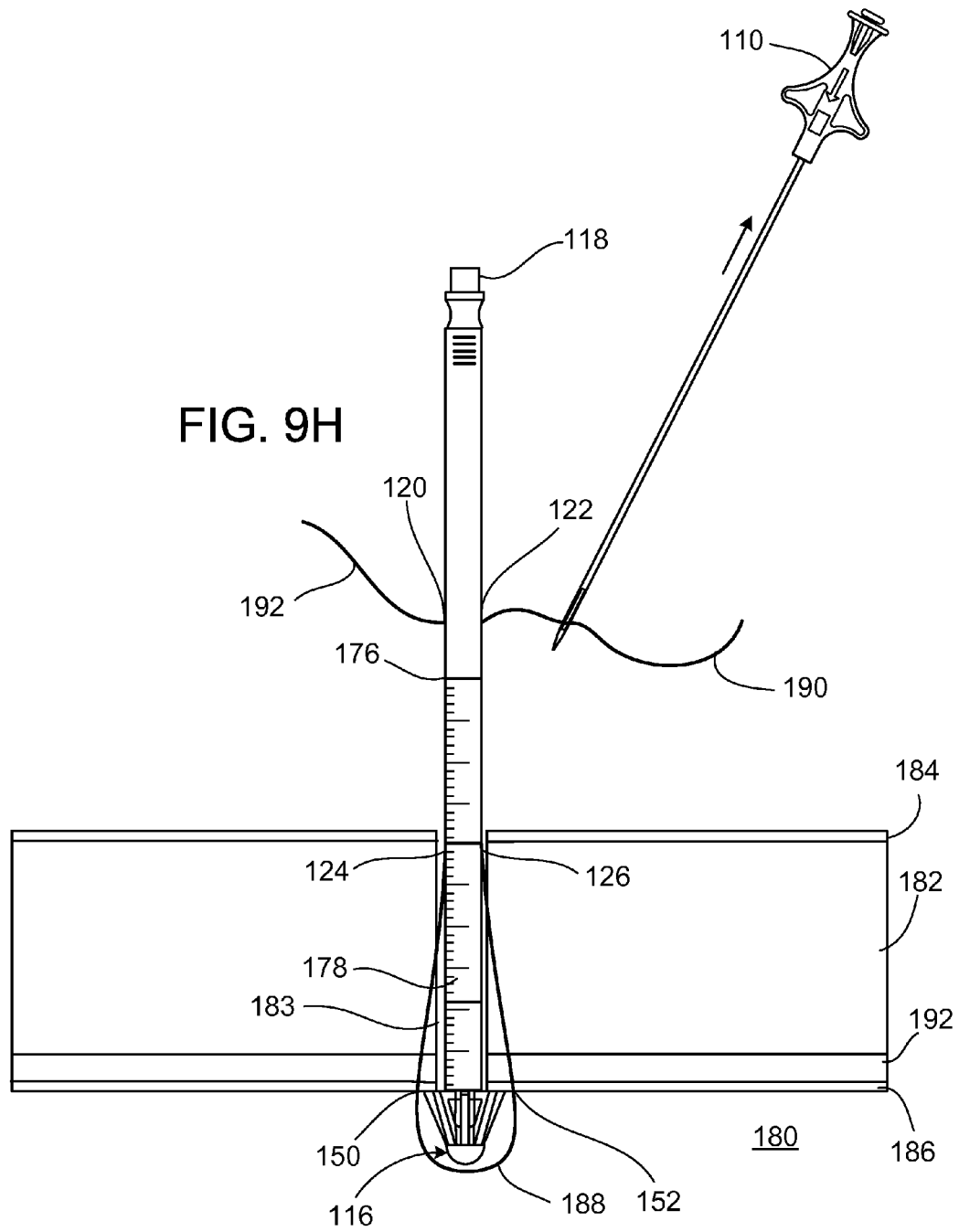

As shown in FIG. 9H, with the first end 190 of the suture 188 in its grasp, the suture passer 110 is then removed from the guide passage 138. As a result, the first end 190 of the suture 188 is pulled through the various tissue layers 186, 194, 182, 184 of the abdominal wall and outside of the patient. At this point, the first and second ends 190, 192 are both positioned outside of the patient.

With the suture 188 positioned within the tissue in this manner, the button 118 is again depressed to collapse the expandable member 116, and the suture passer guide 108 is pulled out of the port site wound 183. The smooth outer surfaces of the elongate member 114 and the collapsed expandable member 116 help to ensure that the tissue adjacent the port site wound 183 is not torn or otherwise damaged as the suture passer guide 108 is removed from the port site wound 183.

After removing the suture passer guide 108 from the port site wound 183, the first and second ends 190, 192 of the suture 188 are tied to form a knot. The knot is positioned at a location proximal to the fascia 194, such that the fascia 194 and peritoneum 186 are substantially closed. Due to the controlled placement of the suture 188 within the patient's tissue (e.g., the controlled suture bite) afforded by the use of the suture passer guide 108, the fascia 194 and peritoneum 186 are encompassed in a relatively smooth mass closure underneath the external skin layer 184 to produce a high quality port site wound repair.

Surgical procedures including the wound closure procedure described above can typically be carried out in less time than those that require the endoscopic port 102 to be removed before inserting a suture passer guide. For example, inserting the suture passer guide 108 through the endoscopic port 102 inhibits the loss of pneumoperitoneum and thus eliminates the time that might otherwise be required to re-insufflate the abdominal cavity following removal of the endoscopic port 102. Furthermore, inserting the suture passer guide 108 through the endoscopic port 102 removes the need to relocate the port site wound following removal of the endoscopic port 102, which is required when using a type of suture passer guide that is inserted directly into the port site wound. This also contributes to the reduced time required for such a procedure. In addition, by inserting the suture passer guide 108 through the endoscopic port 102, additional tissue damage that might otherwise result from inserting a suture passer guide directly into the wound can be avoided.

While the suture passer guide 108 has been described as including four guide passages 136, 138, 140, 142, in some embodiments, a suture passer guide may include a different number of guide passages. For example, in some embodiments, the suture passer guide includes a fifth and sixth guide passage extending from ninth and tenth proximal openings, respectively, such that the suture passer guide is adapted to suture surgical cavity walls having a thickness of less than 2.5 cm or more than 12.0 cm, depending on distances at which the six guide passages are located with respect to a distal end of an elongate member. In this embodiment, the shaft includes three channels accommodating extension of the six guide passages through the longitudinal axis 144 of the elongate member. The suture passer guide can further include three colored bands disposed on the external surface of the elongate member and surrounding the proximal holes defined by the sidewall of the elongate member, such that each colored band corresponds to one of three ranges of the abdominal wall thickness.

While the embodiments described above include only two guide passages within each region of the suture passer guide 108 (e.g., two upper guide passages that are circumferentially spaced by about 180 degrees and two lower guide passages that are circumferentially spaced by about 180 degrees), in certain embodiments, more than two passages (e.g., four passages, six passages, etc.) can be provided to allow the placement of more than one suture (e.g., two sutures, three sutures, etc.). Such an arrangement can be particularly useful for closing port site wounds created by large endoscopic ports (e.g., endoscopic ports having diameters of 15 mm or greater).

In certain embodiments, the suture passer guide includes only one upper guide passage and one lower guide passage extending between an upper proximal opening and a lower proximal opening, respectively. When using such a suture passer guide to facilitate the repair of port site wound, the suture passer guide is rotated 180 degrees following release of the suture 188 within the abdominal cavity 180 and removal of the suture passer 110 from the upper guide passage. The suture passer 110 is then reinserted through the upper proximal opening and the upper guide passage to grasp the first end 190 of the suture 188 and removed again from the upper guide passage such that the first end 190 of the suture 188 is disposed external to the abdominal cavity 180.

In certain embodiments, the suture passer guide includes only one guide passage. In such embodiments, differently configured suture passer guides would generally be used for patients of substantially different size (i.e., surgical wall thickness). The one passage suture passer would be rotated 180 degrees between placement of the suture into the surgical cavity and retrieval of the suture from the surgical cavity.

While the expandable member 116 has been described as including eight collapsible arms 154, it should be appreciated that the expandable member can alternatively include fewer collapsible arms 154 or more collapsible arms 154.

While the expandable member 116 has been described as being biased to its expanded configuration, it should be appreciated that the expandable members of the various suture passer guides described herein can alternatively be biased to their collapsed configuration. With such a configuration, for example, the user could push or release a button to move the expandable member from its collapsed configuration to its expanded configuration.

While the suture passer guide 108 is described as including an elastic film 160 (see FIGS. 5-7) that is stretched over the expandable member 116 to reduce the risk of damage to the peritoneum 186 and/or to prevent loss of inflation pressure during use of the suture passer guide 108, in certain embodiments, the suture passer guide includes a heat shrink tube disposed to cover the expandable member 116 instead of the elastic film 160. In this embodiment, the heat shrink tube is similarly sealed to the distal end of the elongate member 114 and to the rounded base 156 of the expandable member 116 in a substantially fluid-tight manner. This arrangement can help to prevent gases within the surgical cavity from escaping through open spaces within the expandable member 116 and into the port site wound 183 during use of the suture passer guide 108. Examples of materials from which the heat shrink tube can be formed include polyethylene terephthalate (PET), polytetrafluoroethylene (PTFE), polyetheretherketone (PEEK), polypropylene, and polyethylene.

While the suture passers described above include a film or heat shrink tube that covers the expandable member, in certain embodiments, no such film or heat shrink tube is used. In such embodiments, the openings between the arms of the expandable member are uncovered.

While the suture passer guide 108 is described as including self-sealing elastic plugs 161, 163 sized to be disposed within the distal openings 124, 126, 132, 134, in certain embodiments, the suture passer guide 108 may alternatively include self-sealing elastic patches that are sized to cover the distal openings 124, 126, 132, 134. In this case, the elastic patches include a self-adhesive area disposed along an edge of one surface of the patches, such that the patches can be adhered to the external surface of the elongate member 114 surrounding a distal opening 124, 126, 132, 134. A thickness of the elastic patches is typically about 0.005 to about 0.020 in.

While some of the suture passer guides described above include seals positioned over the distal openings 124, 126, 132, 134 of the guide passages, it should be understood that the seals can alternatively or additionally be positioned over the proximal openings 120, 122, 128, 130 of the guide passages.

While certain suture passer guides described above include seals positioned in or over openings of the guide passages to inhibit gases from escaping from the surgical cavity via the guide passages, in certain implementations, no such seals are used.

In some embodiments, the upper guide passages 136, 138 are aligned such that the suture passer 110 can be disposed simultaneously within the upper guide passages 136, 138, and the lower guide passages 140, 142 are aligned such that the suture passer 110 can be disposed simultaneously within the lower guide passages 140, 142.

While the suture passer guide 108 has been described as including colored bands 176, 178 only in the proximity of the proximal openings 120, 122, 128, 130 of the guide passages 136, 138, 140, 142, in certain embodiments, the suture passer guide includes matching colored bands around the proximal and distal openings 120, 122, 124, 126 of the upper guide passages 136, 138 and matching colored bands around the proximal and distal openings 128, 130, 132, 134 of the lower guide passages 140, 142. This can help to ensure that the surgeon selects the appropriate proximal opening in which to insert the suture passer 110. For example, in such embodiments, the surgeon could simply insert the suture passer 110 into the proximal opening that is associated with a colored band that matches the colored band along which the outer surface of the patient's surgical wall lies.

In addition, while the suture passer guides above have been described as having colored bands to help the user select the appropriate guide passages to use, the suture passer guide can alternatively or additionally have any of various other markings (e.g., letters, numbers, symbols, etc.) that can be used in a similar manner. Alternatively, the endoscopic port can include no markings at all. In such cases, the surgeon can simply rely on the positions of the guide passages 136, 138, 140, 142 to determine which of those guide passages to use for a particular procedure.

While the inner shaft 168 has been described as including channels 172, 174 that align within openings in the elongate member 114 of the suture passer guide 108 to form the guide passages 136, 138, 140, 142, in certain embodiments, a solid inner shaft is alternatively used. In such embodiments, the guide passages of the suture passage guide can be configured to extend alongside the solid inner shaft rather than through the solid inner shaft.

While the endoscopic surgical kit 500 has been described as including a single endoscopic port 102, obturator 104, suture passer guide 108, and suture passer 110, the kit can alternatively include multiple, different endoscopic ports, obturators, suture passer guides, and/or suture passers of varying size for performing endoscopic (e.g., laparoscopic) surgical procedures on patients of various sizes.

While the endoscopic surgical kit 500 has been described above as carrying out a laparoscopic surgical procedure, it should be understood that the endoscopic surgical kit 500 can be used to perform any of various other types of endoscopic surgical procedures.

Figure 10:
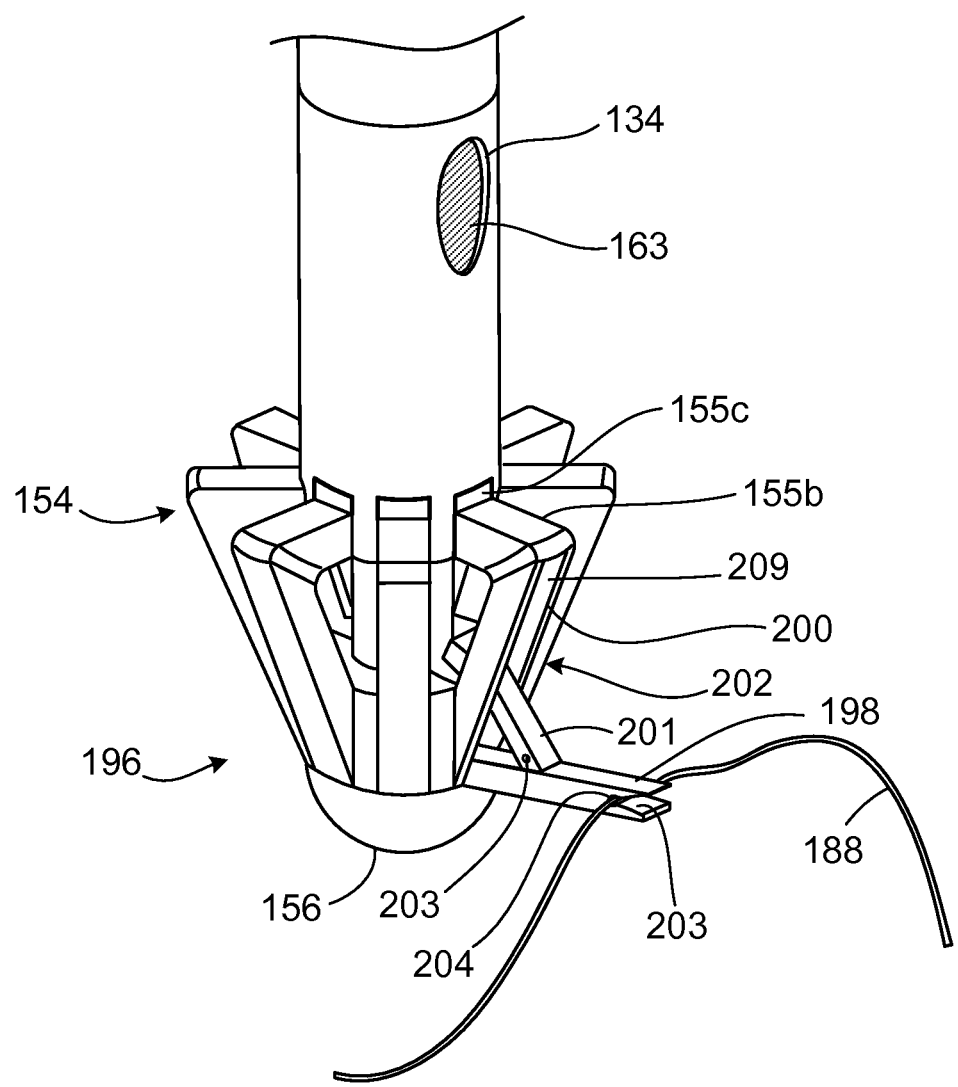
FIG. 10 is a perspective view of a distal end region of a suture passer guide that includes an expandable member equipped with a suture positioning arm.

In certain embodiments, the expandable member of the suture passer guide is configured to carry a suture 188 into the surgical cavity. Referring to FIG. 10, for example, an expandable member 196 at the distal end region of a suture passer guide includes a suture positioning arm 198 that extends from a distal segment 200 of a collapsible arm 202 and includes a v-shaped notch 203 terminating in a hole 204 sized to hold the suture 188. The suture positioning arm 198 is coupled to the rounded base 156 via the living hinge 158 and to the distal segment 200 of the collapsible arm 202 via a lever arm 201. The lever arm 201 is coupled to the suture positioning arm 198 via another living hinge 203 and to the distal segment 200 of the collapsible arm 202 via a pin 205 and a slot 207 included within the distal segment 200. The extent to which the suture positioning arm 198 extends from the collapsible arm 202 can depend on a length of the lever arm 201. The remaining components of the suture passer guide can be similar in form and function to the like components of the suture passer guide 108. Accordingly, the expandable member 196 is biased to an expanded position such that the suture positioning arm 198 is extended (as shown in FIG. 10) while an internal shaft connected to the rounded base 156 is disposed in a proximal position. In contrast, the expandable member 196 collapses when the user extends the internal shaft distally, causing the suture positioning arm 198 to collapse within a recess 209 of the distal segment 200 as the pin 205 shifts within the slot 207 of the distal segment 200.

The suture positioning arm 198 can be preloaded with the suture 188 by placing the sliding the suture 188 through the v-shaped notch 203 and into the hole 204 and then holding the suture positioning arm 198 in its collapsed configuration. The suture 188 can be delivered to the surgical cavity with the expandable member 196 and the suture positioning arm 198 in their collapsed configurations. After the expandable member 196 has been positioned within the surgical cavity and the expandable member 196 and the suture positioning arm 198 have been expanded, the suture passer 110 can be inserted through a guide passage of the suture passer guide and used to grasp the suture 188 that is held by the suture positioning arm 198. Due to the position of the suture positioning arm 198 relative to the distal opening of the guide passage through which the suture passer 110 is inserted, the suture can be quickly and easily grasped by the suture passer without having to probe the surgical cavity for the suture 188. The suture passer 110 is then removed from the suture passer guide along with a length of the suture 188. As the suture is pulled through the tissue by the suture passer, the suture is allowed to freely slide within the hole 204. After pulling a length of the suture 188 thorough the patient's tissue such that one end of the suture is outside of the patient, the suture passer guide is rotated 180 degrees along with the length of the suture 188 that remains positioned in the hole 204 of the suture positioning arm 198. The suture passer is then re-inserted through the guide passage and used to retrieve the other end of the suture 188.

While the expandable ember 196 has been described as including only one suture positioning arm 198, in certain embodiments, the expandable member can include multiple suture positioning arms 198. For example, the expandable member can include two suture positioning arms that are spaced by approximately 180 degrees such that one of the suture positioning arms 198 is aligned with one guide passage and the other suture positioning arm 198 is aligned with another guide passage. The suture 188 can be preloaded into each of the suture positioning arms 198 and then delivered into the surgical cavity. Upon expanding the expandable member and the suture positioning arms 198, the suture passer 110 can be sequentially passed through the guide passages and used to retrieve portions of the suture 188 held by the respective suture positioning arms 198. The suture positioning arms 198 allow each of those portions of the suture 188 to be quickly and easily grasped without having to probe the surgical cavity for the suture 188 and can thus reduce the amount of time required to close the port site wound 183.

In certain embodiments, the suture passer guide includes four positioning arms 198 or six positioning arms 198 that are equidistantly spaced about the circumference of the expandable member to allow the surgeon to preload two or three sutures in the suture passer guide and then use those sutures to close of the port site wound. Such an arrangement can be particularly beneficial for repairing large port site wounds.

In some embodiments, when the expandable member 196 includes one or more suture positioning arms, an elastic film or heat shrink tube is adhered to a distal end region of an elongate member (such as the elongate member 114) and to the middle arm segments 155b of the expandable member 196. In this manner, a proximal region of the expandable member 196 is substantially covered by the elastic film or heat shrink tube, while the one or more suture positioning arms 198 are permitted to extend from the collapsible arm 202.

While the suture passer guide illustrated in FIG. 10 has been described as being preloaded with the suture 188 and then delivered into the patient, in some cases, the suture passer guide is delivered into the patient's body cavity without the suture 188. The suture passer is then used to deliver the suture into the body cavity by passing the suture passer and the suture 188 through the guide passage of the suture passer guide. Once the suture 188 has been delivered to the body cavity, the suture is loaded onto the suture positioning arm 196 (e.g., by passing the suture through the v-shaped notch 203 and into the hole 204 or by wedging the suture in the v-shaped notch 203). Typically, the suture passer can be used to load the suture 188 onto the suture positioning arm in this manner. However, a second instrument that has been inserted into the body cavity via another endoscopic port can alternatively be used to facilitate loading of the suture 188. Once the suture 188 has been loaded onto the suture positioning arm 188, the suture passer guide can be rotated 180 degrees and the end of the suture held by the suture positioning arm 198 can be retrieved and pulled through the tissue of the patient in much the same way as described above.

Figures 11A, 11B:
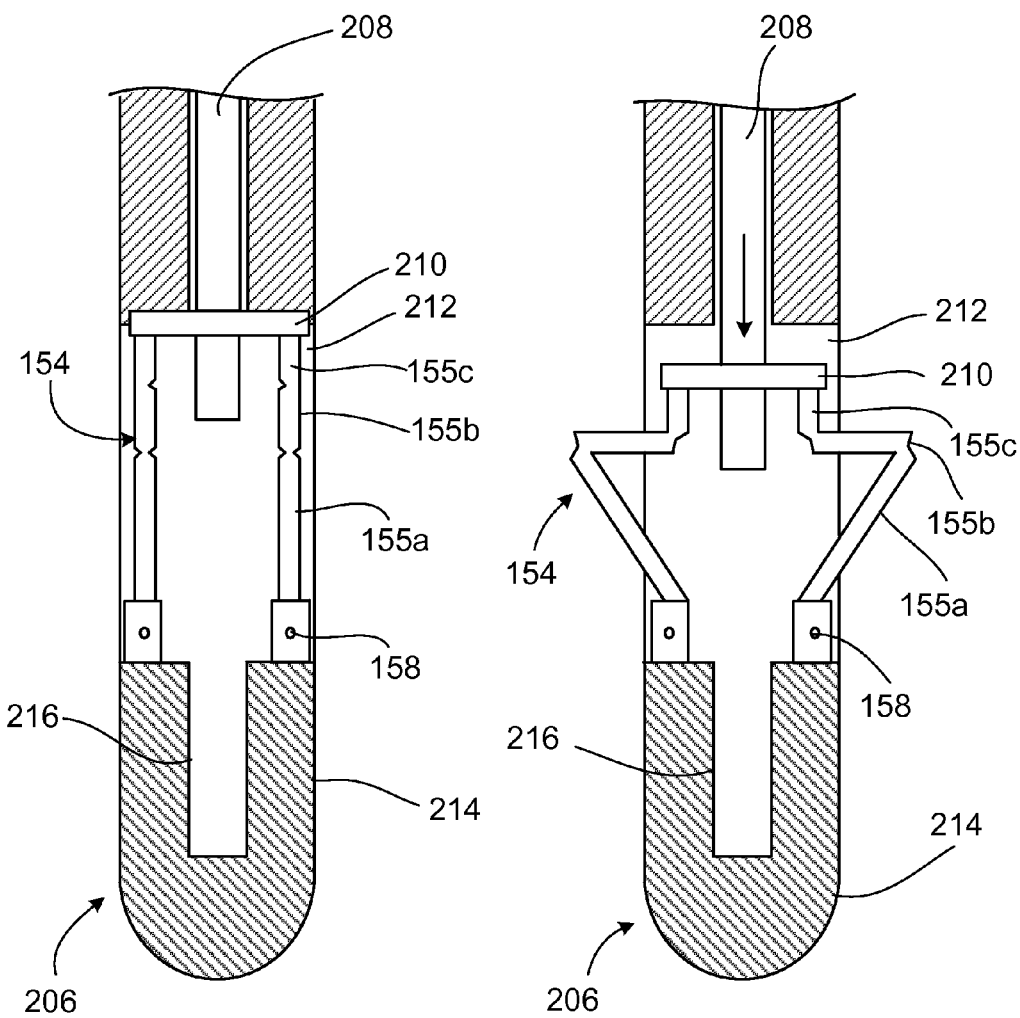
FIGS. 11A and 11B are cross-sectional schematic illustrations of a distal end region of a suture passer guide that includes an expandable member having collapsible arms actuated with a pin and shaft. The collapsible arms are shown in a collapsed configuration in FIG. 11A and in an expanded configuration in FIG. 11B.

Additionally, while the inner shaft 168 of the suture passer guide 108 has been described as being coupled to the rounded base 156, in some embodiments, other configurations are possible. For example, FIGS. 11A and 11B show an expandable member 206 including a shaft 208 coupled to a pin 210 disposed near a distal region of the shaft 208 and housed within a vertical slot 212 disposed at the distal end of the shaft 208. The remaining components of the suture passer guide can be similar in form and function to the like components of the suture passer guide 108. Accordingly, the shaft 208 can be disposed in a proximal position while a thumb button coupled to the shaft 208 (e.g., a thumb button similar to the thumb button 118 coupled to the shaft 168 of the suture passer guide 108) is released, whereas the shaft 208 can be disposed in a distal position while the thumb button is depressed. Referring particularly to FIG. 11A, the collapsible arms 154 are collapsed while the shaft 208 is disposed in a proximal position. A rounded base 214 includes a vertical channel 216 substantially aligned with the shaft 208 and sized to receive the shaft 208 as the shaft 208 is longitudinally displaced towards the rounded base 214. As shown in FIG. 11B, when the shaft 208 is extended by the user, the pin 210 is displaced within the vertical slot 212 such that the pin 210 contacts proximal segments 155c of the collapsible arms 154 and forces the collapsible arms 154 into an expanded configuration.

Figures 12A, 12B:
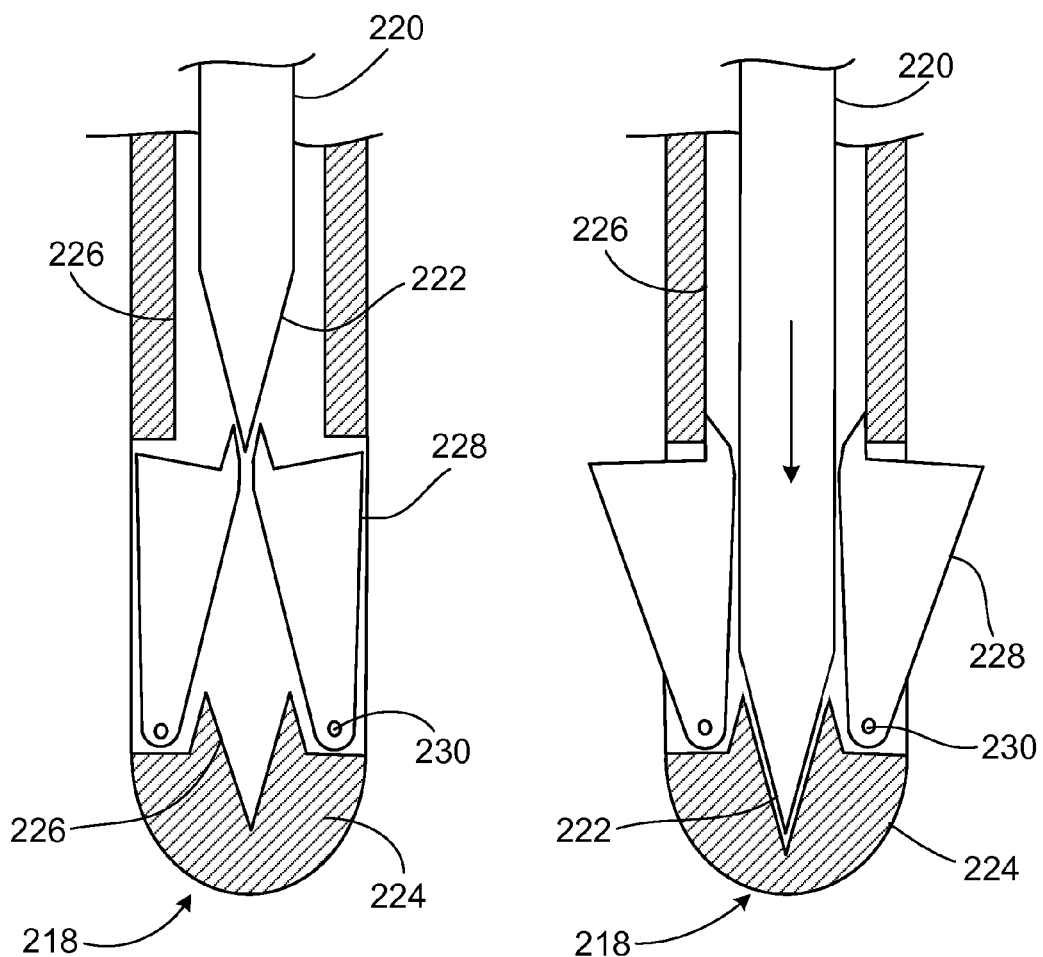
FIGS. 12A and 12B are cross-sectional schematic illustrations of a distal end region of a suture passer guide that includes an expandable member having swing arms actuated with a shaft. The swing arms are shown in a collapsed configuration in FIG. 12A and in an expanded configuration in FIG. 12B.

As shown in FIGS. 12A and 12B, in certain embodiments, an expandable member 218 at the distal end region of a suture passer guide includes a shaft 220 having a distal end formed in the shape of a conical tip 222 and a rounded base 224 including a vertical channel 226 sized to receive the shaft 220 as the shaft 220 is longitudinally displaced towards the rounded base 224 by the user. The remaining components of the suture passer guide can be similar in form and function to the like components of the suture passer guide 108. Accordingly, the shaft 220 can be disposed in a proximal position while a thumb button coupled to the shaft 220 (e.g., a thumb button similar to the thumb button 118 coupled to the shaft 168 of the suture passer guide 108) is released, whereas the shaft 220 can be disposed in a distal position while the thumb button is depressed. Referring particularly to FIG. 12A, the expandable member 218 includes two swing arms 228 that are pivotably coupled to the rounded base 224 with torsion springs 226, and the swing arms 228 are biased in a collapsed configuration while the shaft 220 is disposed in a proximal position. Proximal ends of the swing arms 228 provide a recess when the swing arms 228 are disposed in the collapsed configuration. Referring particularly to FIG. 12B, when the shaft 220 is longitudinally displaced towards the rounded base 224 by the user, the shaft 220 contacts the recess and shifts the swing arms 228 outward to an expanded configuration while the shaft 220 extends through the vertical channel 226.

In some embodiments, an expandable member can include a different set of swing arms coupled to a rounded base. For example, an expandable member can include semi-circular swing arms having semi-cylindrical recesses sized to fit against a portion of the shaft 220. Similar to the embodiment of the expandable member 218, the expandable member including the semi-circular swing arms is biased in a collapsed configuration while the shaft 220 is disposed in a proximal position and expands to an expanded configuration as the shaft 220 is shifted to a distal position and thereby contacts proximal regions of the semi-circular swing arms.

Figure 13A:
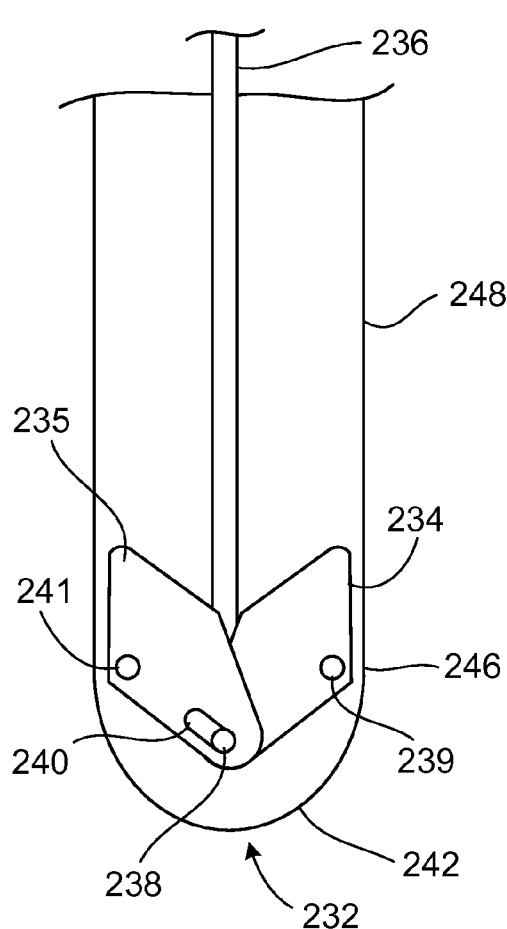
FIGS. 13A and 13B are cross-sectional schematic illustrations of a distal end region of a suture passer guide that includes an expandable member having swing arms actuated with a pin and shaft. The swing arms are shown in a collapsed configuration in FIG. 13A and in an expanded configuration in FIG. 13B.
Figure 13B:
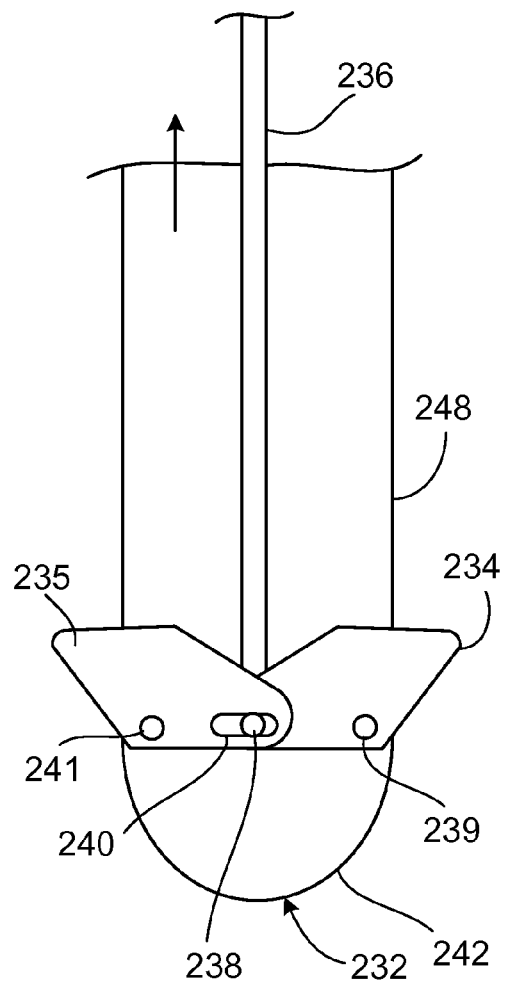

In some embodiments, swing arms of an expandable member can be coupled to a shaft. As shown in FIGS. 13A and 13B, an expandable member 232 includes two swing arms 234, 235 that are coupled to a shaft 236 at a pin 238 surrounded by a substantially linear slot 240 included within a distal region of each swing arm 234, 235. The swing arms 234, 235 are also pivotably secured to an elongate member 248 via pivot pins 239, 241. A rounded base 242 is sized and shaped to seat the swing arms 234. In this example, the swing arms 234, 235 are biased by a spring to the inward position shown in FIG. 13A. The shaft 236 is in a distal position when the swing arms 234, 235 are in this inward position, and the swing arms 234, 235 can be moved to a radially extended position by pulling proximally on the shaft 236. Referring particularly to FIG. 13A, when the shaft 236 is disposed in a distal position, the swing arms 234, 235 are disposed in a collapsed configuration. As shown in FIG. 13B, when the shaft 236 is pulled in the proximal position, the swing arms 234, 235 pivot about the pivot pins 239, 241 and extend radially outward through openings in the sidewall of an elongate member 248 into an expanded configuration.

Figures 14A, 14B:
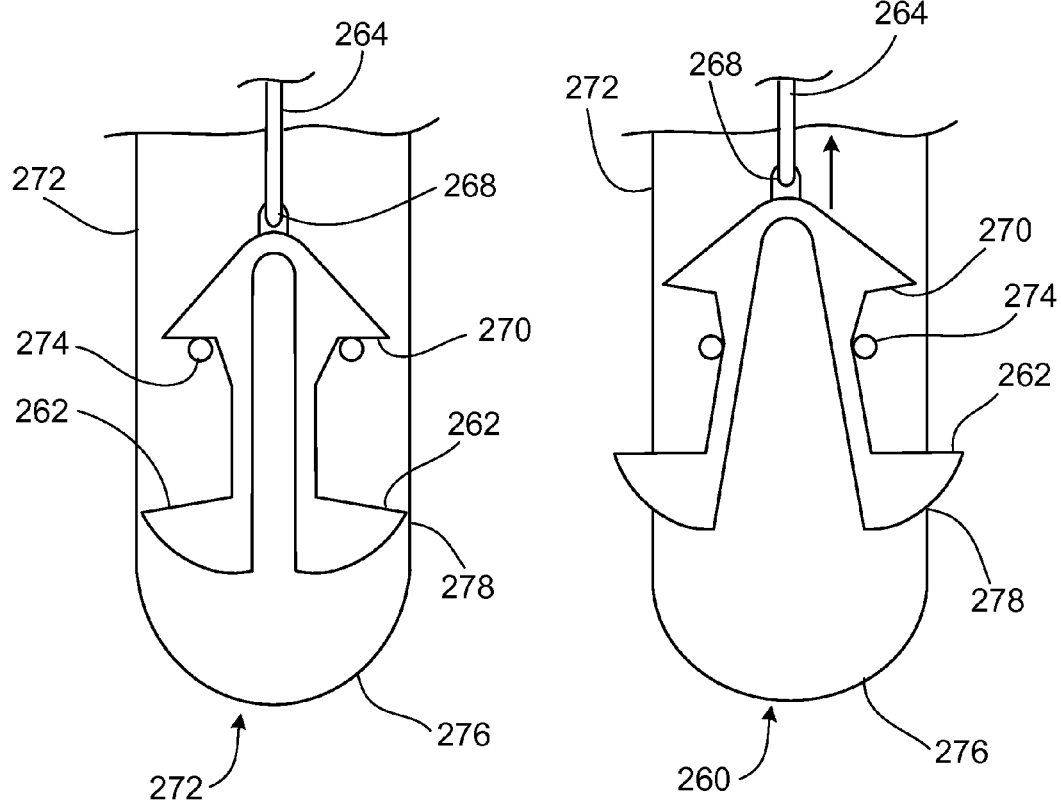
FIGS. 14A and 14B are cross-sectional schematic illustrations of a distal end region of a suture passer guide that includes an expandable member having swing arms actuated with a common pin and shaft. The swing arms are shown in a collapsed configuration in FIG. 14A and in an expanded configuration in FIG. 14B.

As shown in FIGS. 14A and 14B, in some embodiments, an expandable member 260 includes swing arms 262 that are coupled to a shaft 264 at a common pin 268 disposed near proximal ends of the swing arms 262. The swing arms 262 include ramps 270 extending along side regions of the swing arms 262, and an elongate member 272 of the suture passer guide includes internal pins 274 that are fixed relative to the elongate member 272 and are positioned to contact and ride along the tabs 270. The swing arms 262 are biased to radially extended position by a spring. A rounded base 276 extends from the elongate member 272 and includes openings 278 sized to allow passage of the swing arms 262 through the elongate member 272. Referring particularly to FIG. 14A, when the shaft 264 is disposed in a distal position, the pins 274 sit adjacent wide segments of the ramps 270 and thus hold the swing arms 262 in a collapsed configuration. In this position, the internal pins 274 contact stop surfaces of the tabs 207 and thus prevent the swing arms 262 and the shaft 264 from shifting distally past a location determined by the internal stops 274. Referring now to FIG. 14B, when the shaft 264 is pulled proximally, the pins 274 ride along the ramps 274 from the wide portions of the ramps 274 to thinner portions of the ramps 274 and thus allow the swing arms 262 to extend radially outward through the openings 278 into an expanded configuration.

Figure 15A:
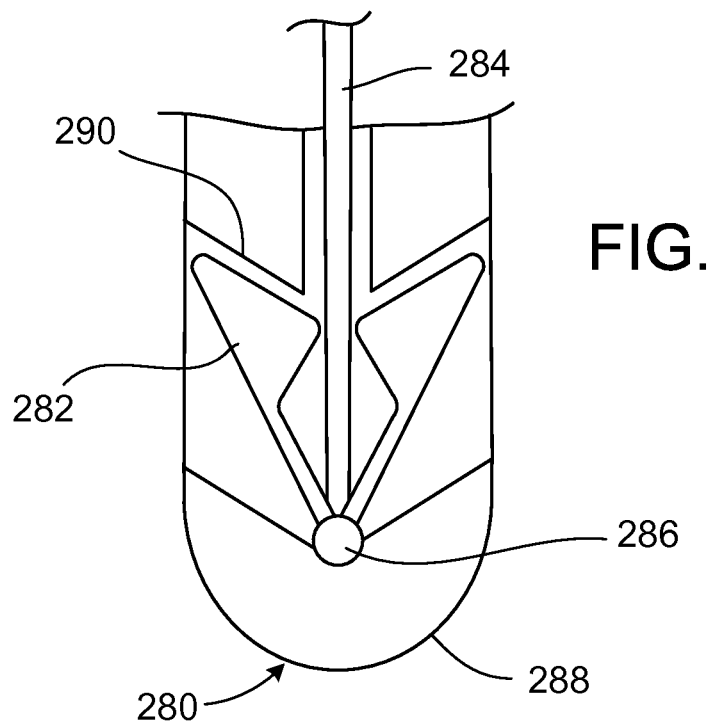
FIGS. 15A and 15B are cross-sectional schematic illustrations of a distal end region of a suture passer guide that includes an expandable member having flexible arms actuated with a common pin and shaft. The flexible arms are shown in a collapsed configuration in FIG. 15A and in an expanded configuration in FIG. 15B.
Figure 15B:
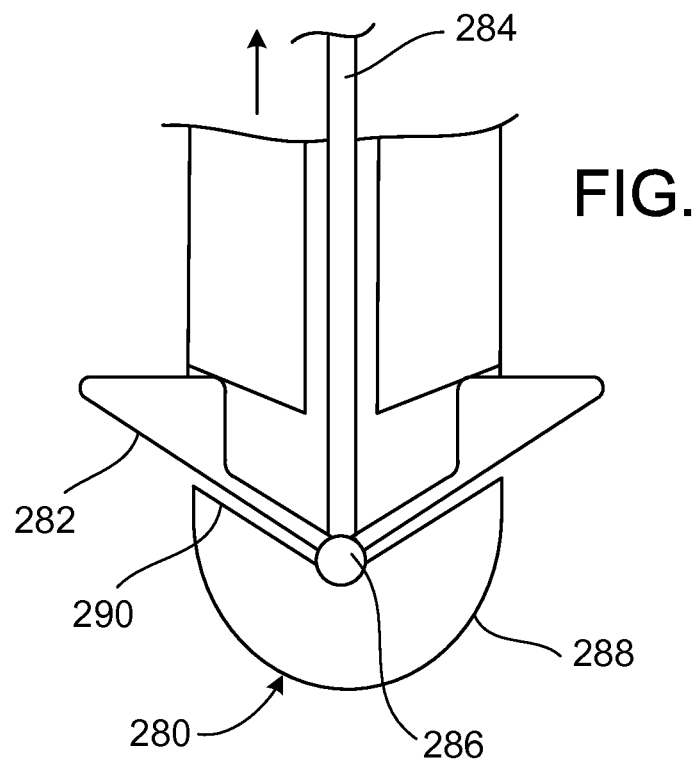

As shown in FIGS. 15A and 15B, a suture passer guide includes a shaft 284 that extends through an elongate member 283 and is pivotably coupled to two arms 282 at a pin 286. The pin 286 is also fixed to a rounded base 288. Recessed regions or gaps 290 that are sized and shaped to receive the arms 282 are formed between the elongate member 243 and the rounded base 288. The arms 282 are biased by a spring to a radially inward position in which the arms 282 are fully disposed within the recessed regions 290. As shown in FIG. 15A, the shaft 284 is in its distal most position and the arms 282 are held in a radially inward position within the recessed regions 290. Referring now to FIG. 15B, when the shaft 284 together with the rounded base 288 is pulled proximally, the arms 282 slide along angled end surfaces of the elongate member 243 and pivot radially out of the recessed regions 290 and into an expanded configuration.

While the arms 282 have been described as being connected to the rounded base 288 via the pivot pin 286, the arms can alternatively be formed of one or more resilient materials that allow the arms 282 to move back and forth between the radially expanded and contracted positions by bending. Example materials from which such flexible arms can be formed include a flexible plastic such as polypropylene, a rigid plastic such as polycarbonate, or a nylon.

Figure 16A:
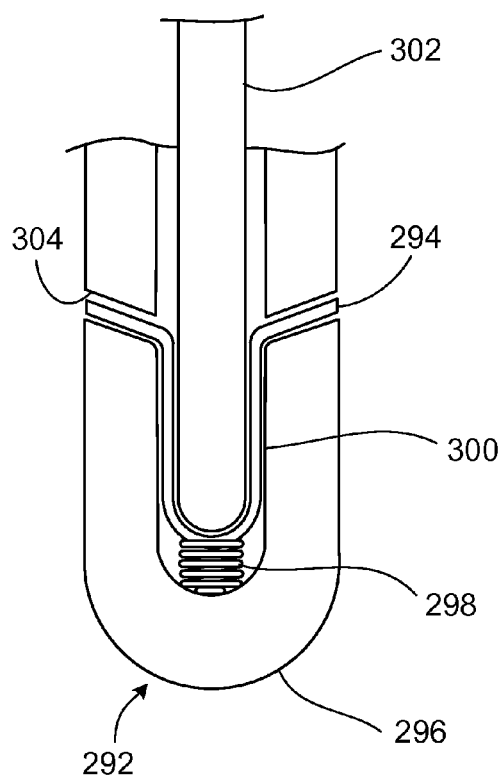
FIGS. 16A and 16B are cross-sectional schematic illustrations of a distal end region of a suture passer guide that includes an expandable member having a flexible member and a spring. The flexible member is shown in a collapsed or retracted configuration in FIG. 16A and in an expanded or extended configuration in FIG. 16B.
Figure 16B:
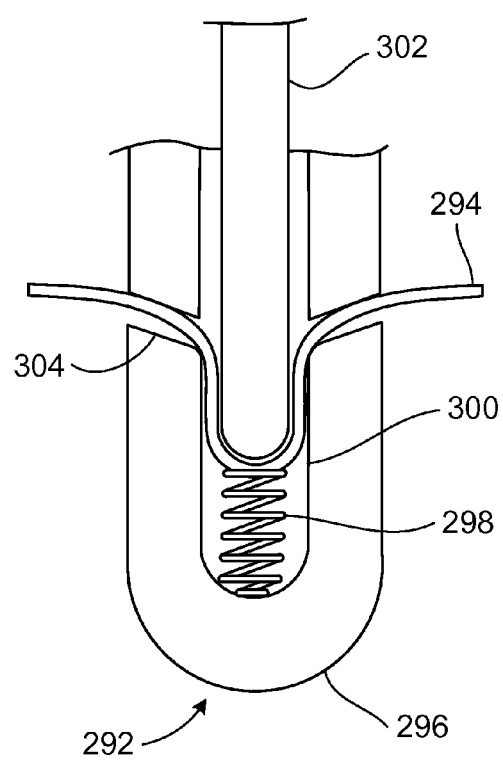

In another embodiment, as shown in FIGS. 16A and 16B, an expandable member 292 can include a flexible member 294 that is coupled to a rounded base 296 at a spring 298 disposed within a channel 300 included within the rounded base 296 and aligned with a shaft 302. The rounded base 296 includes two recess channels 304 sized and formed to surround each end of the flexible member 294. The remaining components of the suture passer guide can be similar in form and function to the like components of the suture passer guide 108. Accordingly, the shaft 302 can be disposed in a proximal position while a thumb button coupled to the shaft 302 (e.g., a thumb button similar to the thumb button 118 coupled to the shaft 168 of the suture passer guide 108) is released, whereas the shaft 302 can be disposed in a distal position while the thumb button is depressed. Referring particularly to FIG. 16A, when the shaft 284 shifts longitudinally towards the rounded base 296 and contacts the flexible member 294, the flexible member 294 simultaneously compresses the spring 298 such that the flexible member 294 shifts longitudinally into the channel 300 and therefore retracts within the recess channels 304. Referring particularly to FIG. 16B, when the shaft 302 is displaced proximally, the spring 298 extends and pushes the flexible member 294 into an expanded configuration, such that each end of the flexible member 294 extends out of the recess channels 304.

Figure 17A:
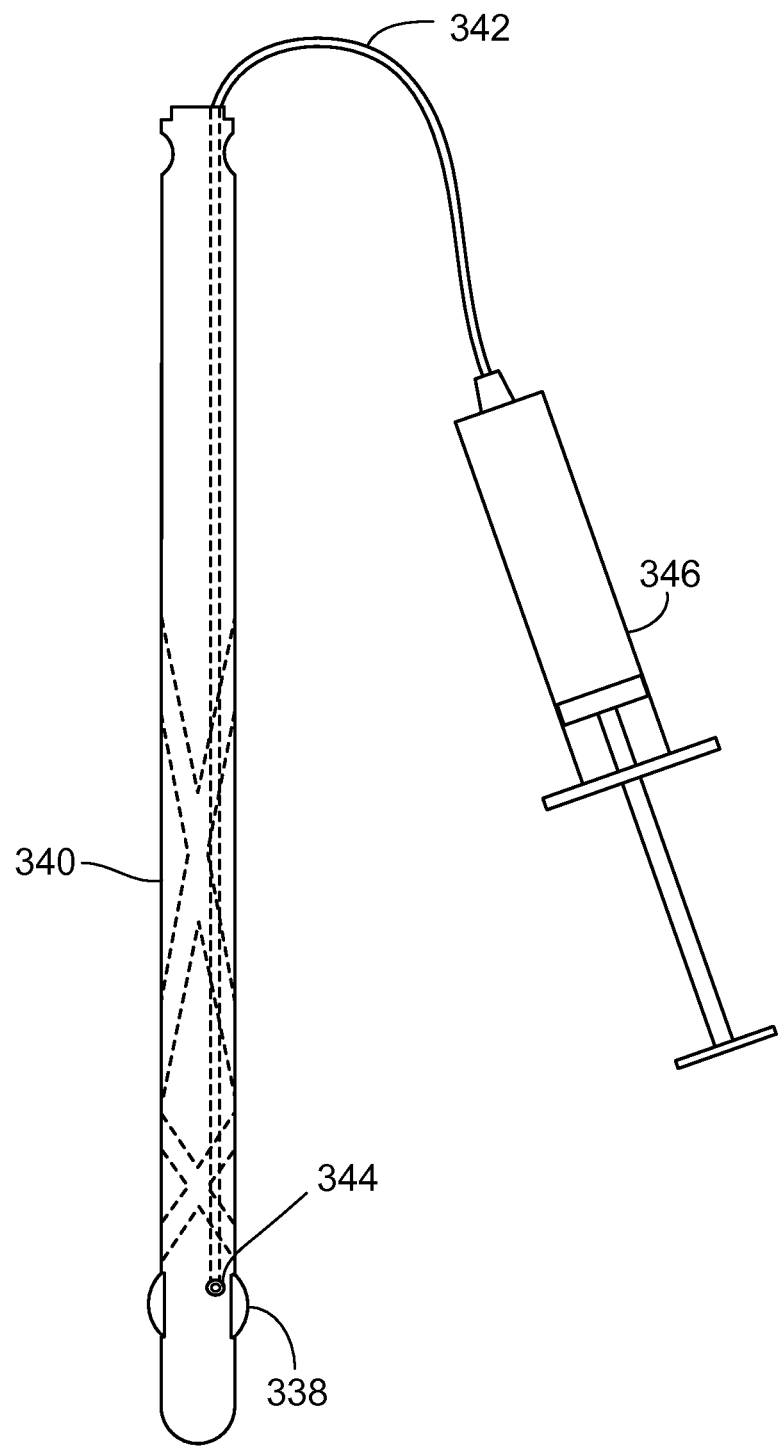
FIGS. 17A and 17B are schematic illustrations of a suture passer guide that includes an inflatable member at its distal end region, along with an inflation syringe connected to the suture passer guide. The inflatable member is shown in a collapsed or deflated configuration in FIG. 17A and in an expanded or inflated configuration in FIG. 17B.
Figure 17B:
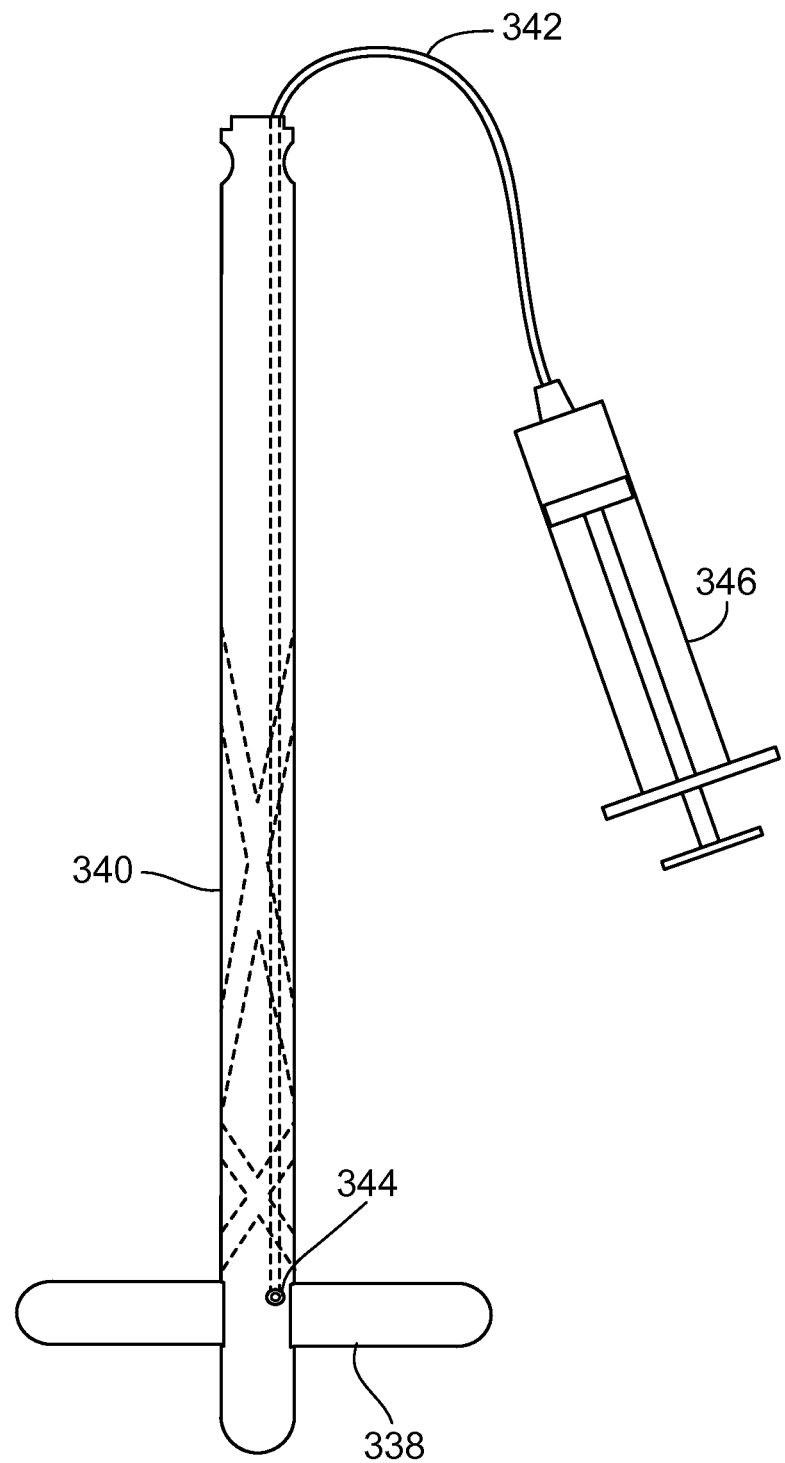

While the expandable members of the suture passer guides above have been described as being mechanically expandable, inflatable members can alternatively be used. As shown in FIGS. 17A and 17B, an inflatable member 338 surrounds a distal end region of an elongate member 340 of a suture passer guide. The inflatable member has an outer diameter that, when inflated, is greater than that of the elongate member 340, and can thus be used to anchor the suture passer guide within a surgical cavity in a manner similar to the expandable members described above. A flexible tube 342 supplies fluid to the inflatable member 338 to inflate the inflatable member 338. The flexible tube 342 feeds into the inflatable member 338 through an opening 344 in a sidewall of the elongate member 340 and further exits the elongate member 340 through a proximal end of the elongate member 340, where it can be attached to a fluid-filled syringe 346. Via the flexible tube 342, fluid can be injected into a deflated inflatable member 338 (shown in FIG. 17A), and fluid can be withdrawn from an inflated inflatable member 338 (shown in FIG. 17B).

While many of the methods described above include passing the above-described suture passer guides though the central lumen of an endoscopic port in order to position the suture passer guide within the port site wound, the suture passer guides can, if desired, be inserted directly into the port site wound after removing the endoscopic port from the wound.

Figure 18:
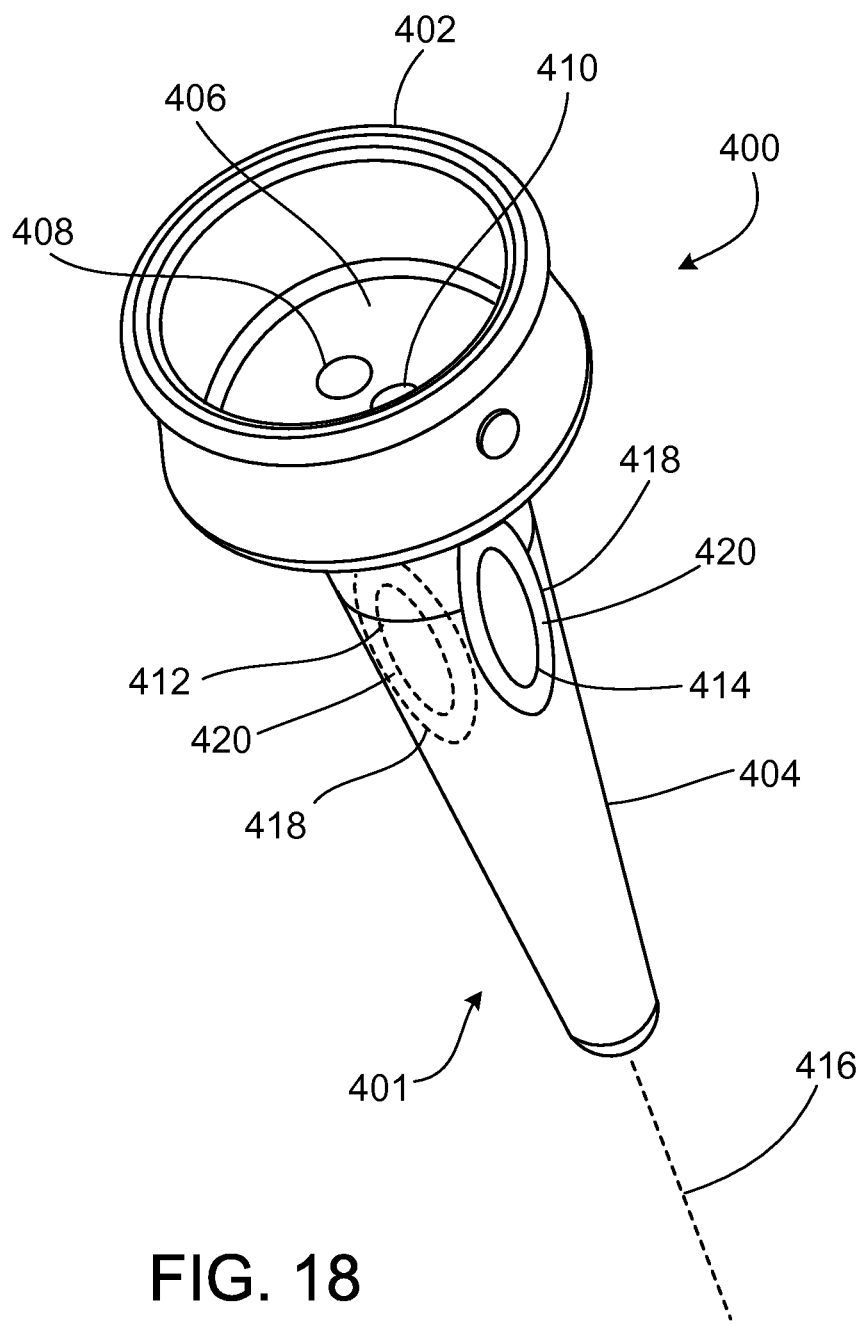
FIG. 18 is a perspective view of a suture passer guide assembly that includes a suture passer guide and elastic patches that seal openings along the suture passer guide.

Similarly, while many of the suture passer guides described herein are configured to be passed through endoscopic ports, other configurations are possible. In addition, while many of the suture passer guides described herein include expandable members in their distal end regions, in certain embodiments, the suture passer guide includes no such expandable member. FIG. 18, for example, illustrates a suture passer guide assembly 400 that can be used to suture a port site wound following removal of the endoscopic port from the wound. The suture passer guide assembly 400 includes a suture passer guide 401 to which self-sealing elastic patches 418 are secured to seal guide passages of the suture passer guide 401. The suture passer guide 401 includes a cylindrical member 402 that is secured to a proximal end of a conical member 404. The cylindrical member 402 includes a base 406 defining a left proximal opening 408 and a right proximal opening 410 that corresponds to proximal ends of left and right guide passages, respectively. The conical member 404 includes a sidewall defining a left distal opening 412 corresponding to a distal end of the right guide passage and a right distal opening 414 corresponding to a distal end of the left guide passage. The guide channels extend from their respective proximal openings 408, 410 through a longitudinal axis 416 of the conical member 404, and to their respective distal openings 412, 414.

Still referring to FIG. 18, the two self-sealing elastic patches 418 are secured to the outer surface of the conical member 404 in a manner to cover the distal openings 412, 414 of the guide passages. Each elastic patch 418 includes an adhesive ring 420 disposed along a peripheral edge of one surface of the elastic patch 418, such that the elastic patch 418 can adhere to the sidewall of the conical member 404 to create a substantially fluid-tight seal. This fluid-tight seal prevents gases (e.g., $CO_2$) within a surgical cavity from escaping through the distal openings 412, 414 and thus maintains an inflation pressure of the surgical cavity (e.g., pneumoperitoneum of the abdominal cavity) during use of the suture passer guide assembly 400. As a result, the need to re-insufflate the surgical cavity during use of the suture passer guide assembly 400 can be reduced or eliminated. The inflation pressure of the surgical cavity can be substantially maintained due to the self-sealing properties of elastic patches 418. As a suture passer is inserted through the guide passage of the suture passer guide 401, the suture passer creates a puncture in the elastic patch 418, which subsequently seals itself around the surface of the suture passer. Similarly, following removal of the suture passer from the elastic patch 418, the elastic patch 418 seals the puncture created by the suture passer. The elastic patches typically have a thickness of approximately 0.010 in. and are typically made of silicone or a TPE. An example substance from which the adhesive ring 420 is formed includes an acrylic self-adhesive substance.

In order to suture a port site wound using the suture passer guide assembly 400, the suture passer guide assembly 400 is inserted within the port site wound until the cylindrical member 402 is seated firmly against an external layer of skin surrounding the port site wound. The suture passer loaded with a suture is first inserted through the left proximal opening 408 and left guide channel, such that a first end of the suture is disposed within the surgical cavity. The suture is released from the suture passer, and the suture passer is removed from the left guide passage, such that a second end of the suture is disposed external to the surgical cavity. The suture passer is subsequently inserted through the right proximal opening 410 and right guide passage, and the first end of the suture is then grasped with the suture passer. The suture passer is then removed from the right guide passage, such that the first end of the suture is disposed external to the surgical cavity. The suture passer guide assembly 400 is then removed from the port site wound, and the first and second ends of the suture are tied to form a knot that is positioned at a desired location (e.g., proximal to the fascia layer surrounding the abdominal cavity), such that a tissue layer of the wound is substantially closed.

Figure 19:
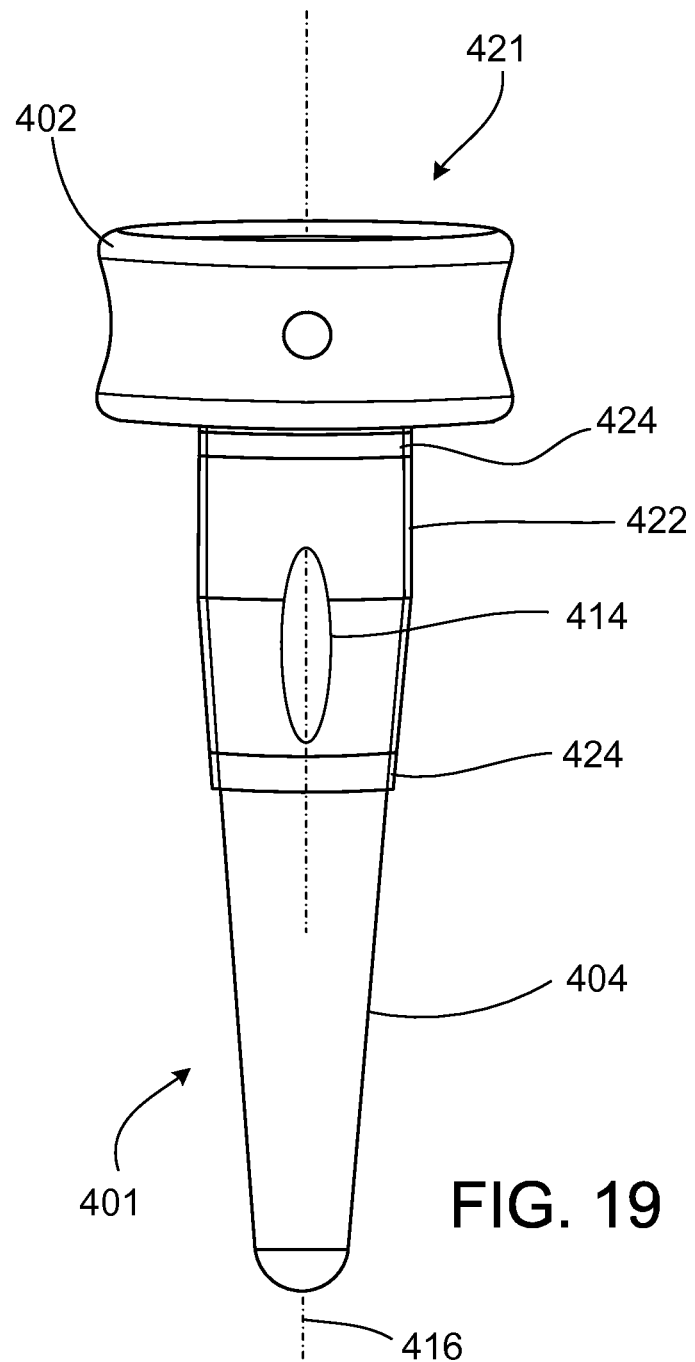
FIG. 19 is a front view of a suture passer guide assembly that includes a suture passer guide and an elastic sleeve that seals openings along the suture passer guide.

While the suture passer guide assembly 400 has been described as including self-sealing patches 418 secured to the suture passer guide 401, other types of sealing devices can alternatively be used. As shown in FIG. 19, for example, a suture passer guide assembly 421 includes a self-sealing elastic sleeve 422 disposed around the sidewall of the conical member 404 of the suture passer guide 401 to cover the distal openings 412, 414. The elastic sleeve 422 includes an adhesive ring 424 disposed on an internal surface at each end of the elastic sleeve 422, such that the elastic sleeve 422 can adhere to the sidewall of the conical member 404 to create a substantially fluid-tight seal and maintain the inflation pressure of the surgical cavity as described above. The elastic sleeve 422 typically has a thickness of approximately 0.010 in. and is typically made of silicone or a TPE. An example substance from which the adhesive rings 424 are formed includes an acrylic self-adhesive substance.

Figure 20:
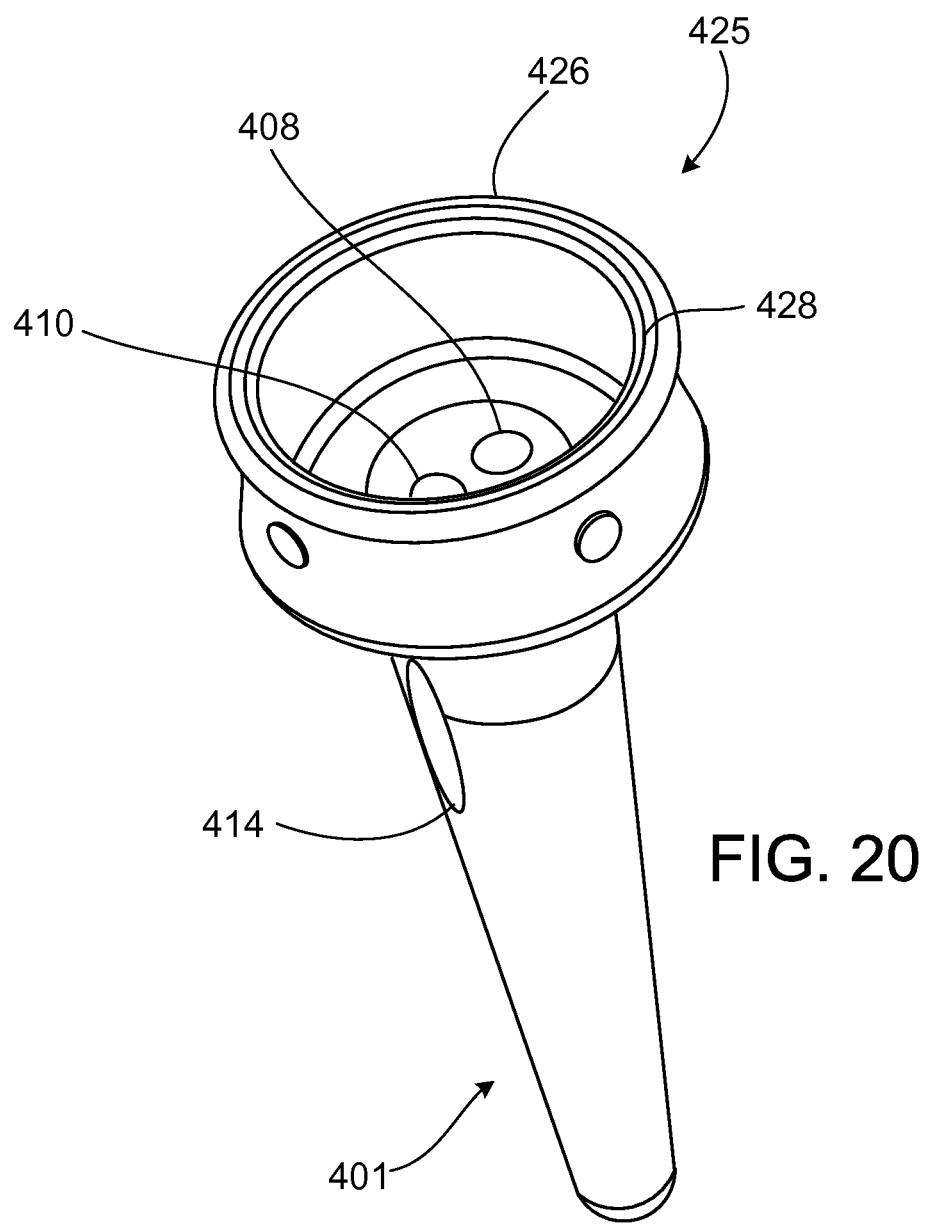
FIG. 20 is a perspective view of a suture passer guide assembly that includes an elastic cover disposed atop a suture passer guide.

In certain embodiments, a self-sealing elastic cover is secured to the suture passer guide in addition to or instead of the elastic patches 418 or sleeve 422 discussed above. As shown in FIG. 20, for example, a suture passer guide assembly 425 includes an elastic cover 426 that is positioned atop the suture passer guide 401. The elastic cover 426 is typically formed in the shape of a disk that is sized to sit atop the cylindrical member 402 and therefore cover the left and right proximal openings 408, 410. The elastic cover 426 includes an adhesive ring 428 disposed along an edge of one surface of the elastic cover 426, such that the elastic cover 426 can adhere to a proximal end of the cylindrical member 402 to create a substantially fluid-tight seal and maintain the inflation pressure of the surgical cavity as described above. The elastic cover 426 typically has a thickness of approximately 0.050-0.100 in. and is typically made of silicone or a TPE. An example substance from which the adhesive ring 428 is formed includes an acrylic self-adhesive substance.

The self-sealing elastic cover can alternatively be sized to be disposed within a recess of the cylindrical member 402, such that the elastic cover can be seated against the base 406 and therefore cover the left and right proximal openings 412, 414. The elastic cover can include an adhesive patch disposed across the entire surface of the elastic cover, such that the elastic cover can adhere to the base 406 to create a substantially fluid-tight seal and maintain the inflation pressure of the surgical cavity as described above. Typically, the elastic cover has a thickness of approximately 0.010 in. and is typically made of silicone or a TPE. An example substance from which the adhesive patch is formed includes an acrylic self-adhesive substance.

Figure 21:
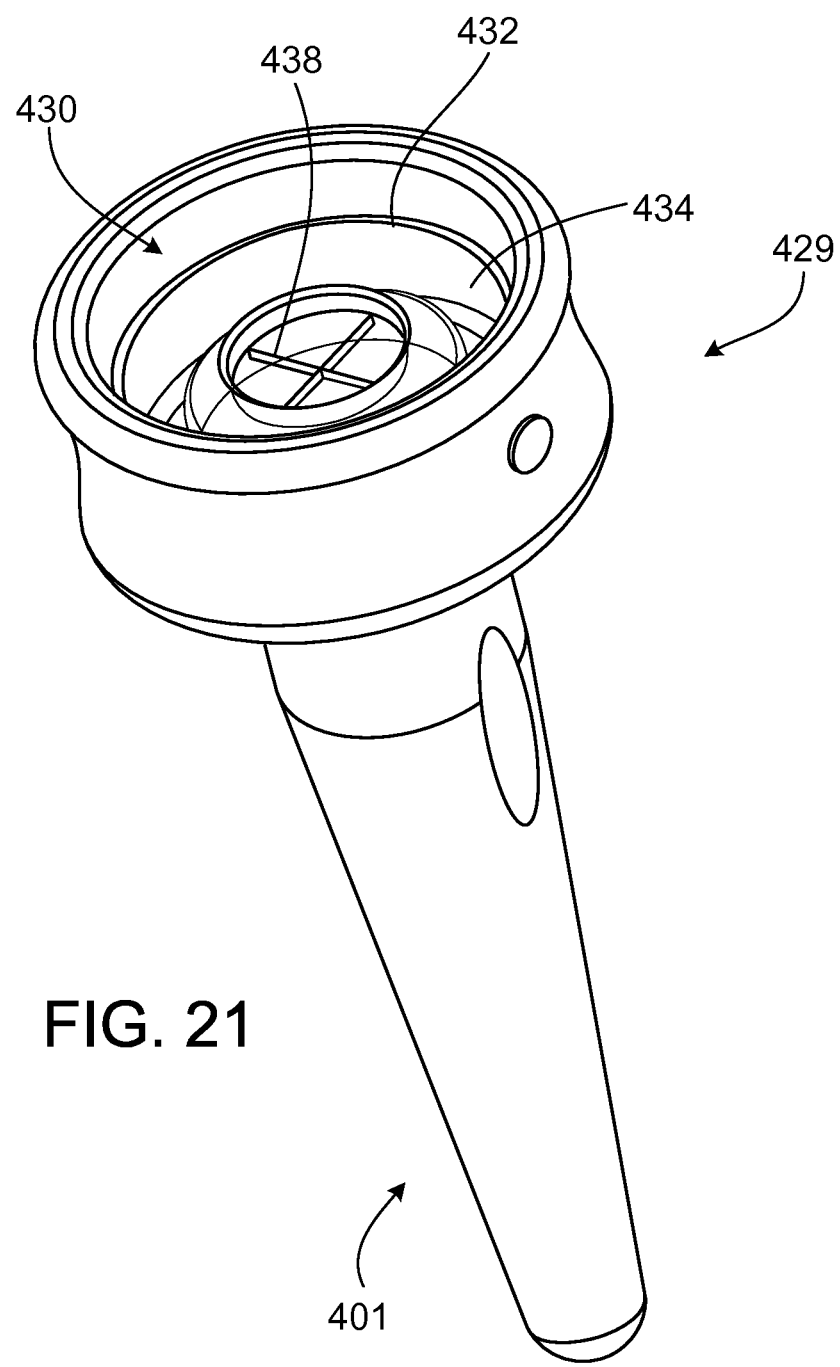
FIG. 21 is a perspective view of a suture passer guide assembly that includes an insertable elastic cap disposed within a recess of a suture passer guide.

In certain embodiments, a self-sealing insertable elastic cap is secured to the suture passer guide in addition to or instead of the elastic patches 418 or sleeve 422 described above. As shown in FIG. 21, for example, a suture passer guide assembly 429 includes an elastic cap 430 positioned atop the suture passer guide 401. The elastic cap 430 includes a lid 432 and a lip 434. The elastic cap 430 is sized to be disposed within the recess of the cylindrical member 402, such that the elastic cap 430 can be seated against the base 406 of the suture passer guide 400 and therefore cover the left and right proximal openings 412, 414. The elastic cap 430 includes an adhesive ring 436 disposed along a distal surface of the lip 434, such that the elastic cap 430 can adhere to the base 406 to create a substantially fluid-tight seal and maintain the inflation pressure of the surgical cavity as described above. The lid 432 includes two slits 438 that share a common center point and that are disposed perpendicular to one another. The inclusion and arrangement of the slits 438 serve to facilitate passage of the suture passer through the elastic cap 430. The lid 432 typically has a thickness of approximately 0.080 in., and the lip 434 typically has a thickness of approximately 0.125 in. The elastic cap 430 is typically made of silicone or a TPE. An example substance from which the adhesive ring 436 is formed includes an acrylic self-adhesive substance.

Figure 22:
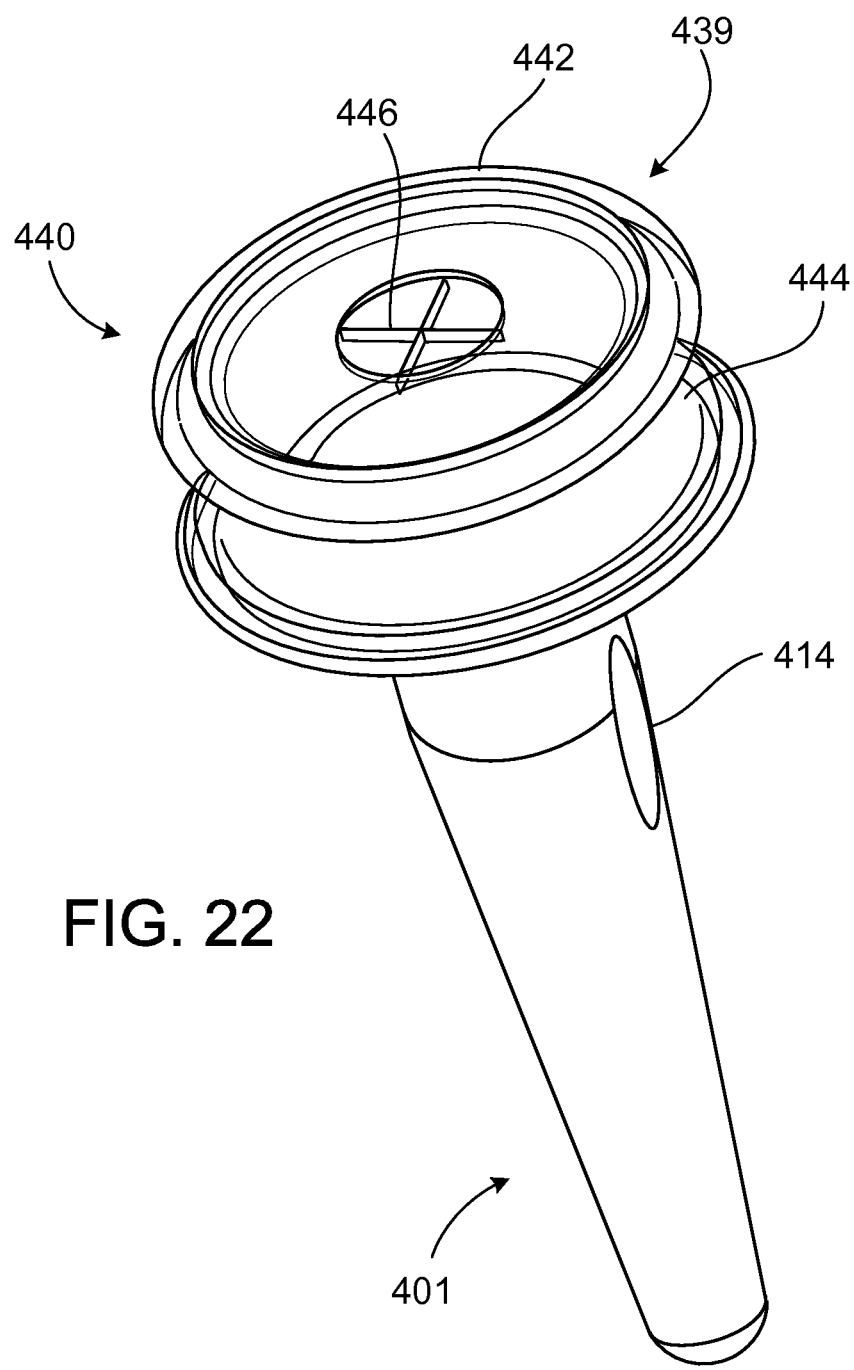
FIG. 22 is a perspective view of a suture passer guide assembly that includes a snap-on elastic cap disposed atop a suture passer guide.

A self-sealing snap-on elastic cap can be secured to the suture passer guide in addition to or instead of the elastic patches 418 or sleeve 422 described above. As shown in FIG. 22, for example, a suture passer guide assembly 439 includes an elastic cap 440 positioned atop the suture passer guide 401. The elastic cap 440 includes a lid 442 and a lip 444. The elastic cap 440 is sized to fit around the cylindrical member 402, such that the elastic cap 440 covers the left and right proximal openings 412, 414. The lid 442 includes two slits 446 that share a common center point and that are disposed perpendicular to one another in order to facilitate passage of the suture passer through the elastic cap 440, as described above with respect to the insertable elastic cap 430. Each of the lid 442 and the lip 444 of the elastic cap 440 typically has a thickness of approximately 0.050-0.100 in. The elastic cap 440 is typically made of silicone or a TPE.

Figure 23:
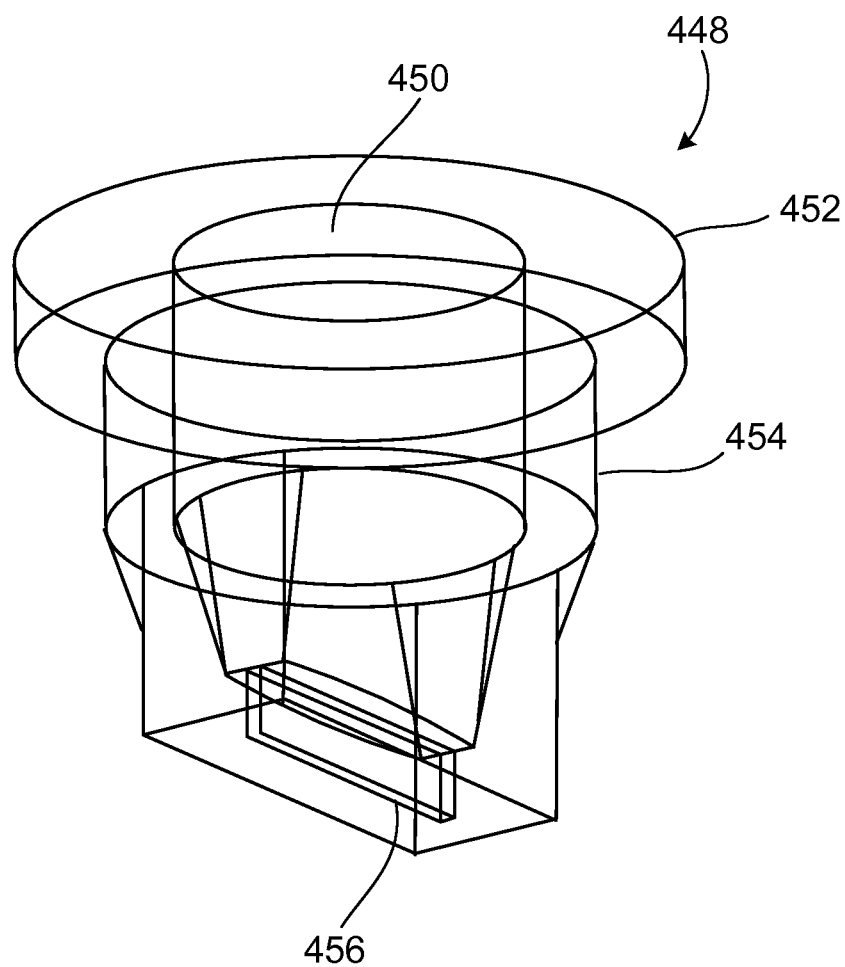
FIG. 23 is a perspective view of an elastic seal plug that can be disposed within an opening of a guide passage in a suture passer guide.

In certain embodiments, the suture passer guide includes one or more self-sealing elastic plugs that can be disposed within the guide passage of a suture passer guide to seal the guide passage. As shown in FIG. 23, an elastic plug 448 includes a channel 450 through which the suture passer can be inserted, a lip 452, and an insertable peg 454 adjacent to the lip 452. The insertable peg 454 is sized to be disposed within the proximal openings 412, 414 and is formed in the shape of a wedge. The channel 450 narrows to a slit 456 within a distal end of the insertable peg 454. The slit 456 is substantially sealed, such that the inflation pressure of the surgical cavity cannot escape via the slit 456. In addition, the slit 456 can slightly expand to receive the suture passer in a manner to maintain a fluid-tight seal with the suture passer. The elastic plug 448 is typically made of silicone or a TPE. The elastic plug can be disposed in the proximal and/or distal openings of the guide passages formed in any of the various suture passer guides described herein to seal those passages.

In some embodiments, the elastic plug includes an insertable peg formed in the shape of a wedged cone, such that a channel narrows to a set of two slits that share a common center (i.e., the slits are arranged in the pattern of an 'x'). Such an arrangement can help to ensure that a suture passer inserted through the plug is directed to a central region of the plug that contains the slits.

While the suture passer guide 401 has been described as including no expandable member, the suture passer guide can alternatively be equipped with a mechanically expandable or inflatable member secured to a distal end region of the conical member 404.

While certain suture passer guides have been described as including only one passage or two passages (e.g., two passages that are positioned at the same longitudinal location along the suture passer guide but are circumferentially spaced by about 180 degrees) through which a suture passer is inserted during a suturing procedure, it should be understood that more than two passages can be provided. In larger suture passer guides that are used for suturing port site wounds caused by larger sized endoscopic ports, for example, the suture passer guide may include four passages that are positioned at the same longitudinal location along the suture passer guide but are circumferentially spaced by about 90 degrees).

Figure 24:
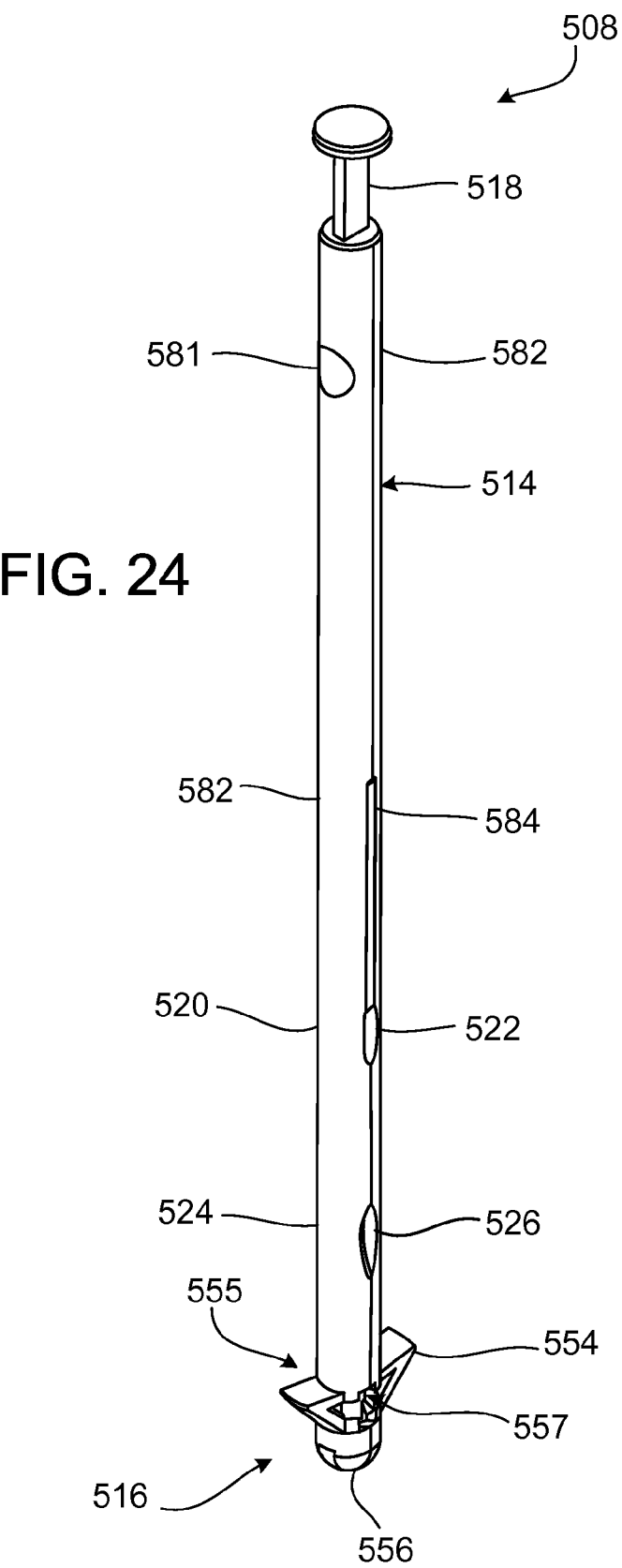
FIG. 24 is a perspective view of a suture passer guide that includes an expandable member having two collapsible arms.

In some embodiments, the collapsible arms of the expandable member are arranged so that certain adjacent collapsible arms are spaced by relatively large gaps that can improve the ease with which the suture passer guide can be tilted within a surgical cavity during use. As shown in FIG. 24, for example, a suture passer guide 508 includes an expandable member 516 having two collapsible arms 554 that are coupled to a rounded base 556. The collapsible arms 554 are similar in construction and function to the collapsible arms 154 of the expandable member 116 described above, with the exception that the collapsible arms 554 have a different width than that of the collapsible arms 154. The rounded base 556 is similar in construction and function to the rounded base 156 of the expandable member 116 described above, with the exception that the rounded base 556 includes a different number of hinges (e.g., such as the living hinges 158 that couple to the distal segments 155a of the collapsible arms 154) than that of the rounded base 156. The collapsible arms 554 are spaced approximately 180° apart from each other (as measured from a central vertical plane extending through center lines of the collapsible arms 554). Each of the collapsible arms 554 typically has a width of about 5 cm to about 8 cm.

The suture passer guide 508 further includes an elongate tubular member 514 that is similar in function to the elongate tubular member 114 of the suture passer guide 108 described above, with the exception that a distal end of the elongate tubular member 514 has a different edge profile (i.e., to allow coupling of the elongate tubular member 514 to the collapsible arms 554 of the expandable member 516) than that of the elongate tubular member 114. The elongate tubular member 514 is coupled at a distal end region to the expandable member 516 and at a proximal end region to a button 518 that is substantially similar in function to the button 118 of the suture passer guide 108. The collapsible arms 554 extend radially from a wall of the elongate tubular member 514 and in a direction that is approximately perpendicular to openings 520, 522, 524, 526 within the elongate tubular member 514. The distance between the collapsible arms 554 and the direction in which the collapsible arms 554 extend provide two circumferential gaps 555, 557 that are longitudinally aligned with the distal openings 524, 526, respectively. The gaps extend from one collapsible arm 554 to the other collapsible arm 554 for about 90° to about 160° around the circumference of the expandable member 516. The longitudinal alignment of the gaps 555, 557 with the openings 524, 526 (i.e., in the direction in which the suture passer guide 508 is tilted during use) reduces the force required to tilt the suture passer guide 508 within the wound during use of the suture passer guide 508 as compared to the force that would be required to tilt a suture passer guide including an expandable member having collapsible arms that form smaller circumferential gaps that are aligned with the openings. Accordingly, the suture passer guide 508 can be more easily tilted within the surgical cavity to allow a distal end of a suture passer (e.g., the suture passer 110) to be placed in close proximity to an end of a suture within a surgical cavity (e.g., the peritoneal cavity 180) of a patient so that the suture passer can be used to grasp the end of the suture.

The openings 520, 526 and the openings 522, 524 within the elongate tubular member 514 of the suture passer guide 508 are similar in shape to the openings 120, 126 and the openings 122, 124, respectively, of the elongate tubular member 114. The openings 520, 526 and the openings 522, 524 partially form first and second guide passages that are substantially similar in construction and function to the guide passages 136, 138, respectively, of the elongate tubular member 114. Elongate depressions 582, 584 extend upward from the proximal openings 520, 522 and serve to narrow a portion of the wall of the elongate tubular member 514, thereby reducing the volume between an inner surface of the elongate tubular member 514 and an internal shaft 568 (shown in FIG. 25) disposed within a lumen of the elongate tubular member 514 (as compared, for example, to the volume between the inner surface of the elongate tubular member 114 and the internal shaft 168 of the suture passer guide 108 described above). Such a reduced volume between the inner surface of the elongate tubular member 514 and the internal shaft 568 reduces the region through which gases can pass through the suture passer guide 508 and thus can reduce the loss of inflation pressure from the surgical cavity through the suture passer guide 508 during use of the suture passer guide 508. A length of the elongate depressions 582, 584 is typically about 1 cm to about 5 cm.

Figure 25:
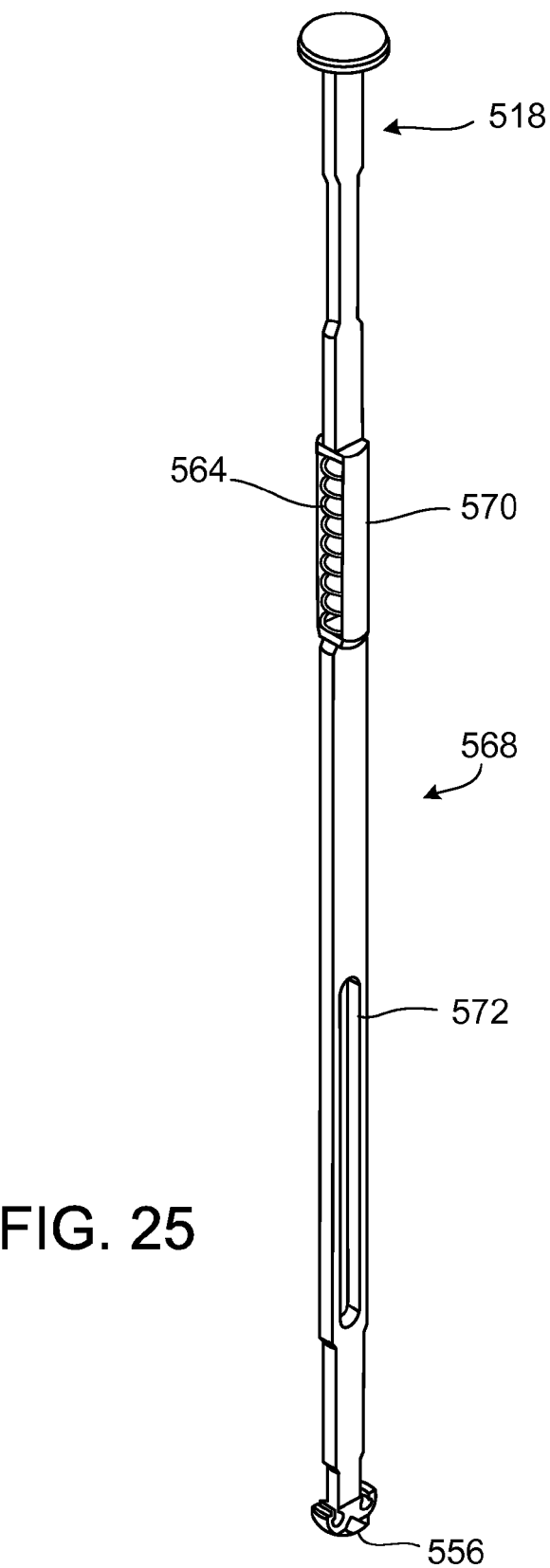
FIG. 25 is a perspective view of an inner shaft assembly of the suture passer guide of FIG. 24.

Referring to FIG. 25, the internal shaft 568 is substantially similar in function to the shaft 168 of the suture passer guide 108 and thus is operable to distally extend the expandable member 516 from the elongate tubular member 514. The internal shaft 568 includes a proximal member 570 and a distal channel 572 that is oriented perpendicular to the proximal member 570. The distal channel 572 is similar in shape and function to the channel 172 within the internal shaft 168 of the suture passer guide 108 and accordingly forms a portion of the first and second guide passages extending between the openings 520, 526 and the openings 522, 524, respectively, within the elongate tubular member 514. The proximal member 570 forms an opening that is sized to hold a spring 564 coupled to a distal end of the button 518, such that when the button 518 is depressed, the spring 564 is compressed against a distal base of the proximal member 570 and thereby moves the internal shaft 568 distally within the elongate tubular member 514. Providing the compression mechanism (i.e., the button 518) as one component improves the ease with which the suture passer guide 508 can be assembled.

Referring again to FIG. 24, the elongate tubular member 514 includes two round depressions 581, 582 that provide finger gripping surfaces near the proximal end of the elongate tubular member 514. Alternatively, the depressions 581, 582 can have any of various other shapes that enhance gripability. The proximal end region of the elongate tubular member 514 may alternatively include etched rings similar to the etched rings 181 of the suture passer guide 108 described above.

In some embodiments, the suture passer guide 508 further includes one or more of self-sealing elastic plugs sized to be disposed within the distal openings 524, 526 of the elongate tubular member 514 and an elastic film that surrounds the expandable member 516. The self-sealing plugs and film can be similar to the plugs 161, 163 and the film 160, respectively, of the suture passer guide 108 described above and can, for example, serve to maintain the inflation pressure within a surgical cavity during use of the suture passer guide 508.

In certain embodiments, the suture passer guide 508 further includes one or more surface features for determining a surgical wall thickness. Examples of such surface features include ruler markings and colored bands similar to the ruler markings 179 and the colored bands 176, 178, respectively, of the suture passer guide 108 described above.

While the suture passer guide 508 has been described as including one set of guide passages, in some embodiments, the suture passer guide includes more than one set of guide passages. In such embodiments, the internal shaft 568 typically includes one or more additional channels that are similar in shape and function to the channel 572. The elongate tubular member 514 can also include one or more additional sets of elongate depressions that are similar in shape and function to the elongate depressions 582, 584.

Figure 26:
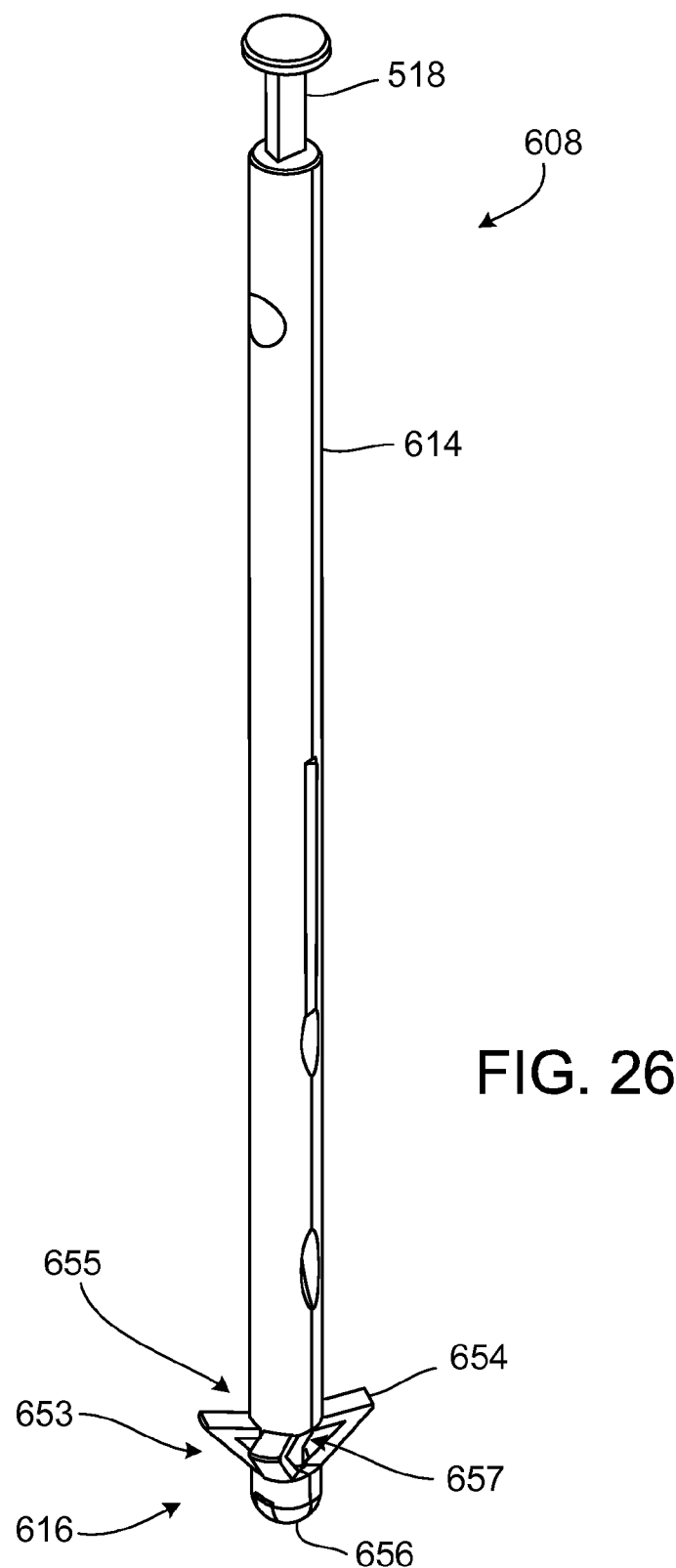
FIG. 26 is a perspective view of a suture passer guide that includes an expandable member having two groups of two collapsible arms.

While the suture passer guide 508 has been described as including two collapsible arms 554 that are positioned opposite one another, in some embodiments, the suture passer guide includes multiple groups of collapsible arms that are circumferentially spaced from one another. In such embodiments, the groups of collapsible arms are typically circumferentially spaced from one another by a greater distance than the adjacent collapsible arms are spaced from one another within those groups. Such an arrangement can increase the tiltability of the suture passer guide within a surgical cavity. As shown in FIG. 26, one such suture passer guide 608 includes an expandable member 616 having four collapsible arms 654 (i.e., two groups 653 that each include two collapsible arms 654) that are coupled at their distal end regions to a rounded base 656 and at their proximal end regions to an elongate tubular member 614. The collapsible arms 654 are similar in construction and function to the collapsible arms 554 of the expandable member 516 described above, with the exception that the collapsible arms 654 have a different width than that of the collapsible arms 554. The rounded base 656 is similar in construction and function to the rounded base 556 of the expandable member 516 described above, with the exception that the rounded base 656 includes a different number of hinges (i.e., hinges that couple to distal segments of the collapsible arms 654) than that of the rounded base 556. The elongate tubular member 614 is similar in construction and function to the elongate tubular member 514 of the suture passer guide 508 described above, with the exception that a distal end of the elongate tubular member 614 has a different edge profile (i.e., to allow coupling of the elongate tubular member 614 to the collapsible arms 654) than that of the elongate tubular member 514.

The groups 653 of the collapsible arms 654 are spaced approximately 180 degrees apart from each other (as measured from a vertical plane that is centered between the two collapsible arms 654 of each group 653). Circumferential gaps 655, 657 between the groups 653 extend about 90° to about 150° around the circumference of the expandable member 616. The circumferential gaps 655, 657 are larger than (e.g., about 60° to about 100° larger than) the gaps formed between the adjacent collapsible arms 654 within the groups 653. The gaps between the adjacent collapsible arms 654 within the groups 653, for example, typically extend about 30° to about 60° around the circumference of the expandable member 616. Each collapsible arm 654 has a width of about 0.2 cm to about 0.5 cm.

The expandable member 616 can be retracted and expanded by pressing and releasing the button 518 located at the proximal end region of the elongate tubular member 614. In the manner described above with respect to the suture passer guide 508, the button 518 is coupled to the expandable member 616 via the internal shaft 568 and the spring 564 (shown in FIG. 25) in order to operate the expandable member 616 in this way.

Due to the increased number of collapsible arms 654 provided around the expandable member 616 (as compared to the number of collapsible arms 554 situated around the expandable member 516 described above), the circumferential gaps 655, 657 in the expandable member 616 are smaller than the circumferential gaps 555, 557 in the expandable member 516. As a result, the user will encounter greater resistance to tilting the suture passer guide 608 as compared to tilting the suture passer guide 508. However, the two additional collapsible arms 654 of the expandable member 616 (as compared to the expandable member 516) provide additional surface area upon which the traction force between the expandable member 616 and the inner lining of the surgical cavity can be distributed during use of the suture passer guide 608. The increased distribution of the traction force improves the stability of the suture passer guide 608 while the suture passer guide 608 is held against the inner lining of the surgical cavity and, due to the more evenly distributed forces acting on the inner lining of the surgical cavity, further reduces the probability that any collapsible arm 654 will tear or otherwise damage the inner lining of the surgical cavity while the suture passer guide 608 is held against the inner lining of the surgical cavity.

Figure 27:
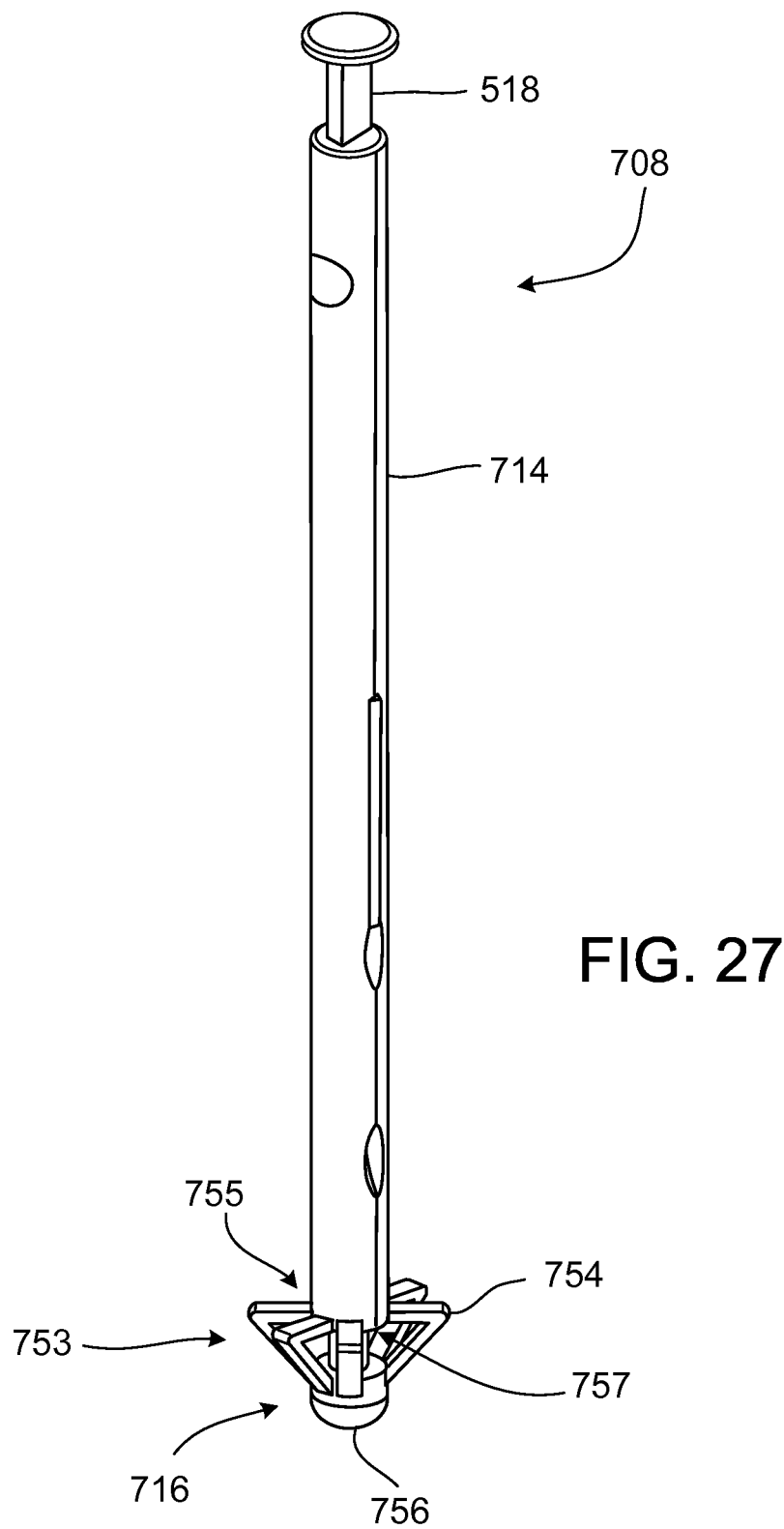
FIG. 27 is a perspective view of a suture passer guide that includes an expandable member having two groups of three collapsible arms.

While the suture passer guides 508, 608 have been described as including two collapsible arms 554 and four collapsible arms 654, respectively, in some embodiments, the suture passer guide includes a greater number of collapsible arms. As shown in FIG. 27, for example, a suture passer guide 708 includes an expandable member 716 having six collapsible arms 754 (i.e., two groups 753 that each include two collapsible arms 754) that are coupled at their distal end regions to a rounded base 756 and at their proximal end regions to an elongate tubular member 714. The collapsible arms 754 are similar in construction and function to the collapsible arms 554, 654 of the expandable members 516, 616 described above, with the exception that the collapsible arms 754 have a different width than those of the collapsible arms 554, 654. The rounded base 756 is similar in construction and function to the rounded bases 556, 656 of the expandable members 516, 616 described above, with the exception that the rounded base 756 includes a different number of hinges (i.e., hinges that couple to distal segments of the collapsible arms 754) than those of the rounded bases 556, 656. The elongate tubular member 714 is similar in construction and function to the elongate tubular members 514, 614 of the suture passer guides 508, 608 described above, with the exception that a distal end of the elongate tubular member 714 has a different edge profile (i.e., to allow coupling of the elongate tubular member 714 to the collapsible arms 754) than those of the elongate tubular members 514, 614.

The groups 753 of the collapsible arms 754 are spaced approximately 180° apart from each other (as measured from a vertical plane that extends through a center line of the middle collapsible arm 754 of each group 753). Circumferential gaps 755, 757 between the groups 753 extend about 90° to about 150° around the circumference of the expandable member 716. The circumferential gaps 755, 757 are typically about 30° to about 100° larger than the gaps between adjacent collapsible arms 754 within the groups 753. The gaps between adjacent collapsible arms 754 within the groups 753 can, for example, extend about 90° to about 150° around the circumference of the expandable member 716. Each collapsible arm 754 typically has a width of about 0.3 cm to about 0.8 cm.

The expandable member 716 can be retracted and expanded by pressing and releasing the button 518 located at the proximal end region of the elongate tubular member 614, which is coupled to the expandable member 716 via the internal shaft 568 and the spring 564 (shown in FIG. 25).

As compared to the suture passer guides 508, 608, the suture passer guide 708 requires slightly greater force to tilt within the surgical cavity during use. However, the additional collapsible members 754 provide an increased surface area of the expandable member 716 that contacts the inner lining of the surgical cavity. This increased surface area, as discussed above, results in increased distribution of the traction force and improves the stability of the suture passer guide 708 while the suture passer guide 708 is held against the inner lining of the surgical cavity and also reduces the probability that any collapsible arm 754 will tear or otherwise damage the inner lining of the surgical cavity while the suture passer guide 708 is held against the inner lining of the surgical cavity.

While the suture passer guides 508, 608, and 708 have been described as including two collapsible arms or two groups of collapsible arms that are spaced by two circumferential gaps, in certain embodiments, the suture passer guide includes more than two groups of collapsible arms. In certain embodiments, for example, the suture passer guide includes four groups of collapsible arms, and each of the adjacent groups are circumferentially spaced from one another by a circumferential gap. The circumferential gaps can increase the tiltability of the suture passer guide within a surgical cavity. The suture passer guide can further include four guide passages that are aligned with the four circumferential gaps. In other embodiments, the suture passer guide includes four collapsible arms (rather than groupings of arms) that are equally spaced around the circumference of the expandable member and includes four guide passages that are aligned with circumferential gaps formed between the adjacent collapsible arms. As discussed above, suture passer guides that include four guide passages that are circumferentially spaced around the suture passer guide can be used to position two sutures within a wound and can thus be used for repairing larger diameter wounds.

Figure 28:
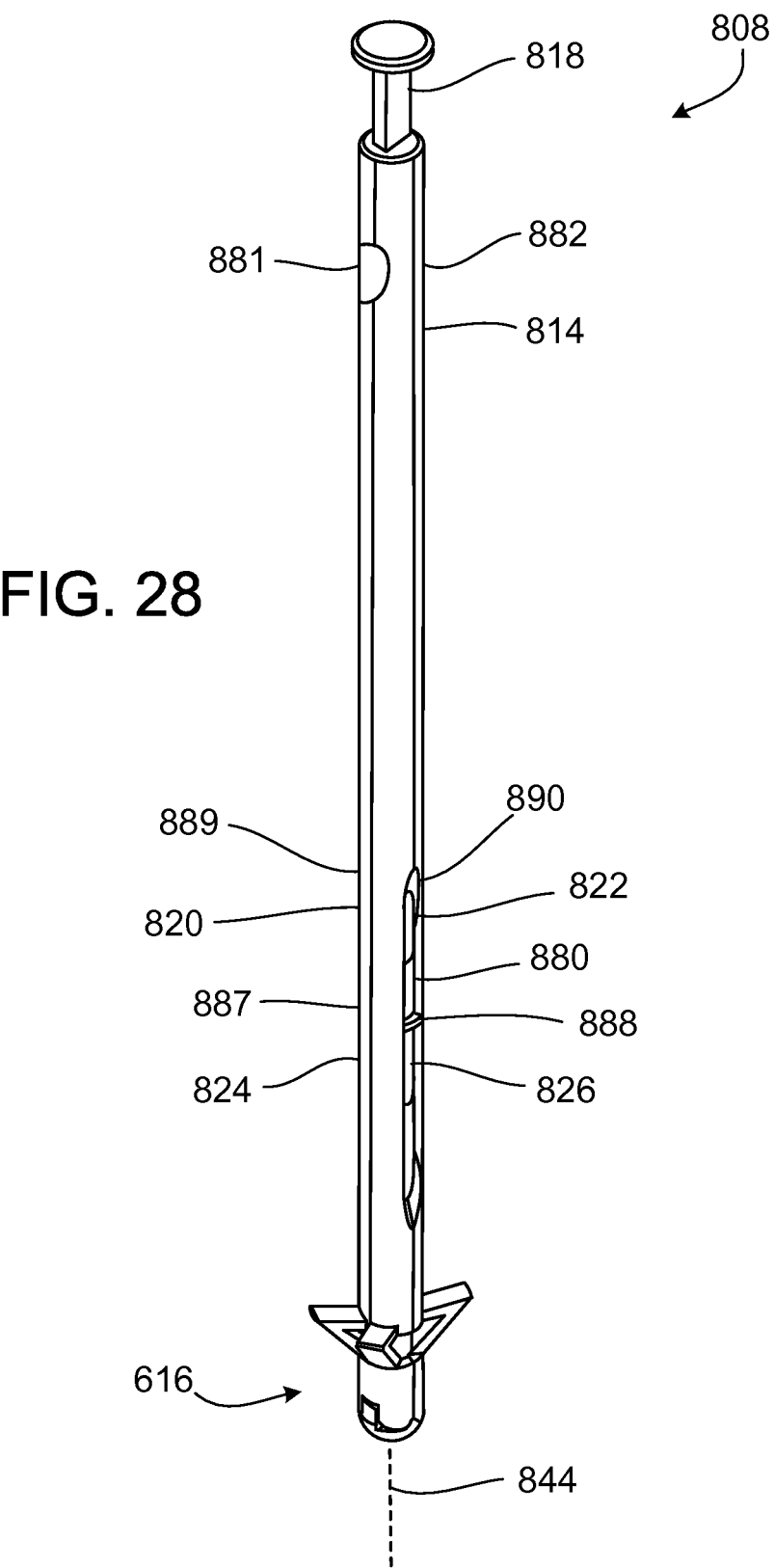
FIG. 28 is a perspective view of a suture passer guide that includes a moveable guide passage block.

While the suture passer guides above have been described as including one or more stationary guide passages, in certain embodiments, the suture passer guide includes a moveable guide passage block that allows a longitudinal location of the guide passages to be adjusted. For example, FIG. 28 illustrates a suture passer guide 808 that includes an adjustable block 880 situated within an elongate tubular member 814 and exposed via slots 889, 890 formed on either side of the elongate tubular member 814. The expandable member 616 is located at the distal end of the elongate tubular member 814, and a button 818 is positioned at the proximal end of the elongate tubular member 814 for expanding and retracting the expandable member 616.

Figure 29:
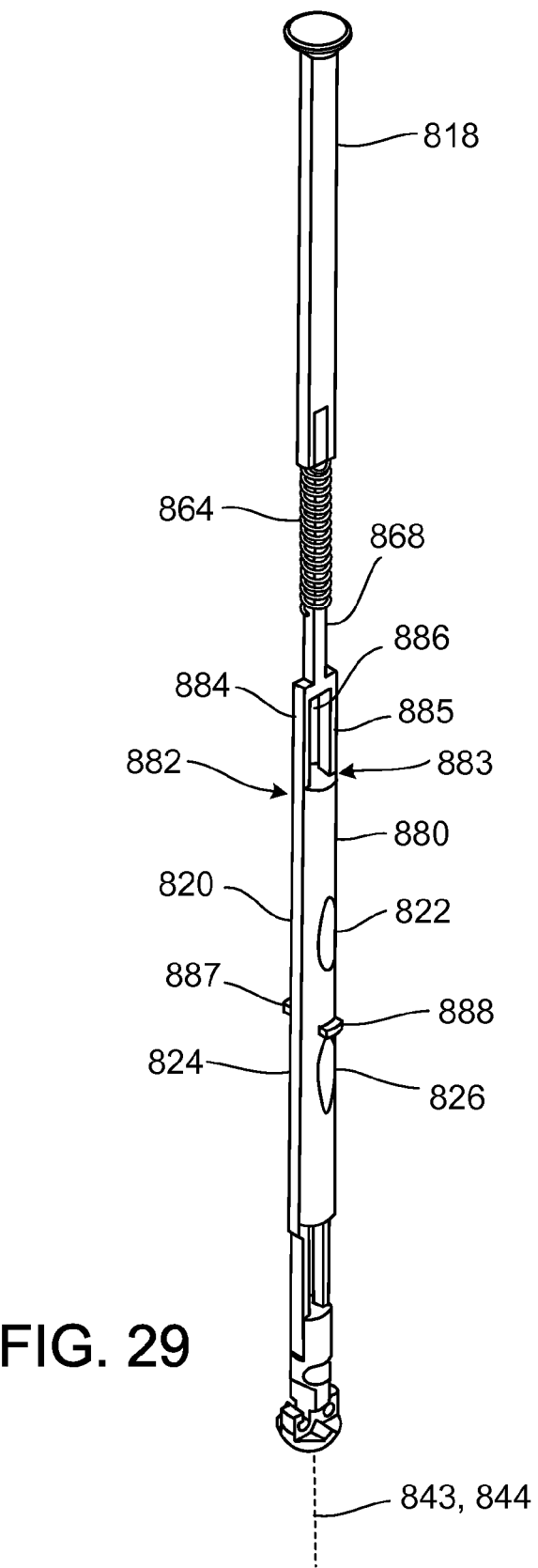
FIG. 29 is a perspective view of an inner shaft assembly and the moveable guide passage block of the suture passer guide of FIG. 28.

Referring to FIG. 29, which illustrates an inner shaft assembly of suture passer guide 808, the moveable block 880 includes a first guide passage that extends between openings 820, 826 and a second guide passage that extends between openings 822, 824. The guide passages extend at an angle of about 12° to about 30° (e.g., about 14°) relative to a longitudinal centerline 843 of the adjustable block 880, and a longitudinal distance between the proximal openings 820, 822 and the distal openings 824, 826 is about 3 cm to about 6 cm. The moveable block 880 further includes two opposing rectangular-shaped recesses 882, 883 located at left and right edges of the moveable block 880 and that open in a direction perpendicular to the openings 820, 822, 824, 826. The rectangular-shaped recesses 882, 883 are sized and shaped to mate with rails 884, 885 that partially form a channel 886 included within an internal shaft 868 of the suture passer guide 808 such that the longitudinal centerline 843 of the adjustable block 880 is disposed inline with a longitudinal axis 844 of the elongate tubular member 844. Two opposing projections 887, 888 extend from a surface of the adjustable block 880 at locations between the openings 820, 824 and the openings 822, 826, respectively, and allow a user to determine a proper position of the moveable block 880 within the channel 886 for accurate guidance of a suture passer through the guide passages. In some embodiments, the projections 887, 888 are of a different color than the moveable block 880 such that a visibility of the indicators 887, 888 is improved.

A length of the moveable block 880 is about 9 cm to about 10 cm, and a length of the channel 886 is about 11 cm to about 12 cm. Thus, the moveable block 880 has a sliding distance of about 2 cm to about 3 cm. The sliding distance allows the moveable block 880 to be positioned in multiple different positions along the length of the elongate tubular member 844 so that the suture passer guide 808 can be used in surgical walls ranging in thickness from about 2 cm to about 10 cm. Accordingly, during use of the suture passer guide 808 (i.e., once the suture passer guide 808 has been inserted through an endoscopic port positioned within a wound, and the endoscopic port has been subsequently removed from the wound), the moveable block 880 is slid along the rails 884, 885 of the internal shaft 868 until the projections 887, 888 are aligned with an external skin layer (e.g., the external skin layer 184) of the surgical wall. In this manner, the proximal openings 820, 824 are visible to the user, while the distal openings 822, 826 are positioned below the external skin layer of the surgical wall within the wound. The adjustability of the moveable block 880 allows the guide passages to be positioned for optimal guidance of a suture passer through the surgical wall and thus can improve the closure of the appropriate layers (e.g., the fascia 194 and the peritoneum 186) of the surgical wall. Furthermore, the single set of guide passages allows the suture passer guide 808 to be operated with simplicity in that a user of the suture passer guide 808 is not tasked with selecting a proper set of guide passages from more than one set of guide passages.

The moveable block 880 further includes a friction-generating feature such that the moveable block 880 is maintained in a desired position along the channel 886. In some embodiments, the friction-generating feature may include one or more cantilevered spring arms extending from the adjustable block 880 and resting against an inner surface of the elongate tubular member 814. In certain embodiments, the friction-generating feature may include one or more recesses extending from the surface of the moveable block 880 that seat around complimentary detents extending from an inner surface of the elongate tubular member 814. In some embodiments, the moveable block 880 may include a button that locks the block at a desired location along the rails 884, 885 of the internal shaft 868. For example, the button can include a small projection that engages one of several complementary recesses located within the moveable block.

In some embodiments, the moveable block 880 includes a finger gripping region positioned on the surface of the moveable block 880 and in proximity to one or more of the openings 820, 822, 824, 826 to improve the ease with which the moveable block 880 can be moved by a user of the suture passer guide 808.

Still referring to FIG. 29, the internal shaft 868 is configured to extend the expandable member 616 distally from the elongate tubular member 814. A proximal end of the internal shaft 868 is coupled to a spring 864, and a proximal end of the spring 864 is coupled to a button 818. The button 818 is operable to compress the spring 864 such that the internal shaft 868 can move distally within the elongate member 814.

Referring again to FIG. 28, a wall of the elongate tubular member 814 includes two elongate access slots 889, 890 for providing visibility and access to the openings 820, 822, 824, 826 and projections 887, 888 of the moveable block 880. The elongate access slots 889, 890 are centrally aligned with the openings 820, 822, 824, 826 and are sized such that the slots 889, 890 allow sufficient access to the openings 820, 822, 824, 826 (i.e., a suture passer can be passed through the slots 889, 890 and subsequently through the openings 820, 826 and the openings 822, 824, respectively). The access slots 889, 890 typically have a length of about 6 cm to about 10 cm. The elongate tubular member 814 further includes finger gripping depressions 881, 882. The elongate tubular member 814 can alternatively or additionally include etched rings to enhance the ability of the user to grip the suture passer guide 808.

While the moveable block 880 of the suture passer guide 808 has been described as having a particular range of dimensions and a particular sliding distance range, it should be understood that these dimensions and sliding distances can differ depending on the application for which the suture passer guide is to be used.

In some embodiments, the moveable block 880 further includes self-sealing elastic plugs (e.g., such as self-sealing elastic plugs similar to the plugs 161, 163 of the suture passer guide 108) sized to be disposed within the distal openings 824, 826 of the moveable block 880.

While the suture passer guide 808 has been described as including the expandable member 616, it should be appreciated that a suture passer guide including the moveable block 880 may alternatively include any of the expandable members described above.

Figure 30:
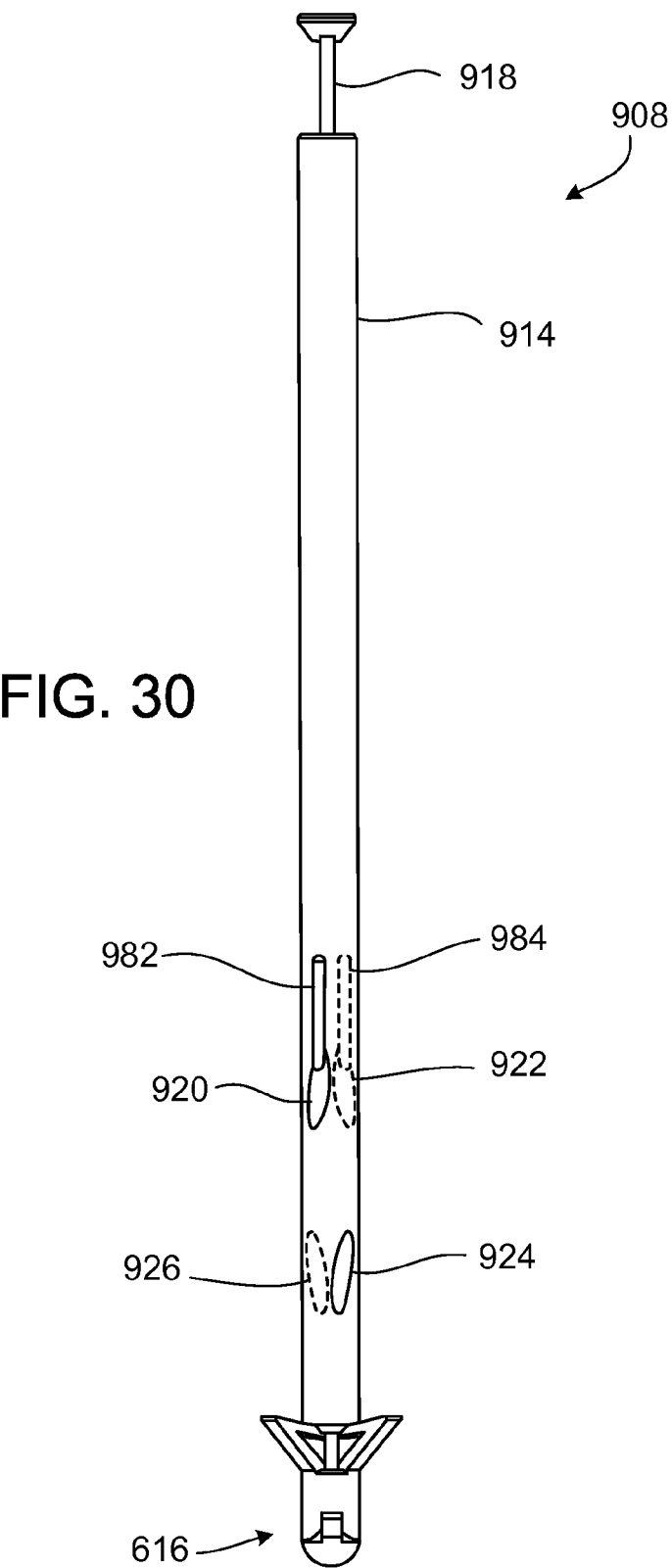
FIG. 30 is a perspective view of a suture passer guide that includes non-crossing guide passages.
Figure 31:
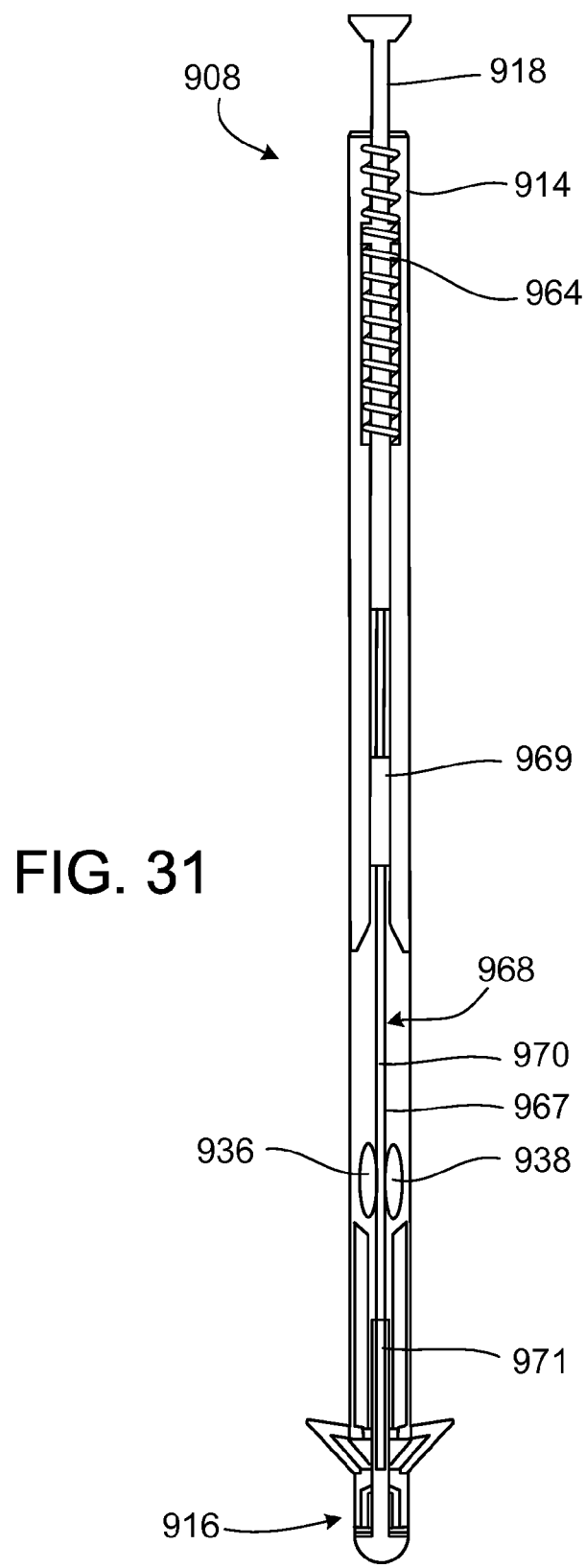
FIG. 31 is a cross-sectional view of the suture passer guide of FIG. 30.

While the suture passer guides above have been described as including guide passages that intersect along the longitudinal axis of the elongate tubular member, in certain embodiments, the suture passer guide includes non-crossing guide passages. For example, FIGS. 29 and 30 illustrate a suture passer guide 908 that includes first and second non-crossing guide passages 936, 938 that are positioned on opposite sides of an internal shaft 968 assembly located within an internal slot 967 of an elongate tubular member 914. The first and second guide passages extend through a solid core of the elongate tubular member 914 and between first proximal and distal openings 920, 926 and second proximal and distal openings 922, 924, respectively, that are defined by a sidewall of the elongate tubular member 914. The first and second guide passages 936, 938 extend at an angle of about 10° to about 30° (e.g., about 15°) relative to a longitudinal axis 944 of the elongate tubular member 914. The first and second proximal openings 920, 922 are circumferentially spaced about 180° apart from each other. Similarly, the first and second distal openings 924, 926 are circumferentially spaced about 180° apart from each other. The first proximal and distal openings are circumferentially spaced about 150° to about 170° (e.g., about 160°) apart from each other. Similarly, the second proximal and distal openings are circumferentially spaced about 150° to about 170° (e.g., about 160°) apart from each other.

Referring particularly to FIG. 29, elongate depressions 982, 984 extend upward from the proximal openings 920, 922 and are similar in construction and function to the elongate depressions 582, 584 of the suture passer guide 508, with the exception that the elongate depressions 982, 984 have a length different than that of the elongate depressions 582, 584. The length of the elongate depressions 982, 984 is typically about 1 cm to about 5 cm (e.g., about 3 cm). The elongate tubular member 914 is coupled at a distal end region to the expandable member 616 and at a proximal end region to a button 918 that is substantially similar in function to the button 118 of the suture passer guide 108.

Referring particularly to FIG. 30, the expandable member 616 can be retracted and expanded by pressing and releasing the button 918 located at the proximal end region of the elongate tubular member 914. The button 918 is coupled to the expandable member 616 via a spring 964 positioned around a shaft of the button 918 and the internal shaft assembly 968 in order to operate the expandable member 616 in this way. The inner shaft assembly 968 includes a proximal member 969 coupled to the button 918, a central rod 970 configured to slide within the internal slot 967 of the elongate tubular member 914, and a distal member 971 coupled to the rounded base 656 of the expandable member 616. The first and second guide passages 936, 938 are positioned on opposite sides of the central rod 970 and therefore do not intersect one another or the longitudinal axis 944 of the elongate tubular member.

The central rod 970 typically has a diameter of about 0.030 inches to about 0.125 inches, (e.g., about 0.040 inches). The relatively close fit of the central rod 970 within the internal slot 967 (as compared to the fit of the internal shaft 168 within the lumen of the elongate tubular member 114 of the suture passer guide 108) reduces the region through which gases can pass through the suture passer guide 908 and thus can reduce the loss of inflation pressure from the surgical cavity through the suture passer guide 908 during use of the suture passer guide 908. As the expandable member 616 of the suture passer guide 908 is pulled against the internal lining of the surgical cavity during use of the suture passer guide 908, the spring 964 typically collapses when the traction force reaches about 4 lbf to about 10 lbf (e.g., about 7 lbf) such that the expandable member 616 collapses and does not excessively damage the surgical wall at such traction forces. The diameter of the spring 964 is about 0.125 inches to about 0.5 inches (e.g., about 0.25 inches).

The non-crossing guide passages 936, 938 provide several advantages to the structure and use of the suture passer guide 908, as compared to the structure and use of the suture passer guide 108 having guide passages that intersect one another along the longitudinal axis 144 of the elongate member 114. For example, during use of the suture passer guide 108 (referring to FIG. 9G), as the suture passer 110 is passed through the second guide passage 138 of the suture passer guide 108 to retrieve the end 190 of the suture that is located within the surgical cavity 180, care must be taken to prevent the suture passer 110 from damaging the portion of the suture 188 that extends through the common center region of the guide passages 136, 138. The non-crossing feature of the guide passages 936, 938 allows a user of the suture passer 908 to avoid this potential complication since a suture passer will not come into contact with a suture extending through one guide passage 936, 938 while the suture passer is being passed through the other guide passage 936, 938.

In another example, during use of the suture passer guide 108 (referring to FIGS. 9F and 9G), as the suture passer 110 is passed through the guide passages 136, 138 of the suture passer guide 108, care must be taken to prevent the distal end of the suture passer 110 from becoming lodged within small gaps located between the lumen of the elongate tubular member 114 and the internal shaft 168. In some instances, such contact between a suture passer and a suture passer guide could damage either or both of the suture passer and the suture passer guide. The integral feature of the non-crossing guide passages 936, 938 (i.e., the guide passages 936, 938 extending through a solid core of the elongate tubular member 914) prevents such a complication since the non-crossing guide passages 936, 938 do not have any gaps in their formations through the solid core of the elongate tubular member 914.

In a further example, the upper distal guide passage openings 124, 126 of the suture passer guide 108 can, in some embodiments, overlap with a portion of the lower proximal guide passage openings 128, 130 (although not shown in such a configuration in FIGS. 1 and 2). During use of the suture passer guide 108 (referring to FIGS. 9F and 9G) having such a guide passage configuration, care must be taken to prevent the distal end of the suture passer 110 from exiting the wrong set of guide passage openings (i.e., when the suture passer guide is passed through the upper guide passages 136, 138, care must be taken to prevent the suture passer 110 from exiting the suture passer guide through the lower proximal openings 128, 130) and therefore passing through the peritoneum 186 at undesired puncture points. The circumferential offset of the non-crossing left and right guide passages of the suture passer guide 908 (in an embodiment where the suture passer 908 includes two or more sets of guide passages) prevents such a complication since distal openings of an upper set of guide passages will not overlap proximal openings of a lower set of guide passages. Furthermore, the non-overlapping feature of the guide passage openings results in maximal guide passage surface areas that can optimally guide a suture passer through the suture passer guides.

In yet another example, intersection regions of the guide passages 136, 138 and the guide passages 140, 142 within the suture passer guide 108 result in relatively thinned, weakened wall sections (i.e., resulting from void spaces generated by the intersection regions in the wall sections) of the elongate tubular member 114 as compared to thicker, stronger wall sections of the elongate tubular member 914 of the suture passer guide 908. Given that the elongate tubular member 914 does not have such void guide passage intersection regions, the thicker, stronger wall sections of the elongate tubular member 914 can better withstand forces exerted on the wall sections as the elongate tubular member 914 is assembled (e.g., bonded together from the wall sections) relative to the force that the elongate tubular member 114 can withstand during assembly. Furthermore, due to the thicker, stronger wall sections of the elongate tubular member 914, the elongate tubular member 914 can include more guide passages relative to its structural integrity (as compared to the elongate tubular member 114). Spacing a larger number of guide passages along the length of the elongate tubular member 914 can allow the suture passer guide 914 to be used to repair surgical walls having a larger range of thicknesses as compared those that can be repaired using the suture passer guide 108. Additionally, the absence of a guide passage intersection void region within the elongate tubular member 914 allows the guide passages 936, 938 to be oriented at any angle with respect to the longitudinal axis 944 of the elongate tubular member 914. In contrast, the angle at which the guide passages 136, 138 are oriented with respect to the longitudinal axis 114 of the elongate tubular member 114 is limited by a size of the resulting guide passage intersection void region that can be allowed to maintain a desired level of structural integrity of the elongate tubular member 114.

In another example, the non-crossing feature of the guide passages 936, 938 of the suture passer guide 908 allows two suture passers to be passed through the suture passer guide 908 simultaneously, while the crossing feature of the guide passages 136, 138 of the suture passer guide 108 only allows one suture passer to be passed through the suture passer guide 108 at a time.

In a further example, the circumferential offset of the non-crossing guide passages 936, 938 of the suture passer guide 908 improves the aesthetics of the suture passer guide 908 in that only one guide passage opening 920, 922, 924, 926 is completely visible from the outside of the elongate tubular member 914 at a time, whereas the alignment of the crossing guide passages 136, 138 of the suture passer guide 108 provides that at least two openings are visible simultaneously from the outside of the elongate tubular member 114. A smaller number of visible openings in the elongate tubular member 914 provides a simpler, cleaner look to the suture passer guide 908 as compared to that of the suture passer guide 108.

The various components of the suture passer guide 908, including the elongate member 914, the expandable member 616, and the inner shaft assembly 968, can be formed of one or more of a variety medical grade materials, including stainless steel, titanium, polycarbonate, Acrylonitrile butadiene styrene (ABS), polypropylene, acrylic, liquid crystal polymer (LCP), polyetheretherketone (PEEK), silicone, and thermoplastic elastomer (TPE). In some embodiments, the elongate tubular member 914 is typically made of polypropylene. In certain embodiments, the central rod 970 of the internal shaft assembly 968 is typically made stainless steel. In some embodiments, the proximal and distal members 979, 971 of the internal shaft assembly 968 are typically made of polycarbonate of another suitably stiff, strong plastic material.

While the suture passer guide 908 has been described as including one set of non-crossing guide passages, in some embodiments, the suture passer guide includes more than one set (for example, two, three, or four sets) of non-crossing guide passages. In such embodiments, the elongate tubular member 914 can also include one or more additional sets of elongate depressions extending from additional proximal openings and that are similar in shape and function to the elongate depressions 982, 984. In one embodiment, a suture passer guide includes a proximal set of non-crossing guide passages that extend at an angle of about 14° relative to a longitudinal axis of an elongate tubular member and a distal set of non-crossing guide passages that extend at an angle of about 16° relative to the longitudinal axis of the elongate tubular member.

In certain embodiments, the elongate tubular member 914 further includes finger gripping depressions similar to the finger gripping depressions 581, 582 of the suture passer guide 508. The elongate tubular member 914 can alternatively or additionally include etched rings similar to the etched rings 181 of the suture passer guide 108 described above.

In some embodiments, the suture passer guide 908 further includes self-sealing elastic plugs (e.g., such as self-sealing elastic plugs similar to the plugs 161, 163 of the suture passer guide 108) sized to be disposed within the distal openings 924, 926 of the elongate tubular member 914.

While the suture passer guide 908 has been described as including the expandable member 616, it should be appreciated that a suture passer guide including non-crossing guide passages may alternatively include any of the expandable members described above or no expandable member at all.

Figure 32:
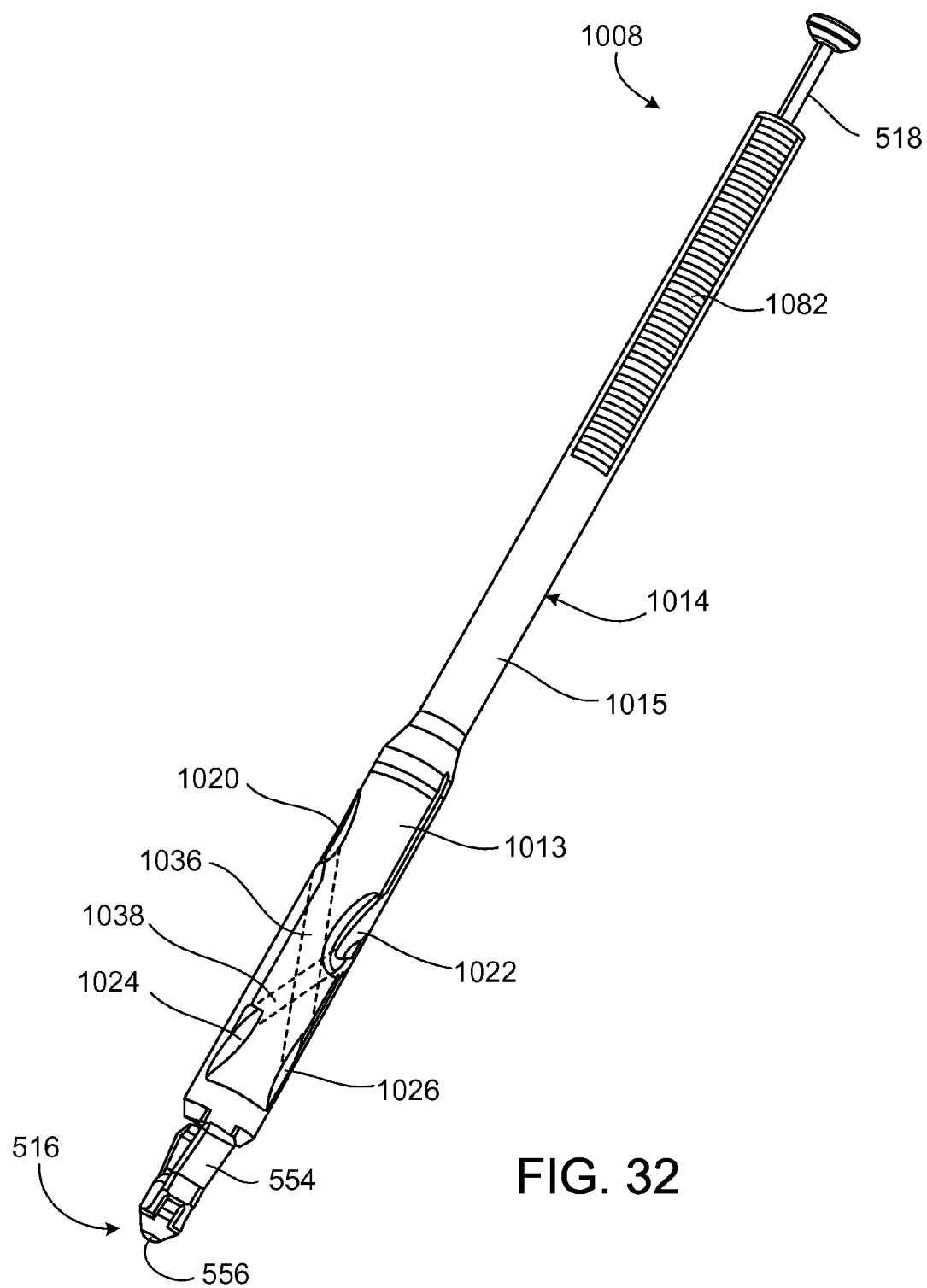
FIG. 32 is a perspective view of a suture passer guide including an elongate tubular member that forms four guide passages each of which terminates at substantially the same longitudinal position along the elongate tubular member.
Figure 33:
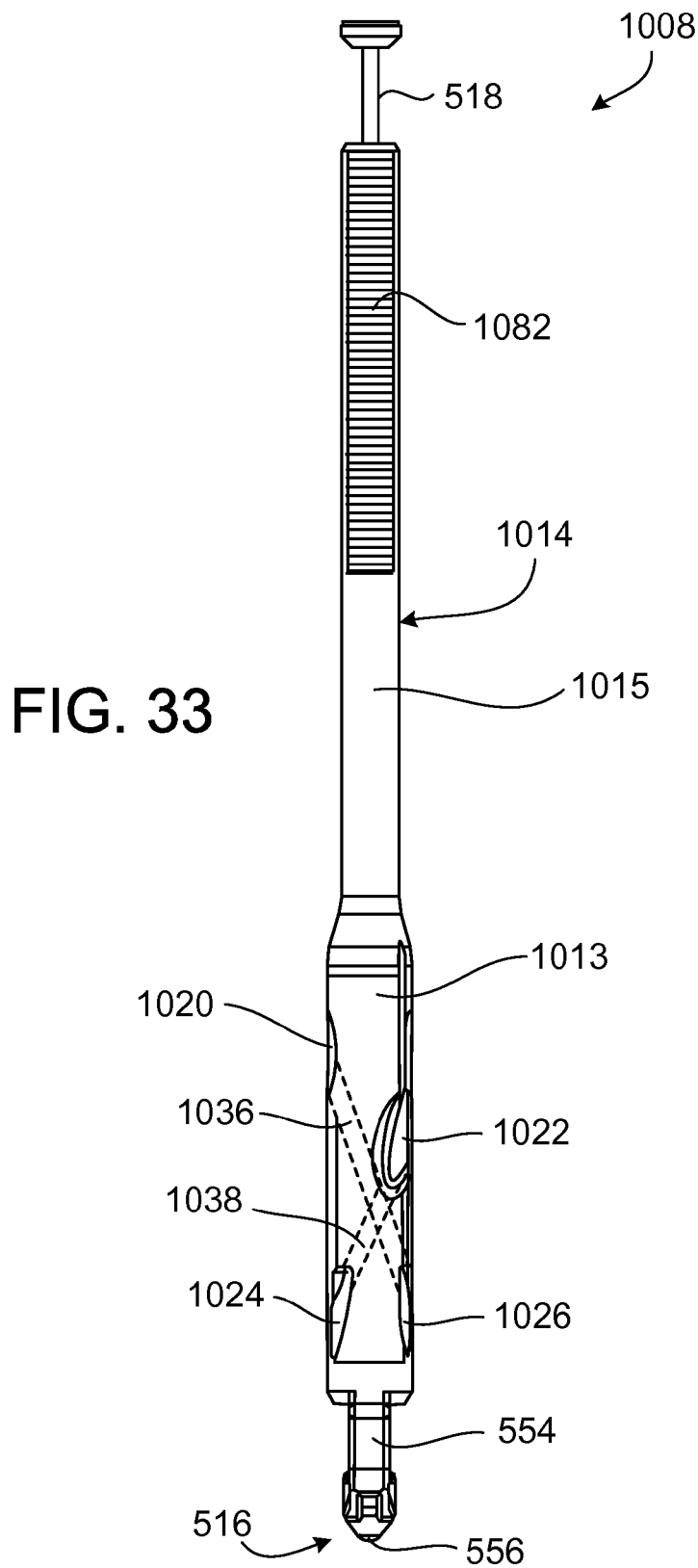
FIG. 33 is a front view of the suture passer guide of FIG. 32.
Figure 34:
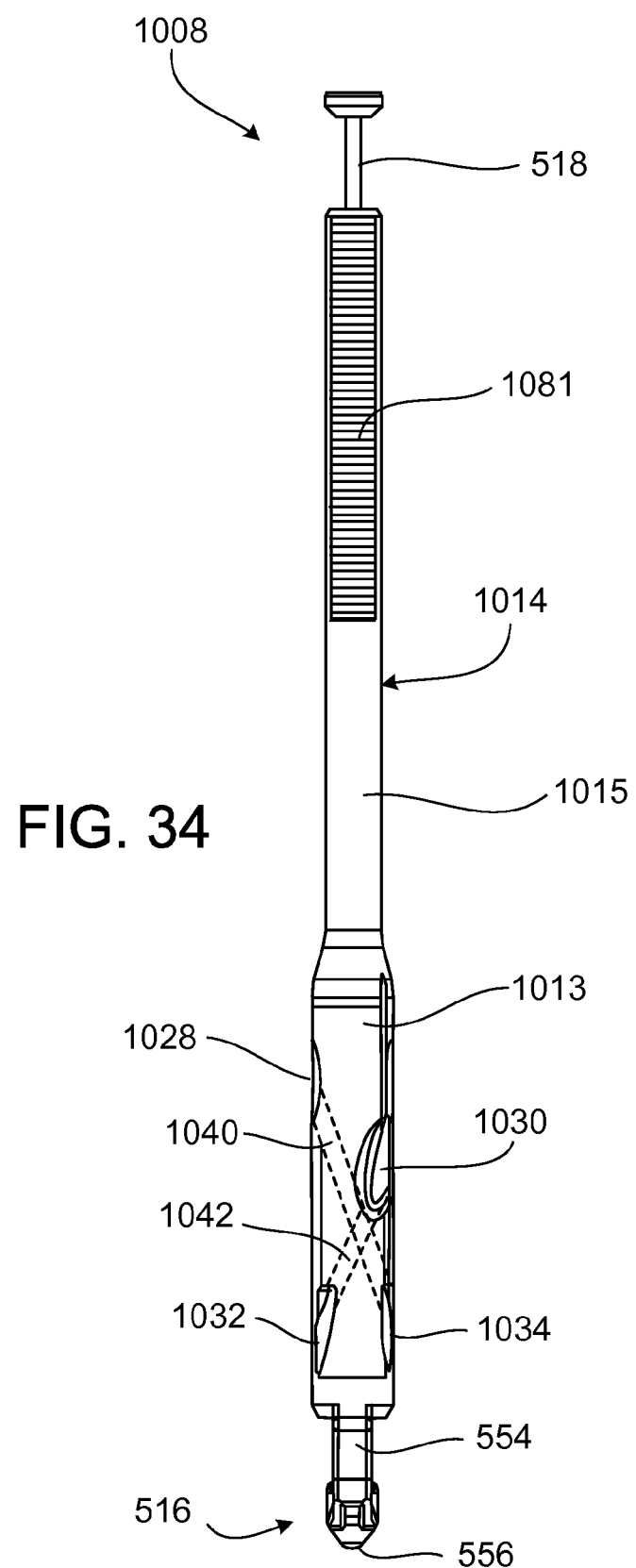
FIG. 34 is a back view of the suture passer guide of FIG. 32.

FIGS. 32, 33, and 34 illustrate perspective, front, and back views, respectively, of a suture passer guide 1008 that can be used to facilitate the repair of larger port site wounds than many of the suture passer guides discussed above. The suture passer guide 1008 includes an elongate tubular member 1014 that forms four guide passages 1036, 1038, 1040, 1042 each of which terminates at substantially the same longitudinal position along the elongate tubular member 1014. A distal portion 1013 of the elongate tubular member 1014, which forms the guide passages 1036, 1038, 1040, 1042, has a greater diameter than a proximal portion 1015 of the elongate tubular member 1014. In certain embodiments, the distal portion 1013 of the elongate tubular member 1014 has an outer diameter of 15 mm to 40 mm. The proximal portion 1015 of the elongate tubular member 1014 typically has an outer diameter of at least 8 mm.

The larger diameter of the distal portion 1013 of the elongate tubular member 1014 is typically selected to match the inner diameter of the endoscopic port through which the suture passer guide 1008 is inserted during use. For example, when intended for use with a 15 mm endoscopic port, the distal portion 1013 of the elongate tubular member 1014 of the suture passer guide 1008 would have an outer diameter of 15 mm. By selecting the outer diameter of the distal portion 1013 of the elongate tubular member 1014 to match the diameter of the endoscopic port, the distal portion 1013 of the elongate tubular member 1014 will substantially fill the endoscopic port site wound and will create a seal with the tissue adjacent the endoscopic port site wound to limit or prevent gas leakage from the surgical site.

The smaller diameter of the proximal portion 1015 of the elongate tubular member 1014 can help to make the suture passer guide 1008 lightweight and less bulky. Additionally, the smaller proximal portion 1015 of the elongate tubular member 1014 can provide easier handling and better visibility of the distal portion 1013 of the elongate tubular member 1013, making it easier to navigate suture passers through the guide passages 1036, 1038, 1040, 1042.

Still referring to FIGS. 32-34, the guide passage 1036 extends from the proximal opening 1020 to the distal opening 1026. The guide passage 1038 extends from the proximal opening 1022 to the distal opening 1024. The guide passage 1040 extends from the proximal opening 1028 to the distal opening 1034. The guide passage 1042 extends from the proximal opening 1030 to the distal opening 1032. The proximal openings 1020, 1022, 1028, 1030 are circumferentially spaced from one another around the elongate tubular member 1014, and the distal openings 1024, 1026, 1032, 1034 are circumferentially spaced from one another around the elongate tubular member 1014. As a result of this arrangement, the guide passages 1036 and 1038 extend along the front side of the internal shaft, which extends through a central lumen of the elongate tubular member 1014 and connects the expandable member 526 to the button 518, while the guide passages 1040 and 1042 extend along the back side of the internal shaft.

Typically, the guide passages 1036 and 1038 intersect one another and the guide passages 1040 and 1042 intersect one another. The intersection area of the passages is limited to help prevent a suture passer being passed through one of the passages from catching or snagging a suture previously positioned in the intersecting passage. For example, the intersection area of the guide passages can be limited to about one half of the diameter of the suture passer to be used with the suture passer guide 1008. This arrangement increases the likelihood that the suture passer will simply be deflected back into its intended guide passage (as opposed to becoming hung up at the intersection area) if it makes contact with the intersection area when being passed through guide passage.

Each of the distal openings 1024, 1026, 1032, 1034 is located at approximately the same longitudinal position along the elongate tubular member 1014. In certain embodiments, each of the distal openings 1024, 1026, 1032, 1034 is longitudinally spaced from the distal end of the elongate tubular member 1014 by about 1 cm to about 5 cm (e.g., about 2 cm).

The guide passages 1036, 1038, 1040, 1042 extend through the elongate tubular member 1014 at similar angles relative to the longitudinal axis of the suture passer guide 1008. Each of the guide passages 1036, 1038, 1040, 1042 can, for example, extend through the elongate tubular member 1014 at an acute angle of 10 degrees to 30 degrees (e.g., 15 degrees to 20 degrees) relative to the longitudinal axis. In some embodiments, the guide passages 1036 and 1040 extend through the elongate tubular member 1014 at an angle of 16 degrees relative to the longitudinal axis, and the guide passages 1038 and 1042 extend through the elongate tubular member 1014 at an angle of 18 degrees relative to the longitudinal axis. This arrangement, along with the longitudinal positioning of the guide passages 1036, 1038, 1040, 1042 along the elongate tubular member 1014, can help to ensure that approximately the same suture bite is achieved with each of the guide passages 1036, 1038, 1040, 1042 during an endoscopic port site wound repair procedure.

While the distal openings 1024, 1026, 1032, 1034 are located at approximately the same longitudinal position along the elongate tubular member 1014, the proximal openings 1020, 1022, 1028, 1030 are longitudinally staggered along the elongate tubular member 1014. This arrangement permits some of the proximal openings 1020, 1022, 1028, 1030 to be located in the same circumferential region of the elongate tubular member 1014 without interfering with one another. As a result, the guide passages 1036, 1038, 1040, 1042 can extend through the distal portion 1013 of the elongate tubular member 1014 at desired angles without having to significantly increase the diameter of the distal portion 1013 of the elongate tubular member 1014.

As discussed below, the guide passages 1036 and 1038 are typically used as a pair to place one suture, and the guide passages 1040 and 1042 are typically used as a pair to place a second suture. In some embodiments, rings of a first color (e.g., orange) are provided around the proximal openings 1020 and 1022 of the guide passages 1036 and 1038, while rings of a second color (e.g., blue) are provided around the proximal openings 1028 and 1030 of the guide passages 1040 and 1042. Alternatively, any of various other markings (e.g., text, letter, characters, symbols) can be used to identify the respective pairs of guide passages.

The elongate tubular member 1014 is illustrated as including etched rings 1081, 1082 along its proximal portion 1015 to enhance gripability. Alternatively or additionally, round depressions can be provided along the proximal portion 1015 of the elongate tubular member 1014 to provide finger gripping surfaces near the proximal end of the elongate tubular member 514.

In some embodiments, the suture passer guide 1008 further includes one or more self-sealing elastic plugs sized disposed within the distal openings 1024, 1026, 1032, 1034 of the elongate tubular member 1014 and/or an elastic film that surrounds the expandable member 516. The self-sealing plugs and film can be similar to the plugs 161, 163 and the film 160, respectively, of the suture passer guide 108 described above and can, for example, serve to maintain the inflation pressure within a surgical cavity during use of the suture passer guide 1008.

In certain embodiments, the suture passer guide 1008 further includes one or more surface features for determining a surgical wall thickness. Examples of such surface features include ruler markings and colored bands similar to the ruler markings 179 and the colored bands 176, 178, respectively, of the suture passer guide 108 described above.

The suture passer guide 1008 is generally used in a manner similar to the suture passer guides discussed above. Once the suture passer guide 1008 has been positioned in the port site wound with the expandable member 516 expanded, the user applies a proximal force to the suture passer guide 1008 and passes a suture passer loaded with a first suture through the guide passage 1036 and is used to deposit the first suture within the body cavity of the patient. The suture passer is then removed from the guide passage 1036 and inserted through the guide passage 1038 to retrieve the first suture from the body cavity of the patient. Subsequently, while applying a proximal force to the suture passer guide 1008, a suture passer loaded with a second suture is passed through the guide passage 1040 and is used to deposit the second suture within the body cavity of the patient. The suture passer is then removed from the guide passage 1040 and inserted through the guide passage 1042 to retrieve the second suture. The suture passer guide 1008 is then removed and the first and second sutures are tied to close the wound.

While the above-described method of using the suture guide passer 1008 involves using the guide passages 1036 and 1038 as a pair and using the guide passages 1040 and 1042 as a pair, other techniques are possible. In some cases, for example, one suture can be threaded through the guide passages 1036 and 1040 and another suture can be threaded through the guide passages 1038 and 1042 to allow the surgeon to carry out a figure of 8 closure technique.

While the proximal portion 1015 of the suture passer guide 1008 has been described as having a smaller diameter than distal portion 1014, in other embodiments, the suture passer guide has a uniform diameter along its length. In such embodiments, for example, the outer diameter of the suture passer guide can be approximately equal to the inner diameter of an endoscopic port with which the suture passer guide is intended to be used. This arrangement can help to prevent gases from escaping from a patient between the suture passer guide and the endoscopic port and can thus help to maintain pneumoperitoneum during endoscopic port site wound repair procedures.

While the distal openings 1024, 1026, 1032, 1034 have been described as being located at approximately the same longitudinal position along the elongate tubular member 1014 and the proximal openings 1020, 1022, 1028, 1030 have been described as being longitudinally staggered along the elongate tubular member 1014, in certain embodiments, the proximal openings 1020, 1022, 1028, 1030 are located at approximately the same longitudinal position along the elongate tubular member 1014 and the distal openings 1024, 1026, 1032, 1034 are longitudinally staggered along the elongate tubular member 1014. In such embodiments, the angles of the guide passages are typically selected to ensure that, in the case of a laparoscopic procedure, a suture passer passed through each of the guide passages pierces the peritoneum of the patient at approximately the same distance from the longitudinal axis of the suture passer guide and thus achieves substantially the same suture bite with each guide passage. While the guide passages 1036 and 1038 and the guide passages 1040 and 1042 have been described as intersecting one another, in some embodiments, the guide passages do not intersect one another.

While the suture passer guide 1008 has been described as including two pairs of guide passages that can be used for repairing an endoscopic port side wound, in certain embodiments, the suture passer guide includes more than two pairs of guide passages. For example, the suture passer guide can include three pairs of guide passages or for closing larger endoscopic port site wounds with three sutures or can include four pairs of guide passages for closing larger endoscopic port site wounds with four sutures.

While the expandable member 516 of the suture passer guide 1008 includes collapsible arms 554 that are secured at their proximal and distal ends to the elongate tubular member 1014 and the rounded base 556, respectively, it should be understood that any of the various other types of expandable members described herein can alternatively be used.

While many of the suture passer guides discussed above have been described as being used to repair an endoscopic port site wound created during a laparoscopic procedure, it should be understood that the suture passer guides described herein can be used to repair endoscopic port site wounds created during any endoscopic procedure.

What is claimed is:

1. A suture passer guide comprising:
an elongate member having a longitudinal axis; and
an expandable member secured to a distal end region of the elongate member, the expandable member configured to be positioned in an expanded position in which the expandable member extends radially beyond the elongate member, the expandable member comprising a first collapsible arm and a second collapsible arm that are spaced around a circumference of the expandable member, the expandable member defining a first gap that extends between the first and second collapsible arms around the circumference of the expandable member, and the first gap being open and uncovered,
wherein the elongate member defines a first proximal opening and a first distal opening that are substantially aligned with one another such that a suture passer can be extended through the first proximal and distal openings at an acute angle relative to the longitudinal axis of the elongate member, and the first gap defined by the expandable member is longitudinally aligned with the first distal opening such that the suture passer, when extended through the first proximal and distal openings with the expandable member in the expanded position, passes through the first gap extending between the first and second collapsible arms, is spaced from the expandable member along the length of the expandable member, and can position an unsecured end region of a suture within the first gap.

2. The suture passer guide of claim 1, wherein the suture passer guide is configured to be passed through a lumen of an endoscopic port when the expandable member is positioned in a collapsed position.

3. The suture passer guide of claim 2, wherein the expandable member is configured to extend laterally beyond the endoscopic port when the suture passer guide is disposed within the lumen of the endoscopic port with the distal end region extending distally from the endoscopic port and the expandable member is in the expanded position.

4. The suture passer guide of claim 2, wherein the expandable member is configured so that when the suture passer guide is positioned within an endoscopic port site wound and the expandable member is in the expanded position within a body cavity adjacent the endoscopic port site wound, the suture passer guide can be pulled proximally to apply an outward force to a wall forming the body cavity on either side of the endoscopic port site wound.

5. The suture passer guide of claim 1, wherein the expandable member is biased to the expanded position and is configured to automatically expand as the expandable member is extended through and distally beyond a lumen of an endoscopic port.

6. The suture passer guide of claim 1, wherein a first end region of each of the collapsible arms is secured to the distal end region of the elongate member, a second end region of each of the collapsible arms is secured to a base that is axially moveable relative to the elongate member, and a middle region of each of the collapsible arms is secured to the first and second end regions of each of the collapsible arms.

7. The suture passer guide of claim 6, wherein axial movement of the base distally relative to the elongate member causes the expandable member to collapse, and axial movement of the base proximally relative to the elongate member causes the expandable member to expand.

8. The suture passer guide of claim 7, further comprising a shaft that is connected to the base and extends through a lumen of the elongate member, the shaft being axially movable relative to the elongate member to move the base axially relative to the elongate member.

9. The suture passer guide of claim 1, further comprising a suture positioning arm secured to an arm of the expandable member and configured to extend radially outward from the arm, the suture positioning arm being configured to hold a suture.

10. The suture passer guide of claim 1, further comprising a film secured to the expandable member, the film at least partially surrounding the expandable member.

11. The suture passer guide of claim 1, further comprising a shaft having a distal end region secured to the expandable member, wherein distal movement of the shaft places the expandable member in a collapsed position and proximal movement of the shaft places the expandable member in the expanded position.

12. The suture passer guide of claim 1, further comprising a shaft disposed within a lumen of the elongate member, the shaft defining a first passage that can be aligned with the first proximal and distal openings.

13. The suture passer guide of claim 12, wherein the first passage is aligned with the first proximal and distal openings when the shaft is disposed in a proximal position.

14. The suture passer guide of claim 13, wherein the shaft defines a second passage that can be aligned with second proximal and distal openings defined by the elongate member.

15. The suture passer guide of claim 14, wherein the second passage is aligned with the second proximal and distal openings when the shaft is disposed in the proximal position.

16. The suture passer guide of claim 1, further comprising a seal that covers at least one of the first proximal and distal openings.

17. The suture passer guide of claim 16, wherein the seal substantially prevents gases from passing through the at least one of the first proximal and distal openings such that pressure within a pressurized body cavity can be substantially maintained while the suture passer guide is disposed in the pressurized body cavity.

18. The suture passer guide of claim 1, wherein the elongate member defines a second proximal opening and a second distal opening that are substantially aligned with one another such that the suture passer can be extended through the second proximal and distal openings at an acute angle relative to the longitudinal axis of the elongate member.

19. The suture passer guide of claim 18, wherein the first proximal opening is distal to the second proximal opening, and the first distal opening is distal to the second distal opening.

20. The suture passer guide of claim 18, wherein the elongate member defines a third proximal opening and a third distal opening that are substantially aligned with one another such that the suture passer can be extended through the third proximal and distal openings at an acute angle relative to the longitudinal axis of the elongate member.

21. The suture passer guide of claim 20, wherein the elongate member defines a fourth proximal opening and a fourth distal opening that are substantially aligned with one another such that the suture passer can be extended through the fourth proximal and distal openings at an acute angle relative to the longitudinal axis of the elongate member.

22. The suture passer guide of claim 18, wherein the first distal opening is located in a first colored region of the elongate member and the second distal opening is located in a second colored region of the elongate member, the first colored region being a different color than the second colored region.

23. The suture passer guide of claim 22, wherein the colored regions indicate to a user which of the proximal and distal openings should be used for a procedure.

24. The suture passer guide of claim 1, further comprising a measuring scale along a distal end region of the elongate member, the scale indicating a distance between markings of the scale and a proximal end of the expandable member.

25. The suture passer guide of claim 24, wherein the measuring scale can be used to determine a thickness of tissue through which the suture passer guide is inserted.

26. The suture passer guide of claim 1, wherein the first proximal and distal openings are defined by respective portions of the elongate member that are circumferentially spaced by about 180 degrees.

27. The suture passer guide of claim 1, wherein the expandable member comprises one or more additional collapsible arms that are spaced around the circumference of the expandable member.

28. The suture passer guide of claim 1, wherein the first gap between the first and second collapsible arms extends about 30° to about 180° around the circumference of the expandable member.

29. The suture passer guide of claim 1, wherein the first and second collapsible arms are in first and second groups of collapsible arms that are spaced apart around the circumference of the expandable member.

30. The suture passer guide of claim 29, wherein the first gap is defined between two consecutive groups of collapsible arms and is larger than gaps between adjacent collapsible arms within the groups.

31. The suture passer guide of claim 29, wherein the first gap is defined between two consecutive groups of collapsible arms.

32. The suture passer guide of claim 1, wherein the elongate member defines a first guide passage that extends from the first proximal opening to the first distal opening.

33. The suture passer guide of claim 32, wherein an entire length of the first guide passage is laterally offset from the longitudinal axis such that the first guide passage does not intersect the longitudinal axis.

34. The suture passer guide of claim 33, further comprising an inner shaft that extends along the longitudinal axis.

35. The suture passer guide of claim 32, wherein the elongate member defines a second guide passage that extends from a second proximal opening to a second distal opening.

36. The suture passer guide of claim 35, wherein an entire length of the first guide passage is laterally offset from the longitudinal axis in a first direction such that the first guide passage does not intersect the longitudinal axis, and an entire length of the second guide passage is laterally offset from the longitudinal axis in a second direction opposite the first direction such that the second guide passage does not intersect the longitudinal axis.

37. The suture passer guide of claim 36, wherein the elongate member defines a lumen that extends along the longitudinal axis, and the suture passer guide further comprises an inner rod that is slidable within the lumen.

38. The suture passer guide of claim 1, wherein the suture passer guide is configured such that the suture passer, when extended through the first proximal and distal openings and disposed within the first gap extending between the first and second collapsible arms, is free from contact with any portion of the expandable member or any structure defined by the expandable member.

39. The suture passer guide of claim 1, wherein the suture passer guide is configured such that an entire length of the suture passer guide can be passed through an endoscopic port.

40. The suture passer guide of claim 1, wherein the suture passer guide is configured such that an endoscopic port can be proximally removed from the suture passer guide when the expandable member is positioned in the expanded position within a body cavity adjacent an endoscopic port site wound.

41. A suture passer guide comprising:
an elongate member having a longitudinal axis; and
an expandable member secured to a distal end region of the elongate member, the expandable member configured to be positioned in an expanded position in which the expandable member extends radially beyond the elongate member, the expandable member comprising a first collapsible arm and a second collapsible arm that are spaced around a circumference of the expandable member, and the expandable member defining a first gap that extends between the first and second collapsible arms around the circumference of the expandable member,
wherein the elongate member defines a first proximal opening and a first distal opening that are substantially aligned with one another such that a suture passer can be extended through the first proximal and distal openings at an acute angle relative to the longitudinal axis of the elongate member, and the first gap defined by the expandable member is longitudinally aligned with the first distal opening such that the suture passer, when extended through the first proximal and distal openings with the expandable member in the expanded position, passes through the first gap extending between the first and second collapsible arms, is spaced from the expandable member along the length of the expandable member, is free from contact with any portion of the expandable member or any structure defined by the expandable member, and can position an unsecured end region of a suture within the first gap.

* * * * *